United States Patent
Yamaguchi et al.

(10) Patent No.: US 8,593,513 B2
(45) Date of Patent: Nov. 26, 2013

(54) IMAGE CAPTURING APPARATUS HAVING FIRST AND SECOND LIGHT RECEPTION SECTIONS, IMAGE CAPTURING METHOD, AND COMPUTER-READABLE MEDIUM

(75) Inventors: Hiroshi Yamaguchi, Kanagawa (JP); Akira Mizuyoshi, Saitama (JP); Hiroshi Sunagawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 1043 days.

(21) Appl. No.: 12/385,219

(22) Filed: Apr. 1, 2009

(65) Prior Publication Data

US 2009/0262225 A1     Oct. 22, 2009

(30) Foreign Application Priority Data

Apr. 2, 2008   (JP) ................. 2008-095966
Apr. 2, 2008   (JP) ................. 2008-095983
Jun. 12, 2008  (JP) ................. 2008-154516

(51) Int. Cl.
*A61B 1/04* (2006.01)
*A61B 1/06* (2006.01)
*A61B 1/00* (2006.01)

(52) U.S. Cl.
USPC ............................................ 348/68; 600/109

(58) Field of Classification Search
USPC ................. 348/45, 61, 65, 68–70, 265, 370; 396/17; 600/109, 160
See application file for complete search history.

(56) References Cited

U.S. PATENT DOCUMENTS

| | | | |
|---|---|---|---|
| 6,293,911 B1 * | 9/2001 | Imaizumi et al. ............. | 600/160 |
| 6,570,615 B1 | 5/2003 | Decker et al. | |
| 6,678,398 B2 | 1/2004 | Wolters et al. | |
| 6,730,019 B2 | 5/2004 | Irion | |
| 7,289,140 B2 | 10/2007 | Kobayashi | |
| 7,745,771 B2 | 6/2010 | Troxell et al. | |
| 2002/0120181 A1 | 8/2002 | Irion | |
| 2003/0158470 A1 | 8/2003 | Wolters et al. | |
| 2003/0176768 A1 * | 9/2003 | Gono et al. ............. | 600/109 |
| 2004/0155957 A1 | 8/2004 | Kobayashi | |
| 2006/0149133 A1 | 7/2006 | Sugimoto et al. | |
| 2007/0014553 A1 | 1/2007 | Endo | |
| 2007/0041720 A1 | 2/2007 | Iketani | |
| 2008/0018733 A1 | 1/2008 | Hasegawa | |
| 2008/0039696 A1 * | 2/2008 | Kamihara ............. | 600/181 |
| 2009/0065679 A1 | 3/2009 | Tanimoto | |
| 2009/0082625 A1 | 3/2009 | Gono | |

FOREIGN PATENT DOCUMENTS

| | | |
|---|---|---|
| EP | 1 669 019 A2 | 6/2006 |
| EP | 1905344 A1 | 4/2008 |
| JP | 2004-236952 | 8/2004 |
| JP | 2006-166940 | 6/2006 |

(Continued)

OTHER PUBLICATIONS

European Search Report dated Jun. 9, 2010.
European Search Report dated Sep. 8, 2009.
United States Office Action dated Apr. 24, 2012, in U.S. Appl. No. 12/556,496.

(Continued)

*Primary Examiner* — James Hannett
*Assistant Examiner* — Carramah J Quiett
(74) *Attorney, Agent, or Firm* — McGinn Intellectual Property Law Group, PLLC

(57) ABSTRACT

An image capturing apparatus includes: a light irradiation section that irradiates a subject with a plurality of irradiation light rays resulting from combining light rays having respectively different spectrum forms in respectively different combinations, at respectively different timings; and an image capturing section that captures a plurality of images of the subject irradiated with the plurality of irradiation light rays, at respectively different timings.

17 Claims, 27 Drawing Sheets

(56) References Cited

FOREIGN PATENT DOCUMENTS

| JP | 2007-202589 | 8/2007 |
| WO | WO 03/059150 A2 | 7/2003 |
| WO | WO 2005/030328 A2 | 4/2005 |
| WO | WO 2007/010709 A1 | 1/2007 |

OTHER PUBLICATIONS

United States Office Action dated May 2, 2012, in U.S. Appl. No. 12/556,481.
United States Notice of Allowance dated Mar. 16, 2012, in U.S. Appl. No. 12/561,050.

* cited by examiner

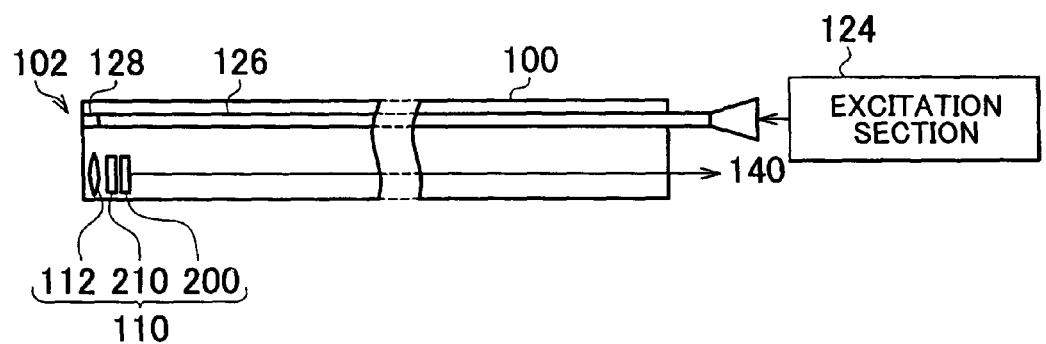
F I G . 2

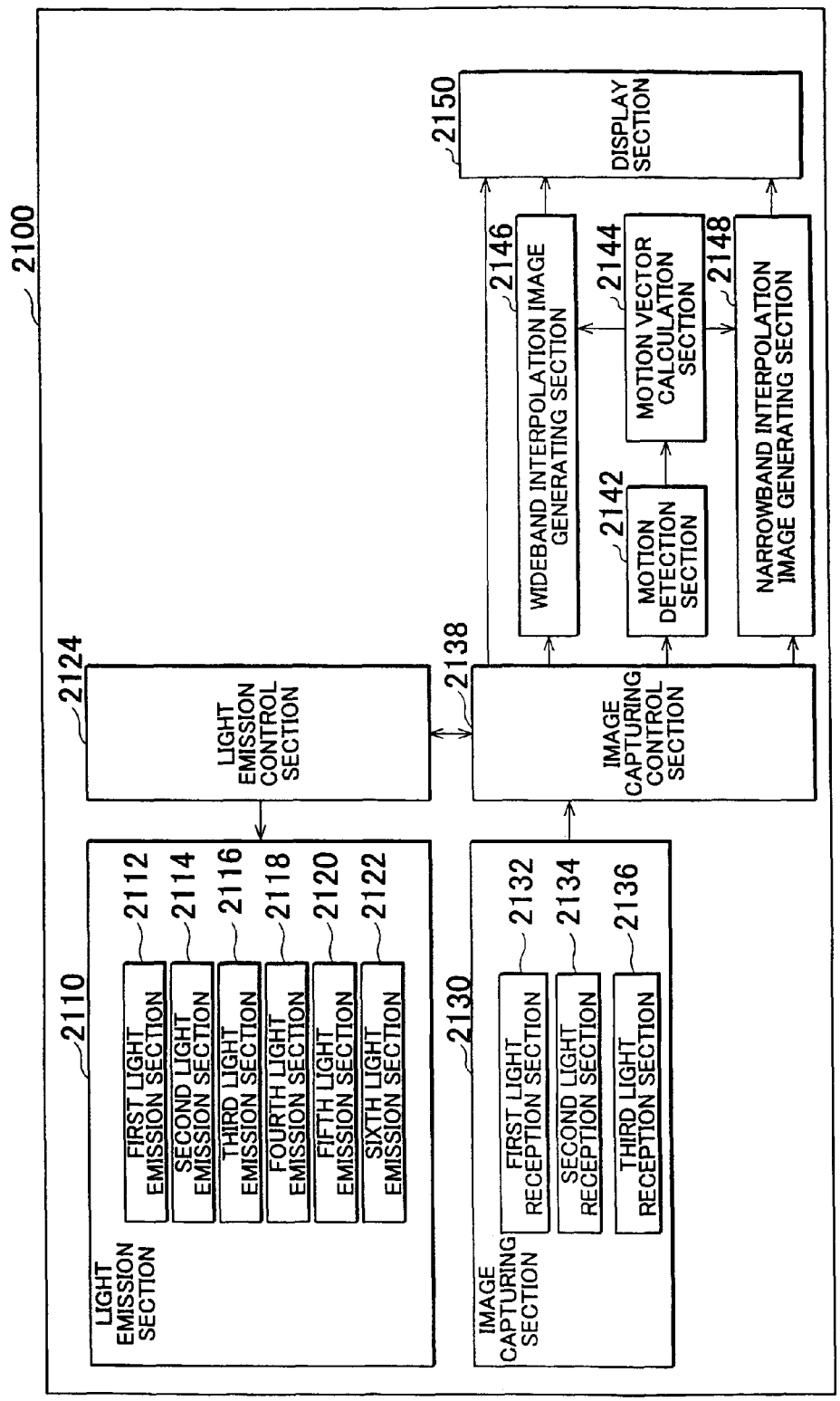
F I G. 9

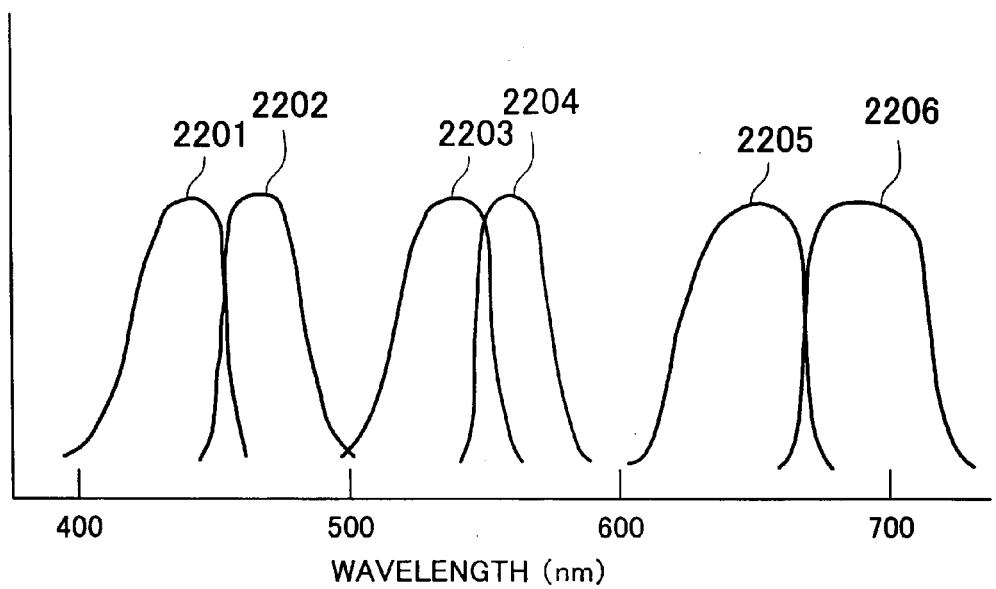
F I G. 10

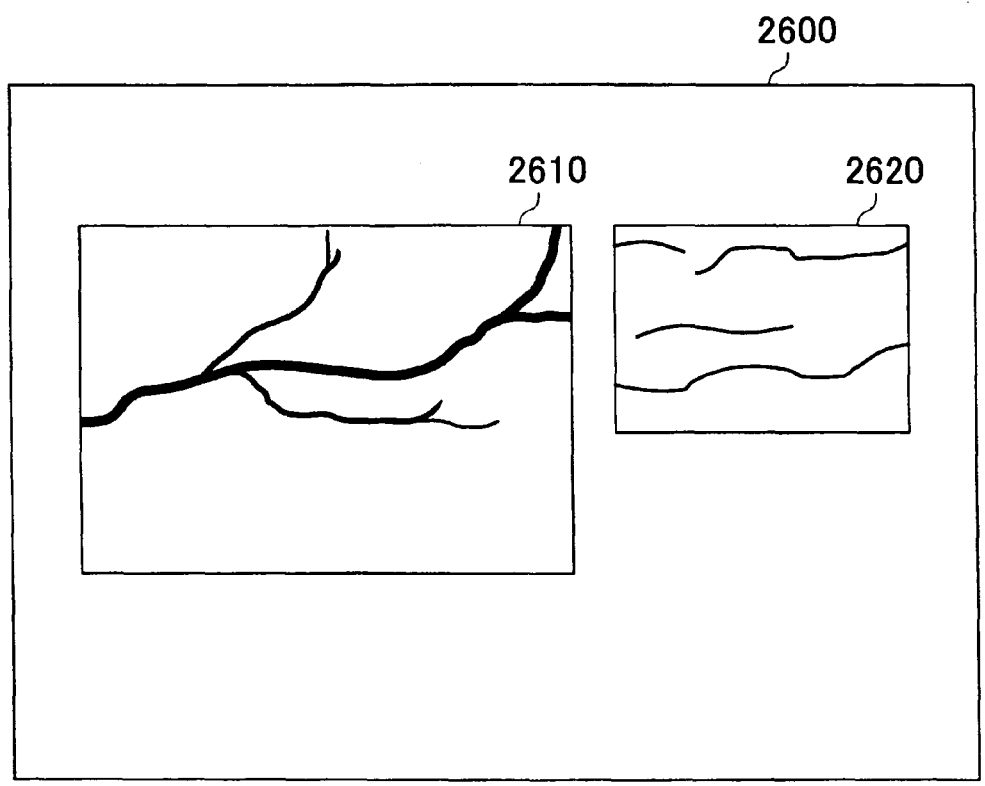
F I G . 14

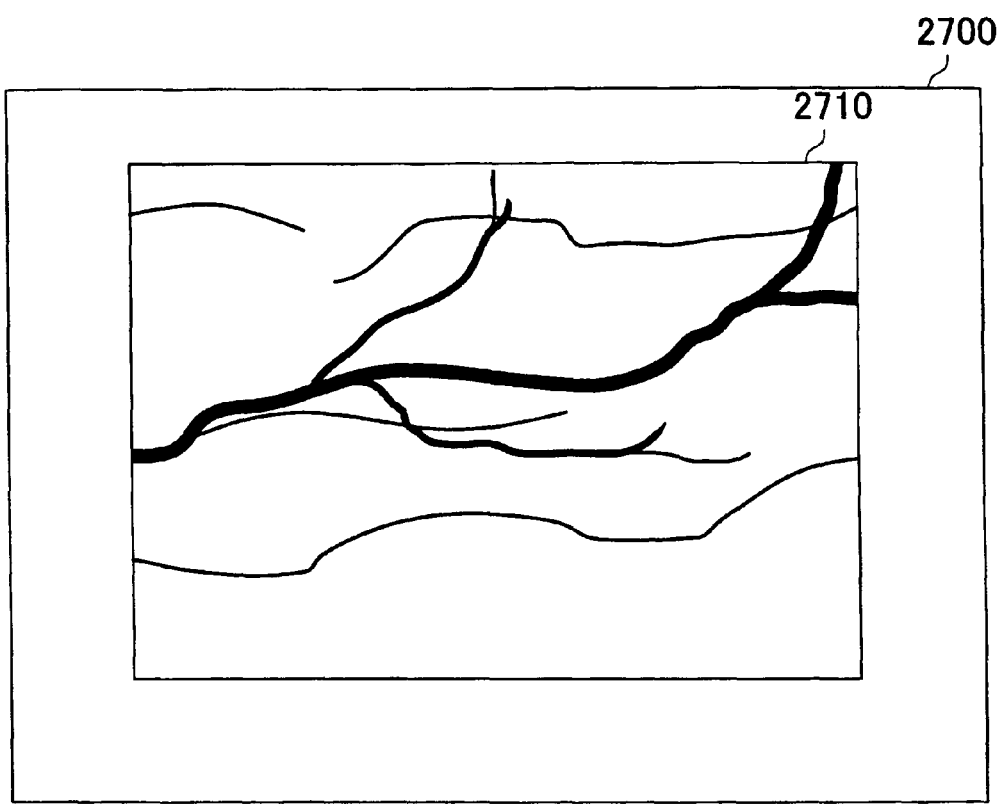
F I G. 15

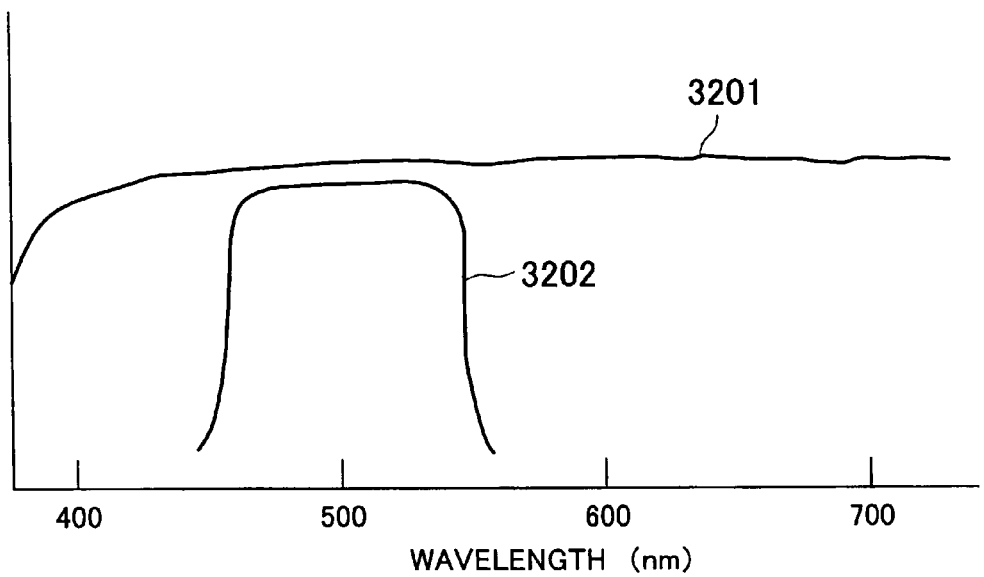
F I G . 17

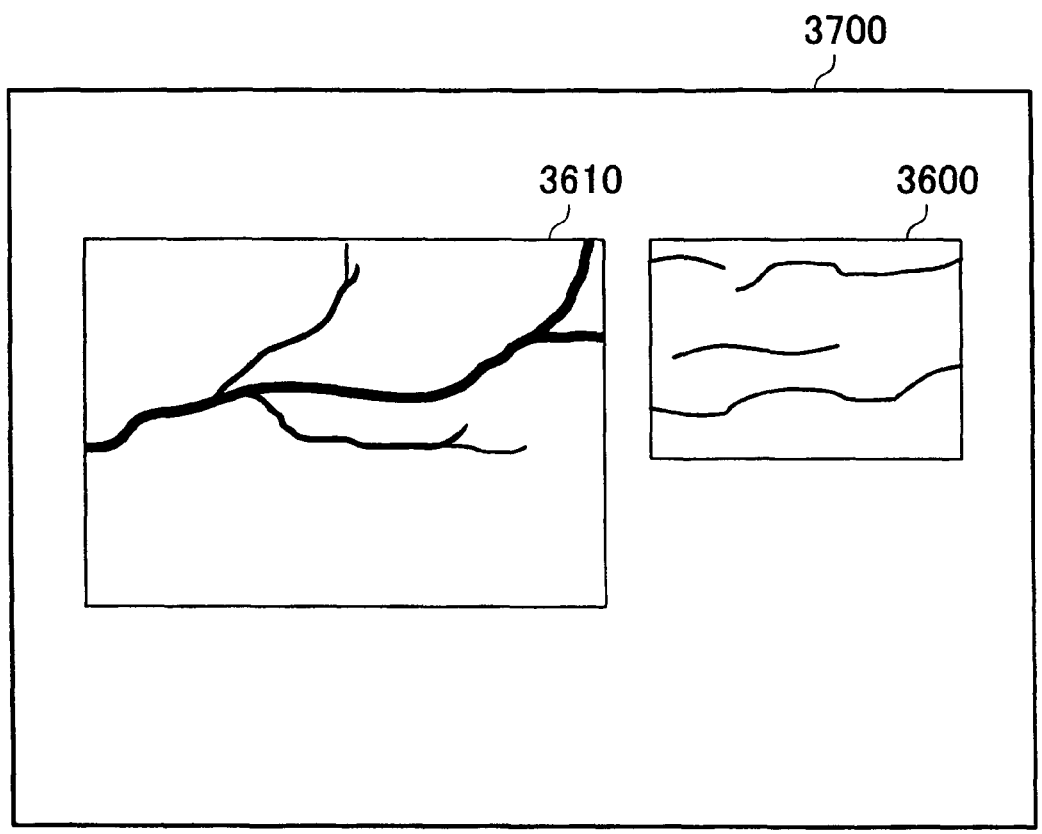
F I G . 22

IMAGE CAPTURING APPARATUS HAVING FIRST AND SECOND LIGHT RECEPTION SECTIONS, IMAGE CAPTURING METHOD, AND COMPUTER-READABLE MEDIUM

CROSS REFERENCE TO RELATED APPLICATION

The present application claims priority from Japanese Patent Applications Nos. 2008-095966 filed on Apr. 2, 2008, 2008-095983 filed on Apr. 2, 2008, and 2008-154516 filed on Jun. 12, 2008, the contents of which are incorporated herein by reference.

BACKGROUND

1. Technical Field

The present invention relates to an image capturing apparatus and an image capturing method, as well as to a computer-readable medium for storing therein a program.

2. Description of the Related Art

There is known a technology for sequentially switching irradiation of wideband light and narrowband light, to combine an image captured in the wideband light with an image captured in the narrowband light. Such a technology is disclosed in Japanese Patent Application Publication No. 2007-202589, for example. In the disclosed electronic endoscope, light irradiated from a light source is sequentially switched between wideband light and narrowband light using a rotation filter, and an image signal obtained when the wideband light is irradiated is combined with an image signal obtained when the narrowband light is irradiated.

There is also known a technology for controlling light emission from four light emitting diodes, which emit light of colors of red, green, a first blue, and a second blue, respectively, to select between visible wideband observation and narrowband observation. Such a technology is disclosed in Japanese Patent Application Publication No. 2006-166940. There is still further known a technology for alternately outputting white light and excitation light, to obtain an image captured in the white light and an image captured in the excitation light respectively. Such a technology is disclosed in Japanese Patent Application Publication No. 2004-236952, for example.

SUMMARY

With the above-disclosed technologies, it is impossible to control an image capturing cycle of a narrowband image and an image capturing cycle of a wideband image independently from each other. With the above-disclosed technologies, a narrowband image and a wideband image at the same timing cannot be obtained. With the above-disclosed technologies, a plurality of narrowband images of different bands from each other at the same timing cannot be obtained. In particular, with the technology disclosed in Japanese Patent Application Publication No. 2007-202589, since the wavelength band of irradiation light is sequentially switched by a rotation filter, light of a spectrum desired for observation cannot be irradiated at a desired timing.

In view of the above, according to an aspect of the innovations herein, provided is a position specifying system, a position specifying method, and a computer readable medium, which are capable of solving the above-stated problems. This object is achieved by combinations of features described in the independent claims. The dependent claims define further advantageous and concrete examples of the present invention According to an aspect of the innovations herein, provided is an image capturing apparatus including: a light irradiation section that irradiates a subject with a plurality of irradiation light rays having respectively different spectrum forms, at respectively different timings; and an image capturing section that captures a plurality of images of the subject irradiated with the plurality of irradiation light rays, at respectively different timings; where the light irradiation section irradiates the subject with an irradiation light ray resulting from combining a plurality of light rays having respectively different spectrum forms, at least at one timing.

A configuration is also possible in which the image capturing section includes: a first light reception section that receives light of a first wavelength region; and an image capturing control section, where the light irradiation section includes: a first light emission section that emits light of a first narrowband within the first wavelength region; a second light emission section that emits light of a second narrowband within the first wavelength region, the second narrowband being different from the first narrowband; and a light emission control section that controls the first light emission section and the second light emission section to periodically emit light, by controlling a light emission period or a light emission phase to be different between the first light emission section and the second light emission section, and the image capturing control section successively captures a) a narrowband image of light received by the first light reception section when one of the first light emission section and the second light emission section has emitted light, and b) a wideband image of light received by the first light reception section when both of the first light emission section and the second light emission section have emitted light.

A configuration is also possible in which the image capturing section further includes: a second light reception section that receives light of a second wavelength region that is different from the first wavelength region; a third light emission section that emits light of a third narrowband within the second wavelength region; and a fourth light emission section that emits light of a fourth narrowband within the second wavelength region, the fourth narrowband being different from the third narrowband; and the light emission control section controls the third light emission section and the fourth light emission section to periodically emit light, by controlling a light emission period or a light emission phase to be the same between the third light emission section and the first light emission section, and controlling a light emission period or a light emission phase to be the same between the fourth light emission section and the second light emission section, and the image capturing control section successively captures a) a narrowband image of light received by the first light reception section and the second light reception section when one of the first light emission section and the second light emission section and one of the third light emission section and the fourth light emission section have emitted light, and b) a wideband image of light received by the first light reception section and the second light reception section when the first light emission section through the fourth light emission section have emitted light.

the image capturing section further includes: a third light reception section that receives light of a third wavelength region that is different from the first wavelength region and the second wavelength region, and the light irradiation section further includes: a fifth light emission section that emits light of a fifth narrowband within the third wavelength region; and a sixth light emission section that emits light of a sixth narrowband within the third wavelength region, the sixth narrowband being different from the fifth narrowband, the light emission control section controls the fifth light emission section and the sixth light emission section to periodically emit light, by controlling a light emission period or a light emission phase to be the same between the fifth light emission section, the first light emission section, and the third light emission section, and controlling a light emission period or a light emission phase to be the same between the sixth light emission section, the second light emission section, and the fourth light emission section, and the image capturing control section successively captures a) a narrowband image of light received by the first light reception section through the third light reception section when one of the first light emission section and the second light emission section, one of the third light emission section and the fourth light emission section, and one of the fifth light emission section and the sixth light emission section have emitted light, and b) a wideband image of light received by the first reception section through the third light reception section when the first light emission section through the sixth light emission section have emitted light.

According to an aspect of the innovations herein, provided is an image capturing apparatus including: a first light reception section that receives light of a first wavelength region; a second light reception section that receives light of a second wavelength region that is different from the first wavelength region; a light emission control section that causes successive emission of a) wideband light of a band that includes the first wavelength region and the second wavelength region, and b) partial band light that mainly includes light of a part of the first wavelength region and a part of the second wavelength region; an image capturing control section that captures a) an image of light received by the first light reception section when the wideband light has been emitted, b) an image of light received by the second light reception section when the wideband light has been emitted, c) an image of light received by the first light reception section when the partial band light has been emitted, and d) an image of light received by the second light reception section when the partial band light has been emitted; and an image generating section that generates, based on the images captured by the image capturing control section, a) an image of light other than the partial band light within the first wavelength region, and b) an image of light other than the partial band light within the second wavelength region.

A configuration is also possible in which the light emission control section causes successive emission of the wideband light and narrowband light being light of a band spanning a part of the first wavelength region and a part of the second wavelength region, the image capturing control section captures a) a first wideband image of light received by the first light reception section when the wideband light has been emitted, b) a second wideband image of light received by the second light reception section when the wideband light has been emitted, c) a first narrowband image of light received by the first light reception section when the narrowband light has been emitted, and d) a second narrowband image of light received by the second light reception section when the narrowband light has been emitted, and the image generating section generates, based on an image of light captured by the image capturing control section, a third narrowband image of light other than the narrowband light within the first wavelength region and a fourth narrowband image of light other than the narrowband light within the second wavelength region.

The image capturing apparatus may further include a first light emission section that emits the wideband light; and a second light emission section that emits the narrowband light, where the light emission control section controls the first light emission section and the second light emission section to successively emit the wideband light and the narrowband light.

The image capturing apparatus may further include: a light emission section that emits the wideband light; and a filter section that filters light of a band other than the narrowband light, where the light emission control section controls the light emission section and the filter section to successively emit the wideband light and the narrowband light.

The image capturing apparatus may further include: a light emission section that emits the wideband light; and a filter section that filters narrowband light of a band spanning a part of the first wavelength region and a part of the second wavelength region, where the light emission control section controls the light emission section and the filter section to successively emit the wideband light and light of a band other than the narrowband light within the wideband light, the image capturing control section captures a) a first wideband image of light received by the first light reception section when the wideband light has been emitted, b) a second wideband image of light received by the second light reception section when the wideband light has been emitted, c) a third narrowband image of light received by the first light reception section when the light of the band other than the narrowband light has been emitted, and d) a fourth narrowband image of light received by the second light reception section when the light of the band other than the narrowband light has been emitted; and the image generating section generates, based on an image of light captured by the image capturing control section, a first narrowband image of the narrowband light within the first wavelength region and a second narrowband image of the narrowband light within the second wavelength region.

The image capturing apparatus may further include a wideband interpolation image generating section that generates a wideband interpolation image interpolating a plurality of wideband images, based on the wideband image and the narrowband image.

A configuration is also possible in which the wideband interpolation image generating section generates the wideband interpolation image, based on chromaticity information of the wideband image and brightness information of the narrowband image.

The image capturing apparatus may further include a motion detection section that detects relative motion between the image capturing section and the subject, where the wideband interpolation image generating section generates the wideband interpolation image, further based on motion information detected by the motion detection section.

The image capturing apparatus may further include a motion vector calculation section that calculates a first motion vector of the subject between a timing at which the wideband image is displayed and a timing at which the wideband interpolation image is displayed, based on the motion information detected by the motion detection section, where the wideband interpolation image generating section generates chromaticity information of pixels of the wideband interpolation image from chromaticity information of pixels included in the wideband image, based on the first motion vector calculated by the motion vector calculation section.

A configuration is also possible in which the motion vector calculation section calculates a second motion vector of the subject between a timing at which the narrowband image is displayed and a timing at which the wideband interpolation image is displayed, based on the motion information detected by the motion detection section, and the wideband interpolation image generating section generates brightness information of pixels of the wideband interpolation image from brightness information of pixels included in the narrowband image, based on the second motion vector calculated by the motion vector calculation section.

The image capturing apparatus may further include a narrowband interpolation image generating section that generates a narrowband interpolation image interpolating a plurality of narrowband images, based on the wideband image and the narrowband image.

A configuration is also possible in which the narrowband interpolation image generating section generates the narrowband interpolation image, based on brightness information of the wideband image and chromaticity information of the narrowband image.

The image capturing apparatus may further include a motion detection section that detects relative motion between the image capturing section and the subject, where the narrowband interpolation image generating section generates the narrowband interpolation image, further based on motion information detected by the motion detection section.

The image capturing apparatus may further include a motion vector calculation section that calculates a third motion vector of the subject between a timing at which the narrowband image is displayed and a timing at which the narrowband interpolation image is displayed, based on the motion information detected by the motion detection section, where the narrowband interpolation image generating section generates chromaticity information of pixels of the narrowband interpolation image from chromaticity information of pixels included in the narrowband image, based on the third motion vector calculated by the motion vector calculation section.

A configuration is also possible in which the motion vector calculation section calculates a fourth motion vector of the subject between a timing at which the wideband image is displayed and a timing at which the narrowband interpolation image is displayed, based on the motion information detected by the motion detection section, and the narrowband interpolation image generating section generates brightness information of pixels of the narrowband interpolation image from brightness information of pixels included in the wideband image, based on the fourth motion vector calculated by the motion vector calculation section.

A configuration is also possible in which the light irradiation section irradiates the subject with a plurality of irradiation light rays resulting from combining light rays having respectively different spectral forms in respectively different combinations, at respectively different timings, and the image capturing apparatus further comprises: an image processing section that generates an image of a preset spectrum, from the plurality of images.

A configuration is also possible in which the image capturing section includes an image capturing element for receiving light from the subject, and captures the plurality of images based on intensity of light received by the image capturing element, and the light irradiation section irradiates the subject with a plurality of irradiation light rays having respectively different spectral forms in a light reception wavelength region in which the image capturing element can receive light, at respectively different timings.

A configuration is also possible in which the light irradiation section includes: a light generating section that generates light rays having respectively different spectral forms; and an irradiation control section that irradiates, at respectively different timings, the subject with a plurality of irradiation light rays resulting from combining the light rays having respectively different spectral forms generated by the light generating section in respectively different combinations.

A configuration is also possible in which the light generating section includes a light emitting body that emits luminescence light, and the irradiation control section irradiates the subject with a plurality of irradiation light rays resulting from combining, in respectively different combinations, light rays having respectively different spectrum forms and including the luminescence light emitted from the light emitting body, at respectively different timings.

A configuration is also possible in which the light generating section further includes an excitation section that emits excitation light that is incident to the light emitting body to cause the light emitting body to emit the luminescence light, and the irradiation control section irradiates the subject with a) first irradiation light that includes the luminescence light emitted from the light emitting body and the excitation light emitted from the excitation section, and b) second irradiation light having a spectral form different from the first irradiation light, at respectively different timings.

A configuration is also possible in which the light generating section further includes a light emission section provided with the light emitting body; and the irradiation control section irradiates the subject with a) first irradiation light that includes the luminescence light emitted from the light emitting body and the excitation light emitted from the excitation section and passed through the light emission section, and b) second irradiation light having a spectral form different from the first irradiation light, at respectively different timings.

A configuration is also possible in which the light emitting body emits the luminescence light by means of first excitation light and second excitation light having a spectral form different from the first excitation light, the excitation section emits the first excitation light and the second excitation light respectively incident to the light emission section, and the irradiation control section irradiates the subject with a) first irradiation light that includes the luminescence light emitted from the light emitting body by means of the first excitation light and the first excitation light emitted from the excitation section and passed through the light emission section, and b) second irradiation light that includes the luminescence light emitted from the light emitting body by means of the second excitation light and the second excitation light emitted from the excitation section and passed through the light emission section, at respectively different timings.

A configuration is also possible in which the light emitting body emits luminescence light having a spectral form substantially the same as a spectral form of the luminescence light emitted by means of the first excitation light, by means of the second excitation light having a spectrum different from the first excitation light.

A configuration is also possible in which the image capturing element has, as the light reception wavelength region, a wavelength region of the luminescence light emitted by means of the first excitation light and a wavelength region of the first excitation light, and the excitation section emits the second excitation light of a wavelength region other than the light reception wavelength region of the image capturing element.

A configuration is also possible in which the image capturing section includes a plurality of image capturing elements having light reception wavelength regions different from each other, and the light emitting body emits luminescence light of a wavelength region that includes at least a part of the light reception wavelength region of each of a plurality of image capturing elements, by the first excitation light.

The image capturing apparatus may further include an insertion section, at least a tip of the insertion section being inserted to a narrow portion, the insertion section having an optical fiber for guiding the first excitation light and the second excitation light from the excitation section to the light emission section, where the light emission section is provided at the tip of the insertion section.

A configuration is also possible in which the plurality of image capturing elements are provided at the tip of the insertion section.

A configuration is also possible in which the light generating section includes a plurality of light emitting bodies for emitting light rays having respectively different spectral forms, and the irradiation control section controls the plurality of light emitting bodies to emit light in respectively different combinations at respectively different timings.

A configuration is also possible in which the plurality of light emitting bodies emit luminescence light rays having respectively different spectral forms, and the irradiation control section irradiates the subject with a plurality of irradiation light rays resulting from combining the luminescence light rays emitted from the plurality of light emitting bodies in respectively different combinations, at respectively different timings.

A configuration is also possible in which the plurality of light emitting bodies emit luminescence light rays having respectively different spectral forms, by means of excitation light rays in respectively different wavelength regions, the light generating section further includes an excitation section that emits the excitation light rays, and the irradiation control section controls the excitation section to emit the excitation light rays in respectively different combinations at respectively different timings, so as to irradiate the subject with the plurality of irradiation light rays resulting from combining the luminescence light rays emitted from the plurality of light emitting bodies in respectively different combinations, at respectively different timings.

A configuration is also possible in which the image capturing section includes a plurality of image capturing elements having light reception wavelength regions different from each other, and the light irradiation section irradiates the subject with the plurality of irradiation light rays having respectively different spectral forms in at least one of light reception wavelength regions, at respectively different timings.

A configuration is also possible in which the light irradiation section irradiates the subject with first irradiation light and second irradiation light at respectively different timings, a wavelength region of the second irradiation light in the light reception wavelength region corresponding to a partial wavelength region of a wavelength region of the first irradiation light, and the image processing section generates, as the image of the preset spectrum, an image of a wavelength region other than the wavelength region of the second irradiation light within the wavelength region of the first irradiation light, based on an image of the subject irradiated with the first irradiation light and an image of the subject irradiated with the second irradiation light.

A configuration is also possible in which the light irradiation section irradiates, at respectively different timings, the subject with the plurality of irradiation light rays, the wavelength regions respectively of which in the light reception wavelength region correspond to partial wavelength regions of the light reception wavelength region, and the image processing section generates, as the image of the preset spectrum, an image of a wavelength region wider than any of the wavelength regions of the plurality of irradiation light rays in the light reception wavelength region, based on the plurality of images.

A configuration is also possible in which the image processing section generates the image of the preset spectrum, based on the plurality of images and respective spectrums of the plurality of irradiation light rays.

A configuration is also possible in which the light irradiation section irradiates the subject with irradiation light rays in respectively different wavelength regions at respectively different timings, the irradiation light rays resulting from combining light rays in respectively different wavelength regions in respectively different combinations, and the image capturing section captures images of light rays from the subject irradiated with the irradiation light rays in respectively different wavelength regions, at respectively different timings, and the image processing section generates, as the image of the preset spectrum, an image of a specific wavelength region from the images captured by the image capturing section at the respectively different timings.

According to an aspect of the innovations herein, provided is an image capturing method including: irradiating a subject with a plurality of irradiation light rays having respectively different spectrum forms, at respectively different timings; and capturing a plurality of images of the subject irradiated with the plurality of irradiation light rays, at respectively different timings; where in the light irradiation, the subject is irradiated with an irradiation light ray resulting from combining a plurality of light rays having respectively different spectrum forms, at least at one timing.

According to an aspect of the innovations herein, provided is an image capturing method used in an image capturing apparatus, the image capturing apparatus including: a first light reception section that receives light of a first wavelength region; and a second light reception section that receives light of a second wavelength region that is different from the first wavelength region, the image capturing method including: causing successive emission of a) wideband light of a band that includes the first wavelength region and the second wavelength region, and b) partial band light that mainly includes a part of the first wavelength region and a part of the second wavelength region; capturing a) an image of light received by the first light reception section when the wideband light has been emitted, b) an image of light received by the second light reception section when the wideband light has been emitted, c) an image of light received by the first light reception section when the partial band light has been emitted, and d) an image of light received by the second light reception section when the partial band light has been emitted; and generating, based on the images captured by the image capturing control section, a) an image of light other than the partial band light within the first wavelength region, and b) an image of light other than the partial band light within the second wavelength region.

According to an aspect of the innovations herein, provided is a computer readable medium storing therein a program for an image capturing apparatus, the program causing a computer to function as: a light irradiation section that irradiates a subject with a plurality of irradiation light rays having respectively different spectrum forms, at respectively different timings; and an image capturing section that captures a plurality of images of the subject irradiated with the plurality of irradiation light rays, at respectively different timings; where the light irradiation section irradiates the subject with an irradiation light ray resulting from combining a plurality of light rays having respectively different spectrum forms, at least at one timing.

According to an aspect of the innovations herein, provided is a computer readable medium storing therein a program for an image capturing apparatus, the image capturing apparatus including: a first light reception section that receives light of a first wavelength region; and a second light reception section that receives light of a second wavelength region that is different from the first wavelength region, the program causing a computer to function as: a light emission control section that causes successive emission of a) wideband light of a band that includes the first wavelength region and the second wavelength region, and b) partial band light that mainly includes light of a part of the first wavelength region and a part of the second wavelength region; an image capturing control section that captures a) an image of light received by the first light reception section when the wideband light has been emitted, b) an image of light received by the second light reception section when the wideband light has been emitted, c) an image of light received by the first light reception section when the partial band light has been emitted, and d) an image of light received by the second light reception section when the partial band light has been emitted; and an image generating section that generates, based on the images captured by the image capturing control section, a) an image of light other than the partial band light within the first wavelength region, and b) an image of light other than the partial band light within the second wavelength region.

The summary of the invention does not necessarily describe all necessary features of the present invention. The present invention may also be a sub-combination of the features described above.

BRIEF DESCRIPTION OF THE DRAWINGS

FIG. 2 schematically shows an exemplary internal structure of a scope 100.

FIG. 9 shows an exemplary block configuration of an image capturing apparatus 2100 according to an embodiment.

FIG. 10 shows an exemplary spectrum of light emitted from the light emission section 2110.

FIG. 14 shows exemplary display processing performed by a display section 2150.

FIG. 15 shows different exemplary display processing performed by the display section 2150.

FIG. 17 shows an exemplary spectrum of light emitted from a first light emission section 3112 and a second light emission section 3114.

FIG. 22 shows exemplary display processing performed by the display section 3150.

DESCRIPTION OF EXEMPLARY EMBODIMENTS

The invention will now be described based on the preferred embodiments, which do not intend to limit the scope of the present invention, but exemplify the invention. All of the features and the combinations thereof described in the embodiment are not necessarily essential to the invention.

Figure 1:
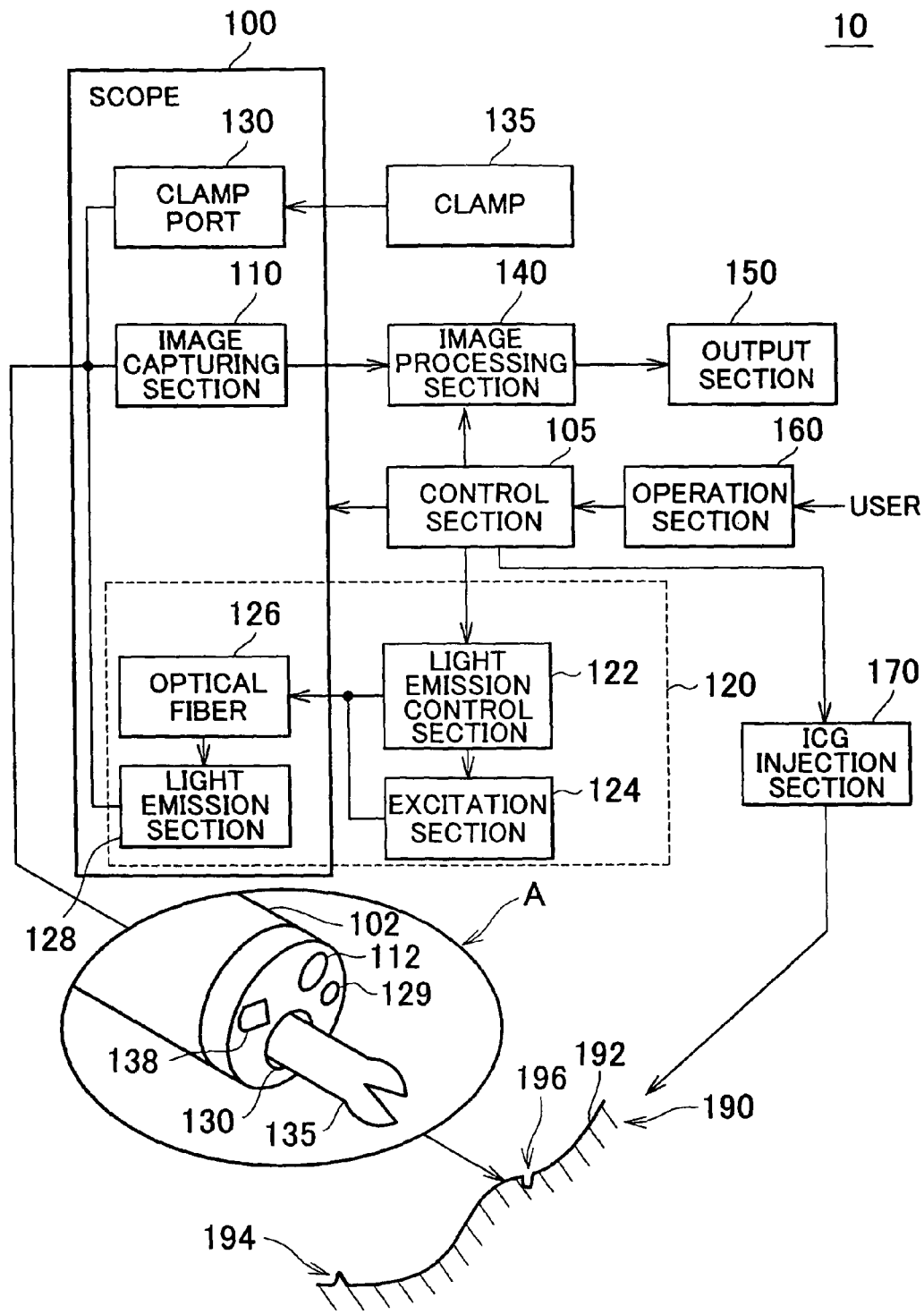
FIG. 1 shows an exemplary configuration of an endoscope system 10, together with a living body 190.

FIG. 1 shows an exemplary configuration of an endoscope system 10 according to an embodiment, together with a living body 190. The endoscope system 10 irradiates the living body 190 with irradiation light in a spectral form desired for an observation objective an observation target, and the like, to capture an image of the living body 190.

The endoscope system 10 includes a scope 100 being a part of an endoscope, a clamp 135, an image processing section 140, a control section 105, a light irradiation section 120, an operation section 160, an output section 150, and an ICG injection section 170. Note that in FIG. 1, Section A is an enlarged view of a tip 102 of the scope 100.

As detailed later with reference to the present embodiment, the endoscope system 10 can function as an image capturing system or an image processing system. In addition, the endoscope can function as an image capturing apparatus. For example, the image capturing section 110, the light irradiation section 120, and the image processing section 140 can function as an image capturing apparatus. In addition, the living body 190 may be an exemplary subject according to the present invention.

The scope 100, being an exemplary insertion section, includes an image capturing section 110 and a clamp port 130. The scope 100 incorporates therein an optical fiber 126 and a light emission section 128, as a part of the light irradiation section 120. At least a tip 102 of the scope 100 is inserted to a narrow portion. For example, the scope 100 may be inserted into the esophagus or the intestinal canal of a living organism.

The tip 102 of the scope 100 includes a nozzle 138, a lens 112 being a part of the image capturing section 110, and an emission port 129. Note that the optical fiber 126 and the light emission section 128 incorporated in the scope 100 function as a light emission section 120, in collaboration with an excitation section 124 and an irradiation control section 122 provided outside of the scope 100, for example. Note that the scope 100 may also incorporate therein the excitation section 124.

A clamp 135 is inserted to the clamp port 130, and the clamp port 130 guides the clamp 135 towards the tip 102. Note that the tip of the clamp 135 may have various forms. Various types of treatment tools for treating the living body 190 may be inserted to the clamp port 130 other than the clamp. The nozzle 138 guides water or air out to the living body 190.

The light emission section 128 includes a light emitting body that emits luminescence light by means of excitation light. The excitation section 124 emits excitation light for causing the light emitting body to emit luminescence light. The optical fiber 126 guides the excitation light emitted from the excitation section 124 towards the light emission section 128. The excitation light emitted from the excitation section 124 is incident to the light emission section 128, via the optical fiber 126.

The light emitting body is excited by the excitation light incident thereto via the optical fiber 126, to emit luminescence light. The luminescence light emitted from the light emission section 128 irradiates the living body 190 as irradiation light, after passing the emission port 129. Note that the luminescence light emitted from the light emitting body may include light of a visible light region. In addition, the irradiation light can function as irradiation light to irradiate the living body 190, when the image capturing section 110 captures an image of the living body 190.

Note that the luminescence light irradiates the living body 190, as a component of the irradiation light. For example, the excitation light emitted from the excitation section 124 is combined with the luminescence light, so that the combination of light irradiates the living body 190 as irradiation light. In addition, the light emitting body may emit luminescence light by means of excitation light of another wavelength region. In this case, as a result of emission of excitation light of the other wavelength region by the excitation section 124, the excitation light of the other wavelength region is combined with the luminescence light so that the combination of light irradiates the living body 190 as irradiation light.

In this way, the irradiation control section 122 emits irradiation light of various spectral forms from the emission port 129, as a result of controlling the wavelength region of the excitation light emitted from the excitation section 124. In addition, the irradiation control section 122 is able to emit irradiation light of various spectral forms from the emission port 129 at respectively different timings, as a result of controlling the light emission timing of the excitation light emitted from the excitation section 124.

Note that the excitation section 124 and the light emission section 128 can function as a light generating section that generates light rays having different spectral forms from each other. Then, the light irradiation section 120 can irradiate the living body 190 with irradiation light rays having respectively different spectral forms, which result from combining light rays having respectively different spectral forms in respectively different combinations, at respectively different timings. Note that the light irradiation section 120 desirably emits irradiation light rays having different spectral forms from each other at least in the wavelength region in which the image capturing section 110 has a spectral sensitivity.

The image capturing section 110 captures an image of the living body 190 within a living organism which the irradiation light irradiates. Note that an example of the living body 190 is membrane mucosa of a digestive organ of a living organism, such as membrane mucosa of the stomach or of the intestine.

The image capturing section 110 captures a plurality of images of the living body 190 irradiated with respective irradiation light rays having respectively different spectral forms, at respectively different timings. Specifically, the image capturing section 110 captures the plurality of images at respectively different timings, by means of light from the living body 190 irradiated with the irradiation light rays including luminescence light.

Note that the image capturing section 110 is able to capture an image of the living body 190, by means of reflection of luminescence light reflected by a surface 192 of the living body 190 or by an internal portion of the living body 190. Alternatively, the image capturing section 110 is able to capture an image of the living body 190, by means of scattering of the luminescence light by the living body 190.

The image processing section 140 processes the images obtained by the image capturing section 110. Specifically, the image processing section 140 generates an image of a preset spectrum, from the plurality of images captured by the image capturing section 110.

Here, the luminescence light is wideband light, and each type of excitation light is narrowband light of a wavelength region narrower than the luminescence light. For example, the excitation section 124 emits light in a wavelength bandwidth narrower than a preset value. For example, the excitation section 124 may emit excitation light having a wavelength bandwidth of about 10-20 nm. In addition, the wavelength region of one type of excitation light is out of spectral sensitivity of the image capturing section 110. In this case, if image capturing is performed by irradiating luminescence light resulting from the excitation light in the range outside the spectral sensitivity, the obtained image will be in accordance with the spectrum of the luminescence light.

In this case, the image processing section 140 subtract a) the image in accordance with the spectrum of the luminescence light, from b) the image obtained by irradiation of excitation light of a wavelength region within the spectral sensitivity of the image capturing section 110 as well as the luminescence light resulting from the excitation light. As a result, the image processing section 140 can generate an image in accordance with the spectrum of the excitation light within the range of the spectral sensitivity of the image capturing section 110, as an image of a preset spectrum. In this way, the image processing section 140 can generate, as images of a preset spectrum, the wideband image as well as the narrowband image.

When excitation light rays having respectively different wavelength regions are used to cause the light emitting body to emit luminescence light rays having respectively different spectral forms, the light irradiation section 120 can control the spectrum of light emitted from the light emission section 128, by controlling the wavelength region and the intensity of the excitation light. In addition, by causing a part of the excitation light of a narrowband to pass through the light emission section 128, the light irradiation section 120 is able to irradiate the living body 190 with irradiation light in a narrowband, as described above.

The image generated by the image processing section 140 is outputted to the output section 150. The output section 150 may be a display device for displaying an image generated by the image processing section 140. The output section 150 may display a wideband image combined with an image in which a narrowband image generated by the image processing section 140 is emphasized. In addition, the output section 150 may perform display by switching between a wideband image and an image in which a narrowband image is emphasized, at a display rate higher than a preset value.

Note that the light irradiation section 120 may sequentially switch the spectral form of the irradiation light. The image capturing section 110 may successively capture the image of the living body 190 in synchronization with the switching of the spectral form. Accordingly, the image processing section 140 can generate a moving image of the living body 190.

Note that the output section 150 may be a recorder that records an image generated by the image processing section 140, to a recording medium. For example, the output section 150 may record, into a recording medium, a combined image between an image in which a narrowband image is emphasized, and a wideband image. In addition, the output section 150 may record, into a recording medium, a moving image resulting from switching between an image in which a narrowband image is emphasized, and a wideband image, at a display rate higher than a preset value. The recording medium may be a nonvolatile recording medium. Examples of the recording medium are a magnetic recording medium, a semiconductor memory, etc. such as a hard disk.

As explained above, the endoscope system 10 is able to generate an image of the living body 190 by means of light of a preset spectrum from the living body 190. Here, examples of the wavelength region of the light of the preset spectrum are wavelength regions respectively: in the vicinity of 450 nm; in the vicinity of 500 nm; in the vicinity of 550 nm; and in the vicinity of 830 nm, and a wavelength region of a combination of them. In addition, the wavelength region of the light of the preset spectrum may have a narrowband of 10-20 nm.

When the wavelength region of the light of the preset spectrum is in the vicinity of 450 nm, the image processing section 140 can generate an image in which an image of a blood vessel near a surface of the living body 190, a pit near a surface of the intestinal canal, and so on, is emphasized. When the wavelength region of the light of the preset spectrum is in the vicinity of 500 nm, the image processing section 140 may generate an image in which concaves and convexes are emphasized. For example, the image processing section 140 may generate an image in which a concave 196 and a convex 194 are emphasized.

When the wavelength region of the light of the preset spectrum is in the vicinity of 550 nm, the image processing section 140 may generate an image in which the hemoglobin concentration is emphasized. For example, the image processing section 140 may generate an image in which a reddened part of the living body 190 and minute blood vessels are emphasized.

In addition, when the wavelength region of the light of the preset spectrum is in the vicinity of 600 nm, the image processing section 140 may generate an image in which the hypertrophy of the living body 190 is emphasized based on the fluorescence emitted from the living body 190 itself. In addition, when the wavelength region of the light of the preset spectrum is in the vicinity of 830 nm, the image processing section 140 may generate an image in which blood vessels deep in the living body 190 are emphasized.

Note that the image in which blood vessels deep in the living body 190 are emphasized can be obtained by injecting a luminescence substance such as indocyanine green (ICG). For example, The ICG injector 170 may injects, into the living body 190, indocyanine green (ICG) which is a luminescence substance, by injecting ICG into the blood vessels of the living body 190 by means of intravenous injection. ICG emits fluorescence of the wavelength region in the vicinity of 830 nm, by being excited by the excitation light of the wavelength region in the vicinity of 780 nm for example. The image capturing section 110 can capture an image of a blood vessel in the living body 190, by means of the luminescence light from ICG. Although the present embodiment uses ICG as a luminescence substance, other fluorescence substances than ICG can also be used as a luminescence substance.

Note that the luminescence light emitted from at least one of the light emitting body included in the light emission section 128 and the luminescence substance injected into the living body 190 is fluorescence and phosphor light. In addition to the above-described luminescence light by means of light luminescence, the luminescence light emitted from the light emitting body included in the light emission section 128 may also be luminescence light by means of at least one of electroluminescence, cathode luminescence by means of electronic beams, friction luminescence, thermal luminescence by means of heat, sonoluminscence by means of acoustic waves, and triboluminescence by means of a physical force. The excitation section 124 may cause a light emitting body to emit luminescence light, by supplying, as the excitation energy for exciting the light emitting body, energy in accordance with the excitation processing of the light emitting body, such as electric energy, friction energy, and thermal energy, other than optical energy.

The operation section 160 obtains an instruction from a user. An example of the user instruction is an instruction to specify an observation target or an observation objective. An example of the instruction is to emphasize the pit, the near-surface blood, the concave or the convex, and the blood at the depth, which are explained above.

When the operation section 160 has obtained a user instruction, the control section 105 instructs the irradiation control section 122 to cause the light irradiation section 120 to irradiate irradiation light of a spectral form in accordance with the user instruction. In response to the user instruction, the irradiation control section 122 controls the spectrum of the excitation light to be emitted from the excitation section 124, or the time period during which the excitation light is emitted. The control section 105 also controls the image capturing operation by the image capturing section 110, or the image processing by the image processing section 140, in response to a user instruction.

The operation section 160 also obtains, from a user, an instruction that includes control contents to control the scope 100. For example, the operation section 160 obtains, from a user, an instruction that includes a driving amount to drive the tip 102 of the scope 100. For example, the operation section 160 includes an angle control knob which a user will rotate for changing the angle of the tip 102 of the scope 100. The operation section 160 may obtain, from a user, an instruction that includes a rotation amount in which the angle control knob has been rotated by the user, as the instruction that includes a driving amount to drive the tip 102 of the scope 100.

The control section 105 controls the scope 100, based on an instruction obtained by the operation section 160 from a user.

For example, the control section 105 may drive the scope 100 based on the instruction. For example, the control section 105 may change the angle of the tip 102 of the scope 100, by the rotation amount corresponding to the instruction obtained by the operation section 160.

FIG. 2 schematically shows an exemplary internal structure of the scope 100. The image capturing section 110 includes a lens 112, a filter section 210, and a light reception section 200. The image capturing section 110 and the light emission section 128 are provided on the tip 102 of the scope 100.

The light emission section 128 includes a light emitting body. Specifically, the light emission section 128 includes a light emitting body that emits luminescence light. As described above, the light emitting body emits luminescence light by means of excitation light.

The excitation section 124 emits excitation light to the optical fiber 126. The optical fiber 126 functions as a light guiding path through which the incident excitation light is guided towards the light emission section 128. In this way, the excitation section 124 emits excitation light incident to the light emitting body, to cause the light emitting body to emit luminescence light.

Note that the light emission section 128 transmits a part of the excitation light. The part of the excitation light transmitted through the light emission section 128 irradiates the living body 190. The excitation light of a narrowband that has been emitted from the excitation section 124 and then is transmitted through the light emission section 128 will be used as light for generating an image of a preset spectrum by a narrowband light.

For example, the light emitting body included in the light emission section 128 emits luminescence light, by means of first excitation light, and second excitation light that has a spectral form different from the first excitation light. For example, the light emitting body included in the light emission section 128 emits luminescence light rays having substantially the same spectral forms as each other, by being excited by the first excitation light and the second excitation light that has a spectral form different from the first excitation light.

The excitation section 124 is able to emit the first excitation light and the second excitation light to be respectively incident to the light emission section 128. For example, the irradiation control section 122 causes the excitation section 124 to emit the first excitation light and the second excitation light at respectively different timings. The first excitation light and the second excitation light emitted from the excitation section 124 are guided through the optical fiber 126 towards the light emission section 128.

Here, the light emission section 128 transmits a part of the first excitation light and a part of the second excitation light. For this reason, at the timing when the excitation section 124 has emitted the first excitation light, the living body 190 is irradiated with the first irradiation light, which includes the luminescence light emitted from the light emitting body by means of the first excitation light and the first excitation light having emitted from the excitation section 124 and then transmitted through the light emission section 128. At the timing when the excitation section 124 has emitted the second excitation light, the living body 190 is irradiated with the second irradiation light, which includes the luminescence light emitted from the light emitting body by means of the second excitation light and the second excitation light having emitted from the excitation section 124 and then passed through the light emission section 128. In this way, the irradiation control section 122 is able to irradiate the living body 190 with the first irradiation light and the second irradiation light having different spectral forms from each other, at respectively different timings.

As explained so far, the irradiation control section 122 is able to irradiate the living body 190 with irradiation light resulting from combining, in different combinations, light rays having different spectral forms from each other. Specifically, the irradiation control section 122 can irradiate the living body 190 with first irradiation light and second irradiation light having different spectral forms from each other, at respectively different timings.

In this way, the irradiation control section 122 is able to irradiate the living body 190 with first irradiation light and second irradiation light at respectively different timings, where the first irradiation light includes luminescence light emitted from the light emitting body and excitation light emitted from the excitation section 124, and the second irradiation light has a different spectral form from the first irradiation light. In the above-described example, each of the first irradiation light and the second irradiation light includes luminescence light emitted from the light emitting body. However, at least one of the first irradiation light and the second irradiation light may include luminescence light. For example, the first irradiation light includes luminescence light emitted from the light emitting body and excitation light emitted from the excitation section 124, and the second irradiation light may not include luminescence light.

Note that, by means of second excitation light having a different wavelength region from first excitation light, the light emitting body may emit luminescence light having a spectral form different from the spectral form of the luminescence light emitted by means of the first excitation light. The irradiation control section 122 may irradiate the living body 190 with irradiation light rays having different spectral forms from each other, by controlling the light emission timings of the first excitation light and the second excitation light in the excitation section 124.

The excitation section 124 may include a laser diode, to emit laser light as excitation light, which is to be incident to the optical fiber 126. The light emitting body may be a fluorescence body that emits luminescence light by being excited by the laser light emitted from the excitation section 124 as described above. Note that the laser light may be an example of coherent light. The excitation section 124 may emit the first excitation light and the second excitation light, which are respectively coherent light.

The light emission section 128 may have a light emitting diode as an example of the light emitting body. For example, the light emission section 128 may include a plurality of light emitting diodes emitting light of different spectral forms from each other. The irradiation control section 122 may irradiate the living body 190 with irradiation light resulting from combining light rays of different spectral forms from each other at respectively different timings, by controlling the light emission timing of the plurality of light emitting diodes. In this case, the excitation section 124 may supply electric energy to the light emission section 128. The scope diameter of the scope 100 can also be reduced in this configuration, too.

Note that the light emission section 128 may include a plurality of light emitting bodies capable of emitting light rays having different spectral forms from each other. The irradiation control section 122 may irradiate the living body 190 with irradiation light rays having different spectral forms from each other at respectively different timings, by emitting the plurality of light emitting bodies in different combinations at respectively different timings.

For example, the light emission section 128 may include a plurality of light emitting bodies capable of emitting different luminescence light rays having different spectral forms from each other. The plurality of light emitting bodies may emit luminescence light rays having different spectral forms from each other, by means of excitation light rays in different wavelength regions from each other. The excitation section 124 may emit excitation light rays in different wavelength regions from each other, which are to excite the plurality of light emitting bodies respectively. In this case, the irradiation control section 122 may irradiate the living body 190 with irradiation light rays resulting from combining the luminescence light rays emitted from the plurality of light emitting bodies in different combinations, at respectively different timings, by causing the excitation section 124 to emit excitation light rays in different wavelength regions from each other at different timings in different combinations respectively. In this way, the irradiation control section 122 can irradiate the living body 190 with irradiation light rays resulting from combining luminescence light rays emitted from a plurality of light emitting bodies in different combinations from each other, at respectively different timings.

As described above, when the image capturing section 110 captures an image of the living body 190 with luminescence light from ICG, the excitation section 124 may emit excitation light of a wavelength region within which ICG can be excited. For example, the excitation section 124 emits excitation light of a wavelength region in the vicinity of 780 nm. The excitation light in the wavelength region in the vicinity of 780 nm emitted from the excitation section 124 irradiates the living body 190 after passed through the light emission section 128.

In this way, the light irradiation section 120 may include various light sources such as a laser diode, a light emitting diode, and a fluorescent body. The light irradiation section 120 is capable of independently generating irradiation light rays having different spectral forms from each other, by combining light rays independently emitted from these light sources, in various combinations.

The lens 112 forms an image from the light from the living body 190, onto the light reception section 200. The filter section 210 is a color filter, in which arranged are a plurality of color filter elements selectively transmitting light rays of different wavelength regions from each other on substantially the same plane in matrix formation. The configuration of the filter section 210 is detailed later with reference to FIG. 3.

As explained with reference to FIG. 3, an electric signal representing the amount of light received by the image capturing elements included in the light reception section 200 is supplied to the image processing section 140. In this way, the image capturing section 110 includes a plurality of image capturing elements for receiving light from the living body 190, and can generate an image signal according to the intensity of light received by each image capturing element. Note that the image capturing section 110 may generate an image signal representing an image captured at respective timings, by exposing the image capturing elements, in each of a period during which the living body 190 is irradiated with first irradiation light from the light irradiation section 120 and a period during which the living body 190 is irradiated with second irradiation light from the light irradiation section 120.

Figure 3:
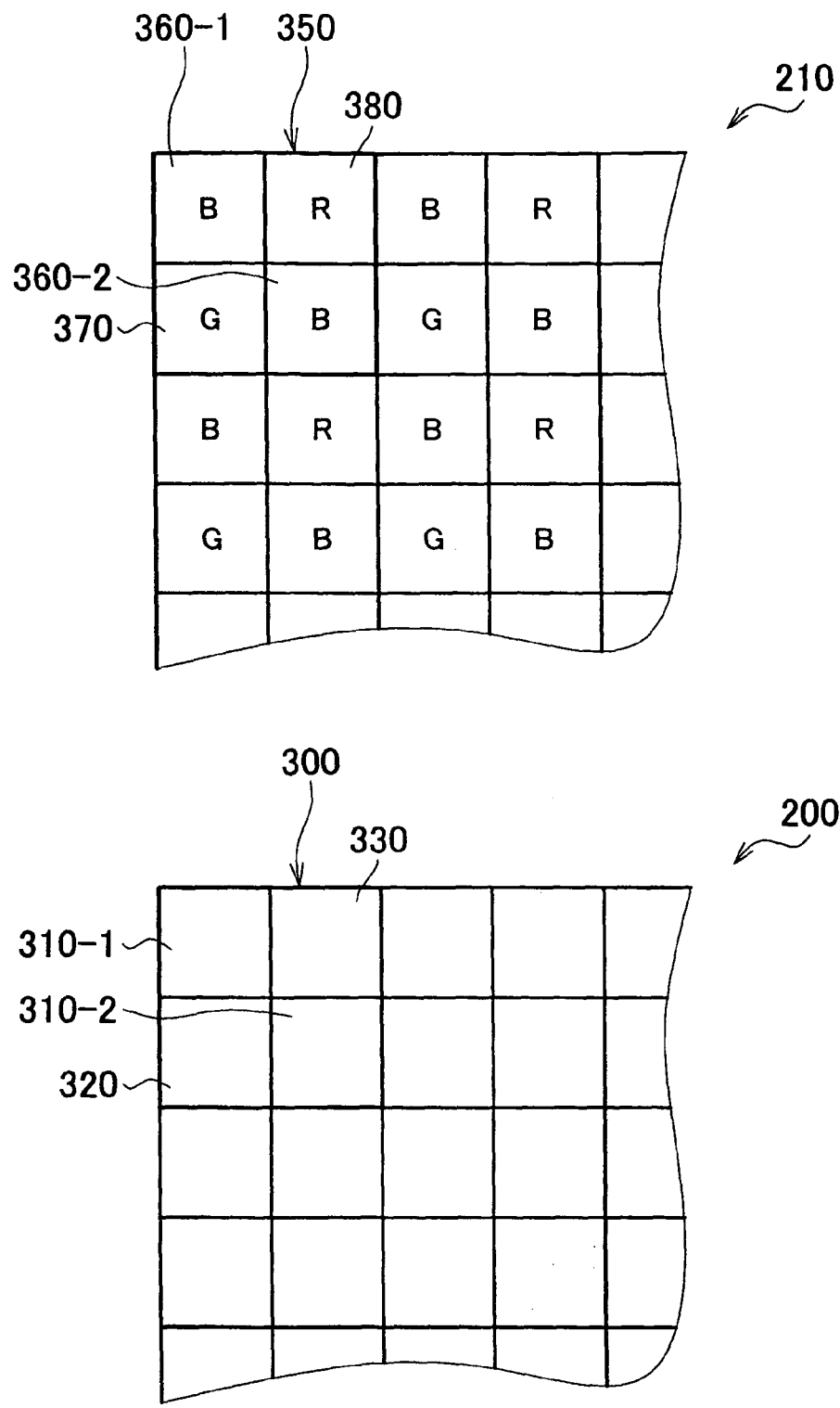
FIG. 3 shows an exemplary configuration of a filter section 210 and a light reception section 200.

FIG. 3 shows an exemplary filter arrangement of the filter section 210 as well as an exemplary image capturing element arrangement of the light reception section 200. The filter section 210 includes a B filter 360-1 and a B filter 360-2 that selectively transmit blue component light, a G filter 370 that selectively transmits green component light, and an R filter 380 that selectively transmits red component light. In the following explanation, the B filter 360-1 and the B filter 360-2 are occasionally collectively referred to as "B filter 360."

The filter unit 350 is formed by the B filter 360, the G filter 370, and the R filter 380. The filter section 210 is formed by a two-dimensional arrangement of filter units similar to the filter unit 350 are arranged.

The light reception section 200 includes a B image capturing element 310-1 and a B image capturing element 310-2 for receiving light of blue component light, a G image capturing element 320 for receiving green component light, and an R image capturing element 330 for receiving red component light. In the following explanation, the B image capturing element 310-1 and the B image capturing element 310-2 are occasionally collectively referred to as "B image capturing element 310."

The image capturing element unit 300 is formed by the B image capturing element 310, the G image capturing element 320, and the R image capturing element 330. The light reception section 200 is formed by a plurality of image capturing element units arranged two dimensionally just as the filter units 300.

Here, the B image capturing element 310-1, the B image capturing element 310-2, the G image capturing element 320, and the R image capturing element 330 are aligned with the B filter 360-1, the B filter 360-2, the G filter 370, and the R filter 380, respectively. By doing so, the B image capturing element 310-1, the B image capturing element 310-2, the G image capturing element 320, and the R image capturing element 330 are able to respectively receive light passed through the B filter 360-1, light passed through the B filter 360-2, light passed through the G filter 370, and light passed through the R filter 380.

As the present drawing shows, the B image capturing element 310 is arranged at a surface density higher than the G image capturing element 320 and the R image capturing element 330. Accordingly, the image capturing section 110 can capture an image of the living body 190 at higher resolution with shorter wavelength light. By arranging so, the image capturing section 110 may occasionally capture the minute structure of a surface layer of the living body 190 with relatively high resolution.

In this way, the light reception section 200 is provided with a plurality of image capturing elements corresponding to a plurality of filters transmitting different wavelength regions from each other. Each of the plurality of image capturing elements receives light that a corresponding one of the plurality of filters has selectively transmitted. In this way, the image capturing section 110 includes a plurality of image capturing elements that receive light of different light reception wavelength regions from each other.

Note that the filter section 210 transmits reflection light resulting from reflection of irradiation light irradiated from the light irradiation section 120 by the living body 190, and scattered light resulting from scatter of irradiation light by the living body 190. It is desirable that the filter section 210 transmit luminescence light emitted from ICG and does not transmit excitation light for exciting the ICG.

Figure 4:
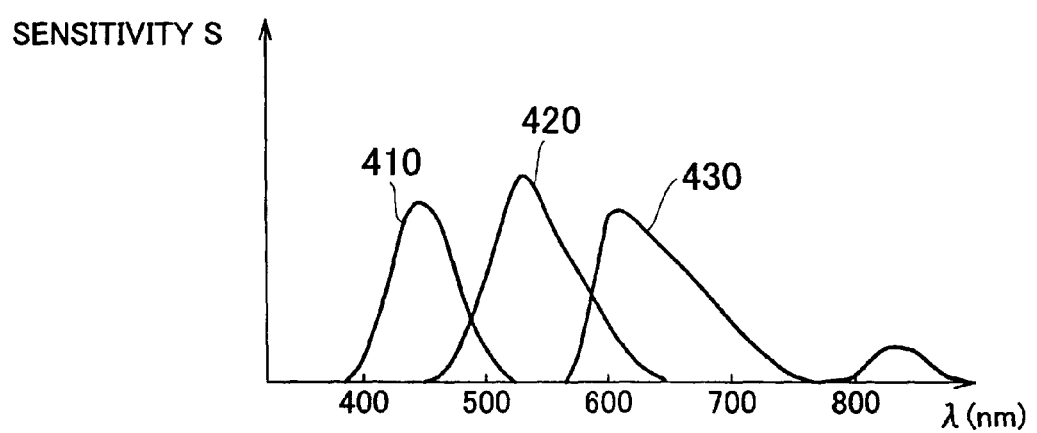
FIG. 4 shows a spectral sensitivity characteristic of an image capturing section 110.

FIG. 4 shows an exemplary spectral sensitivity characteristic of the image capturing section 110. The spectral sensitivity characteristic of each color component in the image capturing section 110 is determined by the spectral transmission rate of each filter in the filter section 210 as well as the spectral sensitivity of each image capturing element in the light reception section 200. The spectral sensitivity characteristic of the blue wavelength region in the B image capturing element 310 is represented by the line 410, the spectral sensitivity characteristic of the green wavelength region in the G image capturing element 320 is represented by the line 420, and the spectral sensitivity characteristic of the red wavelength region 330 is represented by the line 430.

As shown in the drawing, the image capturing section 110 has a spectral sensitivity to light in the wavelength region from the vicinity of 400 nm to the vicinity of 510 nm, in the short wavelength region in the visible light region, due to the B filter 360 and the B image capturing element 310. The B image capturing element 310 is able to receive light of the wavelength region, and so this wavelength region is referred to as "a light reception wavelength region of the B image capturing element 310."

The image capturing section 110 has a spectral sensitivity to light in the wavelength region from the vicinity of 470 nm to the vicinity of 620 nm, in the middle wavelength region in the visible light region, due to the G filter 370 and the G image capturing element 320. The G image capturing element 320 is able to receive light of the wavelength region, and so this wavelength region is referred to as "a light reception wavelength region of the G image capturing element 320."

In addition, the image capturing section 110 has a spectral sensitivity to light in the wavelength region from the vicinity of 580 nm to the vicinity of 740 nm, and in the wavelength region from the vicinity of 810 nm to the vicinity of 840 nm, in the long wavelength region in the visible light region, due to the R filter 380 and the R image capturing element 330. The R image capturing element 330 is able to receive light of the wavelength regions, and so the wavelength regions are referred to as "light reception wavelength regions of the R image capturing element 330."

Note that the R filter 380 cuts off the light in the wavelength region in the vicinity of 780 nm. Due to this, excitation light in the wavelength region in the vicinity of 780 nm for exciting ICG is prevented from being incident to the R image capturing element 330. On the other hand, the R filter 380 transmits light in the wavelength region in the vicinity of 830 nm. Due to this, the image capturing section 110 can adequately capture an image of the living body 190 by means of the luminescence light from ICG.

Figure 5:
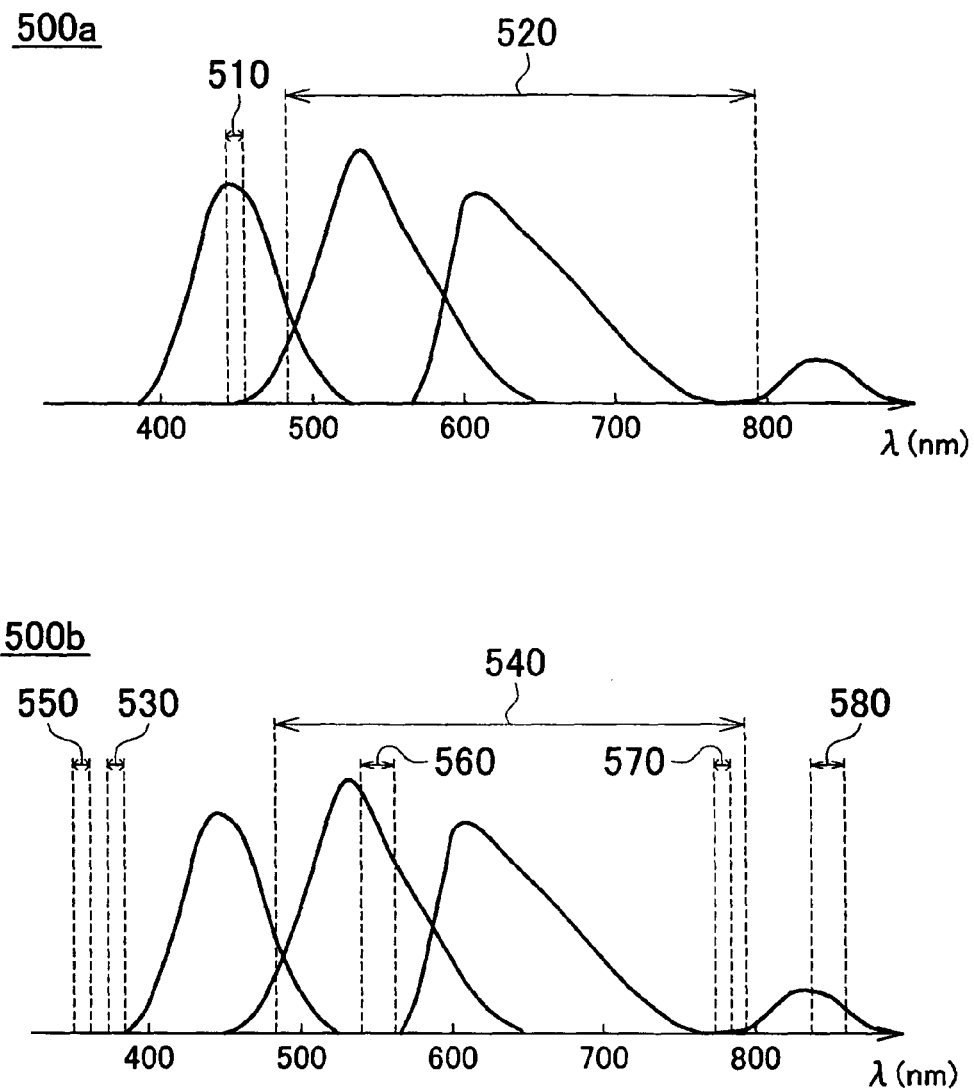
FIG. 5 shows an exemplary wavelength pattern of irradiation light.

FIG. 5 shows an exemplary wavelength pattern of irradiation light, together with the spectral sensitivity characteristic in the image capturing section 110. The light irradiation section 120 irradiates irradiation light obtained by combining the light rays having different spectral forms from each other in a combining pattern 500a at a timing different from irradiation of irradiation light obtained by combining the light rays having the different spectral forms from each other in a combining pattern 500b.

When the living body 190 is irradiated with irradiation light by the combining pattern 500a, the excitation section 124 emits excitation light of the wavelength region 510 being light of the light reception wavelength region of the B image capturing element 310. Here, the wavelength region 510 is in the vicinity of 450 nm, and is not included in any of the light reception wavelength region of the G image capturing element 320 and the light reception wavelength region of the R image capturing element 330. Note that the excitation light of the wavelength region 510 can be exemplary first excitation light in the present invention. The light reception wavelength region of the B image capturing element 310 includes the wavelength region of the luminescence light emitted by means of the excitation light of the wavelength region 510 and the wavelength region 510.

Here, the light emitting body emits luminescence light of the wavelength region 520 that incorporates therein the light reception wavelength region of the B image capturing element 310, the light reception wavelength region of the G image capturing element 320, and the light reception wavelength region of the R image capturing element 330, by means of the excitation light of the wavelength region 510. In this way, the light emitting body emits luminescence light including at least a part of the light reception wavelength region of the B image capturing element 310, the light reception wavelength region of the G image capturing element 320, and the light reception wavelength region of the R image capturing element 330, by means of the excitation light of the wavelength region 510. Accordingly, the light irradiation section 120 is able to irradiate the living body 190 with irradiation light resulting from combining the excitation light of the wavelength region 510 and the luminescence light of the wavelength region 520.

When the living body 190 is irradiated with irradiation light by the combining pattern 500b, the excitation section 124 emits the excitation light of the wavelength region 530, the excitation light of the wavelength region 550, and the excitation light of the wavelength region 570, at substantially the same timing. Here, the wavelength region 530 is in the vicinity of 390 nm, and the wavelength region 550 is in the vicinity of 370 nm. In addition, none of the wavelength region 530 and the wavelength region 550 is included in any of the light reception wavelength region of the B image capturing element 310, the light reception wavelength region of the G image capturing element 320, and the light reception wavelength region of the R image capturing element 330.

In addition, the wavelength region 570 is in the vicinity of 780 nm. The excitation light in this wavelength region 570 excites ICG as described above. The light of this wavelength region is not included in any of the light reception wavelength regions of the B image capturing element 310, the G image capturing element 320, and the R image capturing element 330.

The light emitting body emits luminescence light of the wavelength region 540 that incorporates therein the light reception wavelength region of the B image capturing element 310, the light reception wavelength region of the G image capturing element 320, and the light reception wavelength region of the R image capturing element 330, by means of the excitation light in the vicinity of 390 nm. Here, the wavelength region 520 and the wavelength region 540 may be substantially the same wavelength region as each other. In addition, the spectral form of the luminescence light by means of the excitation light in the vicinity of 390 nm may be substantially the same as the spectral form of the luminescence light by means of the excitation light in the vicinity of 450 nm. The intensity of the luminescence light by means of the excitation light in the vicinity of 390 nm may be different from the intensity of the luminescence light by means of the excitation light in the vicinity of 450 nm. As detailed later, the image processing section 140 may process the signal from each image capturing element according to the spectrum of the luminescence light.

In addition, the light emitting body emits the luminescence light of the wavelength region 560 included in the light reception wavelength region of the G image capturing element 320, by means of the excitation light in the vicinity of 370 nm. Here, the wavelength region 560 is not included in any of the light reception wavelength region of the B image capturing element 310 and the light reception wavelength region of the R image capturing element 330.

Note that the excitation light of the wavelength region 530 may be exemplary second excitation light in the present invention. The excitation section 124 emits the excitation light of the wavelength region 530 which is the light of the wavelength region other than the light reception wavelength region of the B image capturing element 310, at a timing different from the excitation light of the wavelength region 510. As described above, the light irradiation section 120 is able to irradiate the living body 190 with irradiation light rays having different spectral forms from each other, in the light reception wavelength region in which the image capturing element can receive light, at respectively different timings. For example, the light irradiation section 120 irradiates the living body 190 with irradiation light rays having different spectral forms from each other, at least in the light reception wavelength region of the B image capturing element 310, at respectively different timings.

Note that the wavelength of the second irradiation light is a partial wavelength region of the first irradiation light in the light reception wavelength region of the B image capturing element 310. In this case, the image processing section 140 is able to generate an image of a wavelength region outside the wavelength region of the second irradiation light within the wavelength region of the first irradiation light, as an image of a preset spectrum, based on the image of the living body 190 irradiated with the first irradiation light and the image of the living body 190 irradiated with the second irradiation light.

For example, the image processing section 140 is able to generate an image of a preset spectrum, by subtracting the image of the living body 190 irradiated with the second irradiation light, from the image of the living body 190 irradiated with the first irradiation light, by assigning weights taking into consideration the spectrum of the first irradiation light and the spectrum of the second irradiation light.

In the example of the present drawing, the image processing section 140 is able to generate an image of the wavelength region 510, and an image of a wavelength region in the vicinity of 500 nm. Here, the image of the wavelength region in the vicinity of 500 nm is an image corresponding to the light intensity of the narrowband of about the wavelength bandwidth of 20 nm in the vicinity of 500 nm. In this way, by performing spectral image capturing using image capturing elements respectively having sensitivity to different wavelength regions from each other, the image processing section 140 may occasionally generate an image of a preset spectrum of a narrowband. As described above, the image processing section 140 is able to generate an image of a preset spectrum, based on a plurality of images captured by the image capturing section 110 as well as respective spectrums of the first irradiation light and the second irradiation light.

In addition, the image processing section 140 is also able to generate, as an image of a preset spectrum, an image of a wavelength region wider than any irradiation light wavelength region in the light reception wavelength region, based on the plurality of images captured by the image capturing section 110. Specific examples of image processing performed by the image processing section 140 are detailed later with reference to FIG. 6.

Figure 6:
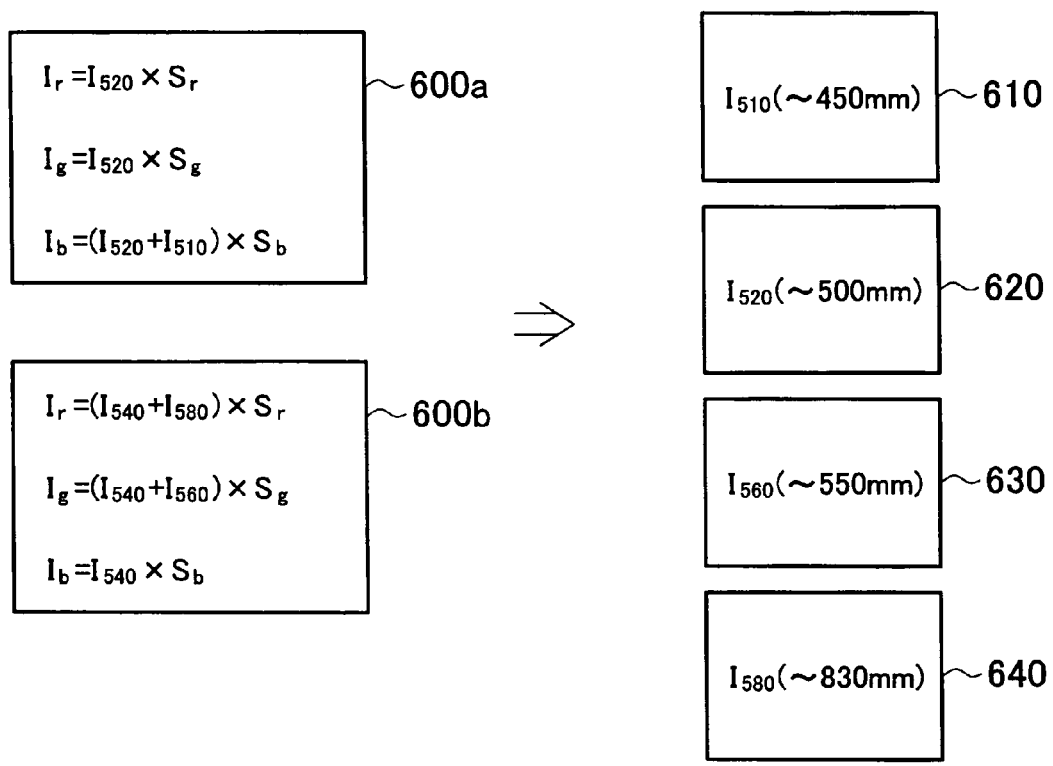
FIG. 6 shows exemplary image processing in an image processing section 140.

FIG. 6 shows exemplary image processing in an image processing section 140. The image 600a represents an image obtained by the image capturing section 110 capturing an image of the living body 190 irradiated with the irradiation light in the combining pattern 500a. The image 600b represents an image obtained by the image capturing section 110 capturing an image of the living body 190 irradiated with the irradiation light in the combining pattern 500b.

In the following description, the light intensity is represented as "I" with subscription according to the wavelength region of its light. For example, the intensity of the light of the wavelength region 510 from among the light directed to the image capturing section 110 from the living body 190 is referred to as "I510."

Moreover, the sensitivity of each image capturing element is represented as superscription according to its color component. For example, the sensitivity of the R image capturing element 330 is represented as "Ir." Additionally, when the spectral sensitivity by the R filter 380 and the R image capturing element 330 is represented as "Sr," "Ir" represents an integral value resulting from integrating, with respect to a wavelength, the value obtained by multiplying the light intensity "I" of the wavelength dependency from the living body 190 with Sr. The following description adopts multiplication representation instead of using the integral sign, for simplifying the explanation.

When the irradiation light in the combining pattern 500a is irradiated, IR=I520×Sr. Then, the luminance signal of R component of the image 600a will have a value according to "Ir." Although, in reality, the luminance signal of R component changes according to the exposure period in the image capturing section 110, the following explanation uses the luminance signal in the form of a standardized value with respect to the exposure period to facilitate the explanation.

Likewise, when the spectral sensitivity by the G filter 370 and the G image capturing element 320 is "Sg," the luminance signal of G component of the image 600a is a value corresponding to Ig(=I520×Sg). Likewise, when the spectral sensitivity by the B filter 360 and the B image capturing element 310 is "Sb," the luminance signal of B component of the image 600a is a value corresponding to Ib(=(I520+I510)×Sb).

Likewise, the luminance signal of R component of the image 600b is a value corresponding to Ir(=(I540+I580)×Sr). The luminance signal of G component of the image 600b is a value corresponding to Ig(=(I540×I560)×Sg). The luminance signal of B component of the image 600b will be a value corresponding to Ib(=I540×Sb).

The image processing section 140 generates a surface emphasized image 610, a concave/convex emphasized image 620, a hemoglobin emphasized image 630, and a depth blood vessel emphasized image 640, based on each color image signal of each of the image 600a and the image 600b. Note that the surface emphasized image 610, the concave/convex emphasized image 620, the hemoglobin emphasized image 630, and the depth blood vessel emphasized image 640 are respectively an exemplary image of a preset spectrum.

Specifically, the image processing section 140 can generate a surface emphasized image 610 having a luminance signal according to the sensitivity I510 in the wavelength region 510 in the vicinity of 450 nm. For example, the image processing section 140 is able to generate the surface emphasized image 610, based on the B signal of the captured image 600a, the B signal of the captured image 600b, I520, and I540. Note that I520 and I540 can be specified based on the spectrum emitted from the light emitting body according to the wavelength region of the excitation light and the intensity of the excitation light, as well as the wavelength region and the intensity of the excitation light emitted from the excitation section 124.

Likewise, the image processing section 140 is able to generate a concave/convex emphasized image 620 having a luminance signal according to the sensitivity I520 in the wavelength region where the wavelength region 520 overlaps with the light reception wavelength region of the B image capturing element 310, from the B signal of the image 600a and the image 600b. In addition, the image processing section 140 is able to generate a hemoglobin emphasized image 630 having a luminance signal according to the sensitivity I560 of the wavelength region 560 in the vicinity of 550 nm, from the G signal of the image 600a and the image 600b. In addition, the image processing section 140 is able to generate a depth blood vessel image 640 having a luminance signal according to the sensitivity I580 of the wavelength region 580 in the vicinity of 830 nm, from the R signal of the image 600a and the image 600b.

Also, the image processing section 140 is able to generate an image having a luminance signal according to the sensitivity I520 of the region where the wavelength region 520 overlaps with the light reception wavelength region of the G image capturing element 320, from the G signal of the image 600a and the image 600b. In addition, the image processing section 140 is able to generate an image having a luminance signal according to the light intensity I520 of the wavelength region where the wavelength region 520 overlaps with the light reception wavelength region of the R image capturing element 330, from the R signal of the image 600a and the image 600b.

Then, the image processing section 140 is able to generate an image according to its observation objective, by combining the luminance signals of respective colors in the plurality of generated images, by assigning preset weights thereto. For example, the image processing section 140 is able to generate a white light image expected to be obtained when the living body 190 is irradiated with substantially white colored light, based on the luminance signals of the respective colors in the plurality of images as well as the spectrum of the luminescence light emitted from the light emitting body or the living body 190.

Note that the image processing section 140 can also generate, as the white light image, an image captured by the image capturing section 110 while the excitation section 124 is emitting only the excitation light of the wavelength region 530. In this case, the image processing section 140 may correct the image captured by the image capturing section 110, according to the spectrum of the luminescence light by means of the excitation light of the wavelength region 530.

In addition, the image processing section 140 may generate, as an image of a preset spectrum, an image resulting from combining the white light image with at least one of the surface emphasized image 610, the concave/convex emphasized image 620, the hemoglobin emphasized image 630, and the depth blood vessel emphasized image 640. Therefore, the image processing section 140 can generate an image suitable for an observation objective.

Figure 7:
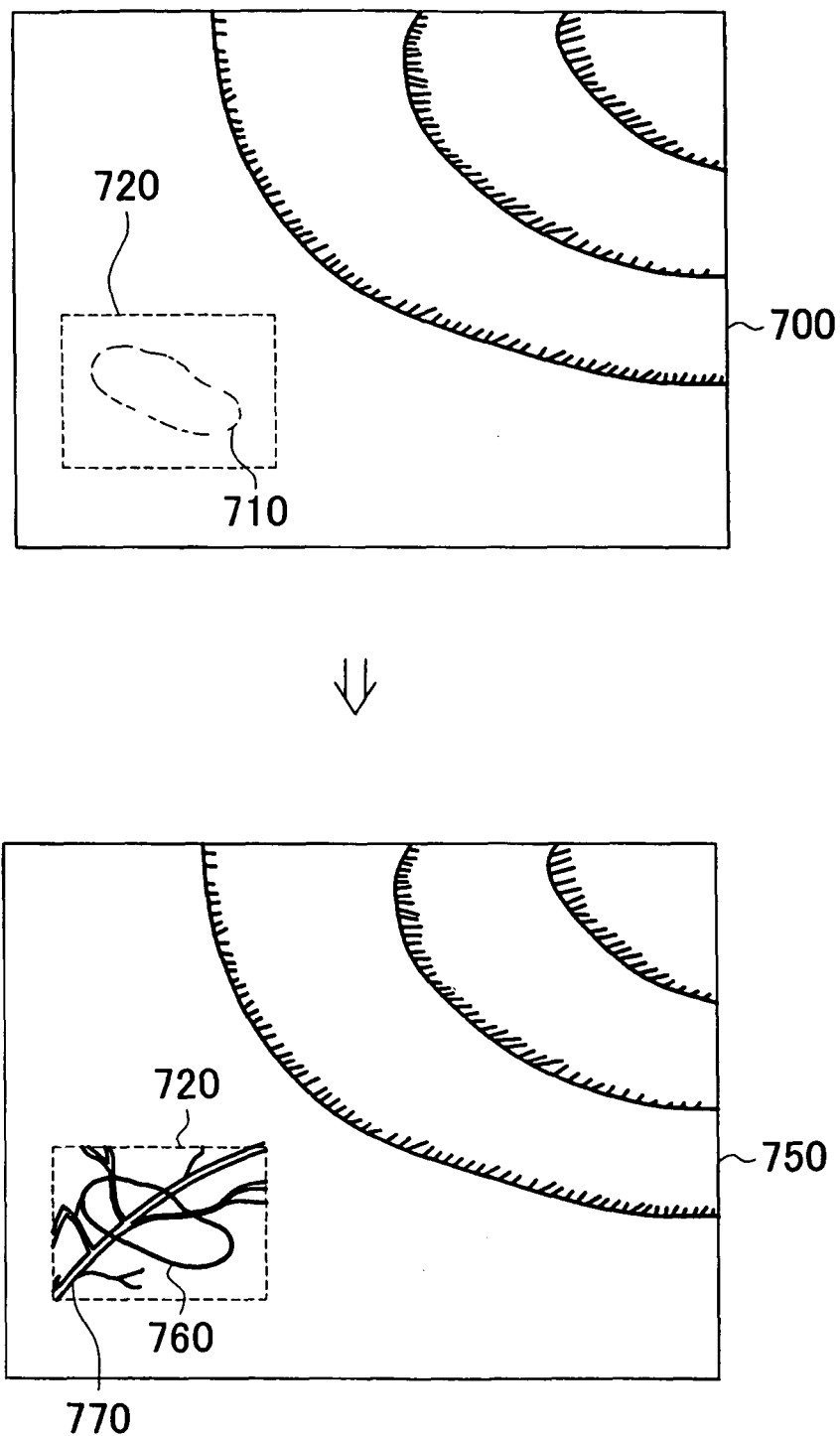
FIG. 7 shows an exemplary image generated by the image processing section 140.

FIG. 7 shows an exemplary image generated by the image processing section 140. The image processing section 140 generates a white light image 700 using the method explained with reference to FIG. 6, and supplies the generated white light image 700 to the output section 150. The output section 150 displays the white light image 700 generated by the image processing section 140. Note that the region 720 in the white light image 700 includes a concave/convex image 710 which represents concave/convex on the surface of the living body 190. In addition, the region 720 in the white light image 700 does not substantially include a depth blood vessel image.

Here, the operation section 160 obtains operation information based on the operation by which a user has specified the region 720 by means of a pointing device or the like. Then the operation section 160 generates, according to the obtained operation information, region information representing the region 720 in the white light image 700, on which an image of a preset spectrum is to be displayed.

In addition, the operation section 160 obtains operation information based on the operation by which the user has specified the type of the image, by means of a button or the like. Then, the operation section 160 generates type information representing the type of the image of the preset spectrum to be displayed, according to the obtained operation information. Note that examples of the type of the image of the preset spectrum are the surface emphasized image 610, the concave/convex emphasized image 620, the hemoglobin emphasized image 630, and the depth blood vessel emphasized image 640 which are already described.

The operation section 160 supplies the region information and the type information to the control section 105. The control section 105 controls the image capturing section 110, the image processing section 140, and the light irradiation section 120, according to the region information and the type information.

Specifically, the irradiation control section 122, according to the type information, controls the wavelength of the light emitted from the excitation section 124 as well as the light emission period thereof. For example, when the type information represents the depth blood vessel emphasized image 640 and the concave/convex emphasized image 620, the irradiation control section 122 controls the excitation section 124 to emit the excitation light of the wavelength region 510 in the first period, as well as controlling the excitation section 124 to emit the excitation light of the wavelength region 530 and the excitation light of the wavelength region 570 in the second period. The irradiation control section 122 controls the excitation section 124 to sequentially switch between the emission of the excitation light of the wavelength region 510 and the emission of the excitation light of the wavelength region 570 and the excitation light of the wavelength region 530.

The image processing section 140 is able to generate the concave/convex emphasized image 620, the depth blood vessel emphasized image 640, and the white light image, by means of the above-described processing with reference to FIG. 6 and with use of the images that the image capturing section 110 has captured in the first period and the second period. The image processing section 140 generates a combined image 750 by combining the white light image with the generated image of the region 720 in the concave/convex emphasized image 620 and the depth blood vessel emphasized image 640, and supplies the generated combined image 750 to the output section 150. The output section 150 displays the combined image 750. Accordingly, in the region 720 of the combined image 750, the depth blood vessel image 770 can be obtained in which the concave/convex images 760 where the concave/convex are emphasized as well as the depth blood vessel image 770 where blood vessels in the depth are emphasized.

Note that the irradiation control section 122 may control the irradiation range to be irradiated by the light irradiation section 120, according to the region information. For example, the irradiation control section 122 may irradiate the range of the real space corresponding to the region information with the luminescence light emitted from the light emitting body by means of the excitation light of the wavelength region 530 and the excitation light of the wavelength region 570. Accordingly, the image processing section 140 is able to generate an image similar to the combined image 750 in the region 720, as well as generating the image similar to the white light image 700 in the region other than the region 720.

In this way, the irradiation control section 122 may irradiate respectively different ranges, with irradiation light resulting from combining light rays of different spectral forms from each other in different combinations from each other. The image processing section 140 is able to generate images of different spectrums in different image regions from each other.

Figure 8:
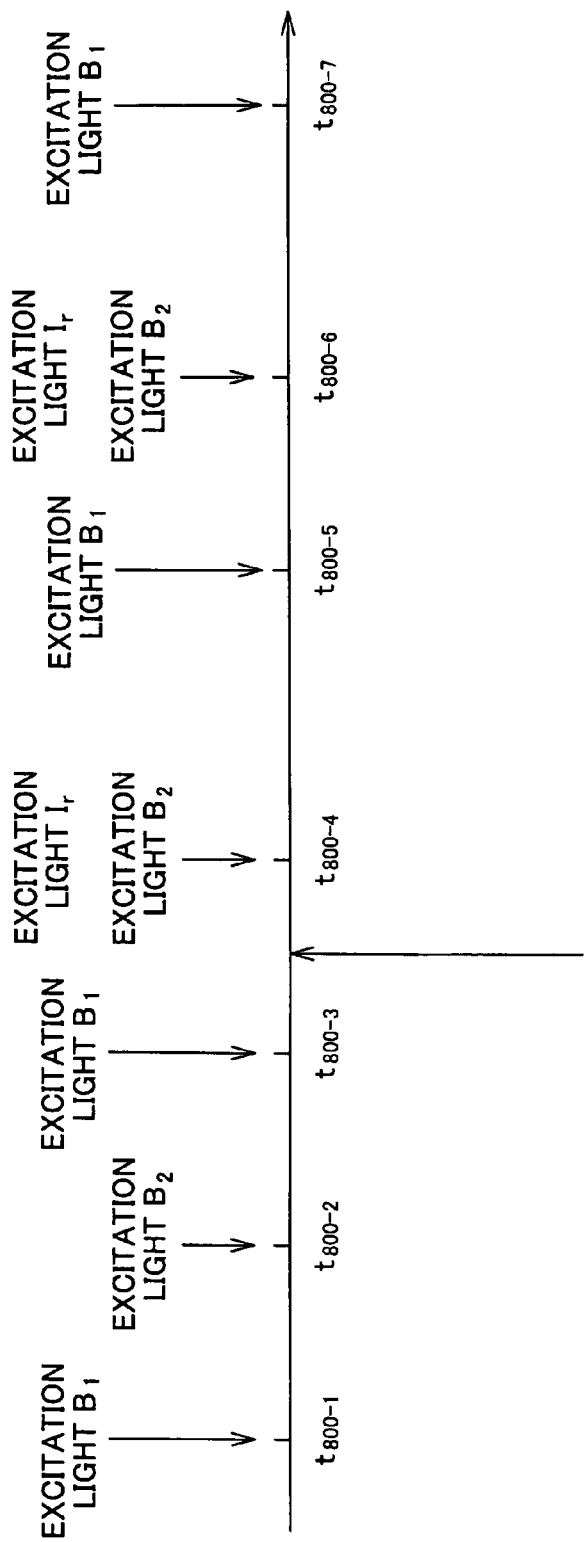
FIG. 8 shows an exemplary light emission sequence of excitation light in the excitation section 124.

FIG. 8 shows an exemplary light emission sequence of excitation light by the excitation section 124. While the type information representing the white light image is supplied to the control section 105, or while no specific type information is supplied to the control section 105, the light irradiation section 120 causes the excitation section 124 to alternately generate excitation light B1 in the wavelength region 510 and excitation light B2 in the wavelength region 530. For example, as illustrated, the irradiation controls section 122 controls the excitation section 124 to alternately generate the excitation light B1 and the excitation light B2 from the time t800-1 to the time t800-3.

When the operation section 160 has supplied the control section 105 with type information of a type corresponding to the image in which the depth blood vessel is emphasized, the irradiation control section 122 controls the excitation section 124 to alternately generate the excitation light Ir of the wavelength region 570, the excitation light B2, and the excitation light B1. For example, as illustrated, the irradiation control section 122 causes the excitation light B2 and the excitation light Ir to be generated at the time t800-4 according to the next image capturing timing, and causes the excitation light B1 to be generated at the time t800-5 according to the next image capturing timing.

Here, the intensity of the luminescence light emitted from the light emitting body by means of the excitation light B2 is assumed to be weaker than the intensity of the luminescence light emitted from the light emitting body by means of the excitation light B1. In addition, the intensity of the luminescence light emitted from the ICG in the living body 190 is assumed to be weaker than the intensity of the reflected light resulting from reflection of the luminescence light emitted from the light emitting body by means of the excitation light B1 by the living body 190. In this case, when the time length of the exposure period of the light reception section 200 is temporally fixed, the luminance resolution of the image is occasionally impaired.

With this in mind, the control section 105 controls the image capturing section 110 to perform image capturing at a longer image capturing period at the time t800-4 and at the time t800-6, than at the time t800-5 and the time t800-7. The irradiation control section 122 controls the excitation section 124 to emit excitation light at a longer light emission period at the time t800-4 and at the time t800-6, than at the time t800-5 and at the time 800-7. Specifically, the irradiation control section 122 controls the excitation section 124 to generate excitation light during a period according to the image capturing period of the image capturing section 110.

In this way, the irradiation control section 122 determines the intensity of the excitation light generated by the excitation section 124 as well as its spectral form. Accordingly, the spectrum of the irradiation light is determined. The control section 105 determines the exposure period of the light reception section 200 according to the spectrum of the irradiation light irradiated from the light irradiation section 120, and exposes the light reception section 200 for the exposure period. In addition, the irradiation control section 122 controls the period in which the excitation section 124 emits excitation light, so that the irradiation light is irradiated at least during the exposure period.

By the emission of the excitation light by the excitation section 124 in the illustrated light emission sequence, the image processing section 140 is able to generate a white light image as well as a depth blood vessel emphasized image 640, from the images captured at the time t800-3 and at the time t800-4. In addition, the image processing section 140 is able to generate a white light image at the next timing, from the images captured at the time t800-4 and at the time t800-5. In this way, the endoscope system 10 is able to rapidly generate an image according to an observation objective.

Note that the irradiation control section 122 is able to cause, to be different, the effective spectrum of the irradiation light between a plurality of exposure periods, by causing, to be different, the time length across which light rays having different spectral forms from each other irradiate the living body 190 between the plurality of exposure periods. For example, the irradiation control section 122 may cause, to be different, the time length across which the excitation section 124 emits excitation light, between a plurality of exposure periods. Accordingly, the light irradiation section 120 is able to irradiate the living body 190 with irradiation light rays having different effective spectrums from each other at respectively different timings. In addition, the image processing section 140 is able to generate a variety of images, by respectively correcting the images captured by the image capturing section 110, according to an effective spectrum based on the above-described time length.

As described above, the light rays having different spectral forms from each other, which are to be combined into irradiation light, may have different wavelength regions from each other. In addition, irradiation light rays having different spectrums from each other may have different wavelength regions from each other. In this case the image capturing section 110 may capture a plurality of images of a subject irradiated with irradiation light rays having different wavelength regions from each other at respectively different timings. Then, the image processing section 140 may generate an image of a specific wavelength region as an image of a preset spectrum, from the plurality of images captured by the image capturing section 110.

In the present embodiment, an example of the operation of each constituting element of the endoscope system 10 has been described, using the living body 190 as an exemplary subject. However, the subject is not limited to the living body 190, and can include an article such as a product manufactured industrially and a natural object other than a living organism.

FIG. 9 shows an exemplary block configuration of an image capturing apparatus 2100 according to an embodiment. The image capturing apparatus 2100 includes a light emission section 2110, a light emission control section 2124, an image capturing section 2130, an image capturing control section 2138, a motion detection section 2142, a motion vector calculation section 2144, a wideband interpolation image generating section 2146, a narrowband interpolation image generating section 2148, and a display section 2150.

The image capturing apparatus 2100 may be an endoscope. When the image capturing apparatus 2100 is an endoscope, the light emission section 2110 and the image capturing section 2130 may be provided at the tip of the insertion section of the endoscope inserted to a living body. In another example, the light emission section 2110 may be provided outside the insertion section, to irradiate the living body via the light guide provided at the insertion section of the endoscope. The image capturing section 2130 may also be provided outside the insertion section, to receive light from the living body, via the light guide provided at the insertion section of the endoscope.

The image capturing section 2130 includes a plurality of light reception sections. Specifically, the image capturing section 2130 includes a first light reception section 2132, a second light reception section 2134, and a third light reception section 2136. The first light reception section 2132, the second light reception section 2134, and the third light reception section 2136 respectively include a plurality of light reception elements. The image capturing section 2132 may be a CCD or a CMOS in which the light reception elements of the first light reception section 2130, the light reception elements of the second light reception section 2134, and the light reception elements of the third light reception section 2136 are arranged on a regular basis. In another example, each of the first light reception section 2132, the second light reception section 2134, and the third light reception section 2136 may be a CCD or a CMOS independent from each other.

The first light reception section 2132 mainly receives the light of the first wavelength region. For example, the first light reception section 2132 mainly receives the light of the B wavelength region (420 nm-490 nm).

The second light reception section 2134 mainly receives the light of the second wavelength region that is different from the first wavelength region. For example, the second light reception section 2134 mainly receives the light of the G wavelength region (490 nm-600 nm).

The third light reception section 2136 mainly receives the light of the third wavelength region that is different from any of the first wavelength region and the second wavelength region. For example, the third light reception section 2136 mainly receives the light of the R wavelength region (600 nm-750 nm).

The light emission section 2110 includes a plurality of light emission sections. Specifically, the light emission section 2110 includes a first light emission section 2112, a second light emission section 2114, a third light emission section 2116, a fourth light emission section 2118, a fifth light emission section 2120, and a sixth light emission section 2122.

The first light emission section 2112 mainly emits the first narrowband light that is light of a part of the first wavelength region. The first light emission section 2112 may be an LED that mainly emits the first narrowband light. The first light emission section 2112 may include a filter that mainly transmits the first narrowband light.

The second light emission section 2114 mainly emits the second narrowband light that is light of a part of the first wavelength region and is different from the first narrowband light. The second light emission section 2114 may be an LED that mainly emits the second narrowband light. The second light emission section 2114 may include a filter that mainly transmits the second narrowband light.

The third light emission section 2116 mainly emits the third narrowband light that is light of a part of the second wavelength region. The third light emission section 2116 may be an LED that mainly emits the third narrowband light. The third light emission section 2116 may include a filter that mainly transmits the third narrowband light.

The fourth light emission section 2118 mainly emits the fourth narrowband light that is light of a part of the second wavelength region and is different from the third narrowband light. The fourth light emission section 2118 may be an LED that mainly emits the fourth narrowband light. The fourth light emission section 2118 may include a filter that mainly transmits the fourth narrowband light.

The fifth light emission section 2120 mainly emits the fifth narrowband light that is light of a part of the third wavelength region. The fifth light emission section 2120 may be an LED that mainly emits the fifth narrowband light. The fifth light emission section 2120 may include a filter that mainly transmits the fifth narrowband light.

The sixth light emission section 2122 mainly emits the sixth narrowband light that is light of a part of the third wavelength region and is different from the fifth narrowband light. The sixth light emission section 2122 may be an LED that mainly emits the sixth narrowband light. The sixth light emission section 2122 may include a filter that mainly transmits the sixth narrowband light.

Here, in the image capturing apparatus 2100, it is desirable to arrange the plurality of light emission sections so that the light intensity and the light distribution of the plurality of light emission sections are respectively constant. In particular, the plurality of light emission sections should desirably be grouped into each wavelength regions, so that the light intensity and the light distribution within each group are respectively constant.

The light emission control section 2124 controls the first light emission section 2112 and the second light emission section 2114 to periodically emit light, by causing, to be different, either the light emission period or the light emission phase between the first light emission section 2112 and the second light emission section 2114. In addition, the light emission control section 2124 sets either the light emission period or the light emission phase of the third light emission section 2116 to be equal to that of the first light emission section 2112, and sets either the light emission period or the light emission phase of the fourth light emission section 2118 to be equal to that of the second light emission section 2114, so as to control the third light emission section 2116 and the fourth light emission section 2118 to periodically emit light. In addition, the light emission control section 2124 sets either the light emission period or the light emission phase of the fifth light emission section 2120 to be equal to that of the first light emission section 2112 and that of the third light emission section 2116, and sets either the light emission period or the light emission phase of the sixth light emission section 2122 to be equal to that of the second light emission section 2114 and that of the fourth light emission section 2118, so as to control the fifth light emission section 2120 and the sixth light emission section 2122 to periodically emit light.

The image capturing control section 2138 successively captures a narrowband image being an image of light received by the first light reception section 2132 when one of the first light emission 2112 and the second light emission section 2114 has emitted light, and a wideband image being an image of light received by the first light reception section when both of the first light emission section 2112 and the second light emission section 2114 have emitted light. The image capturing control section 2138 may also successively capture a) a narrowband image being an image of light received by the first light reception section 2132 and the second light reception section 2134 when one of the first light emission section 2112 and the second light emission section 2114 as well as one of the third light emission section 2116 and the fourth light emission section 2118 have emitted light, and b) a wideband image being an image of light received by the first light reception section 2132 and the second light reception section 2134 when the first light emission section 2112 through the fourth light emission section 2118 have emitted light. Moreover, the image capturing control section 2138 may successively capture a) a narrowband image being an image of light received by the first light reception section 2132 through the third light reception section 2136 when one of the first light emission section 2112 and the second light emission section 2114, one of the third light emission section 2116 and the fourth light emission section 2118, and one of the fifth light emission section 2120 and the sixth light emission section 2122 have emitted light, and b) a wideband image being an image of light received by the first light reception section 2132 through the third light reception section 2136 when the first light reception section 2112 through the sixth light reception section 2122 have emitted light. The image capturing control section 2138 may capture a wideband image and a narrowband image in accordance with the light emission timings of the plurality of light emission sections under control by the light emission control section 2124.

The motion detection section 2142 detects relative motion between the image capturing section 2130 and a subject. The motion detection section 2142 may detect relative motion between the image capturing section 2130 and a subject, by using a gyro sensor or the like. The motion detection section 2142 may detect relative motion between the image capturing section 2130 and a subject, from a plurality of wideband images. In this case, the motion detection section 2142 may detect relative motion between the image capturing section 2130 and a subject, based on a landmark such as a blood vessel, scissors, a lesion, or an incision included in a plurality of wideband images.

The motion vector calculation section 2144 calculates a first motion vector of a subject between a timing at which a wideband image is displayed and a timing at which a wideband interpolation image is displayed, based on the motion information detected by the motion detection section 2142. In addition, the motion vector calculation section 2144 calculates a second motion vector of a subject between a timing at which a narrowband image is displayed and a timing at which a wideband interpolation image is displayed, based on the motion information detected by the motion detection section 2142.

In addition, the motion vector calculation section 2144 calculates a third motion vector of a subject between a timing at which a narrowband image is displayed and a timing at which a narrowband interpolation image is displayed, based on the motion information detected by the motion detection section 2142. In addition, the motion vector calculation section 2144 calculates a fourth motion vector of a subject between a timing at which a wideband image is displayed and a timing at which a narrowband interpolation image is displayed, based on the motion information detected by the motion detection section 2142.

The wideband interpolation image generating section 2146 generates a wideband interpolation image interpolating a plurality of wideband images, based on the wideband image and the narrowband image. Specifically, the wideband interpolation image generating section 2146 generates a wideband interpolation image frame-interpolating the plurality of wideband images. The wideband interpolation image generating section 2146 may generate a wideband interpolation image based on chromaticity information of the wideband image and brightness information of the narrowband image.

In addition, the wideband interpolation image generating section 2146 may generate a wideband interpolation image further based on the motion information detected by the motion detection section 2142. In addition, the wideband interpolation image generating section 2146 may generate the chromaticity information of the pixels of the wideband interpolation image, from the chromaticity information of the pixels included in the wideband image, based on the first motion vector calculated by the motion vector calculation section 2144. In addition, the wideband interpolation image generating section 2146 may generate the brightness information of the pixels of the wideband interpolation image, from the brightness information of the pixels included in the narrowband image, based on the second motion vector calculated by the motion vector calculation section 2144.

The narrowband interpolation image generating section 2148 generates a narrowband interpolation image interpolating a plurality of narrowband images, based on the wideband image and the narrowband image. Specifically, the narrowband interpolation image generating section 2148 generates a narrowband interpolation image frame-interpolating the plurality of narrowband images. The narrowband interpolation image generating section 2148 may generate a narrowband interpolation image based on brightness information of the wideband image and chromaticity information of the narrowband image.

In addition, the narrowband interpolation image generating section 2148 may generate a narrowband interpolation image further based on the motion information detected by the motion detection section 2142. In addition, the narrowband interpolation image generating section 2148 may generate the chromaticity information of the pixels of the narrowband interpolation image, from the chromaticity information of the pixels included in the narrowband image, based on the third motion vector calculated by the motion vector calculation section 2144. In addition, the narrowband interpolation image generating section 2148 may generate the brightness information of the pixels of the narrowband interpolation image, from the brightness information of the pixels included in the wideband image, based on the fourth motion vector calculated by the motion vector calculation section 2144.

The display section 2150 displays a wideband moving image and a narrowband moving image. The wideband moving image is a moving image that includes a plurality of wideband images. The narrowband moving image is a moving image that includes a plurality of narrowband images. The wideband moving image may further include a plurality of wideband interpolation images. The narrowband moving image may further include a plurality of narrowband interpolation images.

The display section 2150 may simultaneously display the wideband moving image and the narrowband moving image. The display section 2150 may simultaneously display the wideband moving image and the narrowband moving image in synchronization with each other. The display section 2150 may display the wideband moving image and the narrowband moving image in alignment with each other. In addition, the display section 2150 may display the wideband moving image and the narrowband moving image overlapped with each other.

FIG. 10 shows an exemplary spectrum of light emitted from the light emission section 2110. The spectrum 2201 represents a spectrum of light emitted from the first light emission section 2112. For example, the first light emission section 2112 emits narrowband light that is mainly in a wavelength region of 400 nm to 450 nm, within a first wavelength region that is mainly in a wavelength region of 400 nm to 490 nm.

The spectrum 2202 represents a spectrum of light emitted from the second light emission section 2114. For example, the second light emission section 2114 emits narrowband light that is mainly in a wavelength region of 450 nm to 490 nm, within a first wavelength region that is mainly in a wavelength region of 400 nm to 490 nm.

The spectrum 2203 represents a spectrum of light emitted from the third light emission section 2116. For example, the third light emission section 2116 emits narrowband light that is mainly in a wavelength region of 490 nm to 550 nm, within a second wavelength region that is mainly in a wavelength region of 490 nm to 600 nm.

The spectrum 2204 represents a spectrum of light emitted from the fourth light emission section 2118. For example, the fourth light emission section 2118 emits narrowband light that is mainly in a wavelength region of 550 nm to 600 nm, within a second wavelength region that is mainly in a wavelength region of 490 nm to 600 nm.

The spectrum 2205 represents a spectrum of light emitted from the fifth light emission section 2120. For example, the fifth light emission section 2120 emits narrowband light that is mainly in a wavelength region of 600 nm to 675 nm, within a third wavelength region that is mainly in a wavelength region of 600 nm to 750 nm.

The spectrum 2206 represents a spectrum of light emitted from the sixth light emission section 2122. For example, the sixth light emission section 2122 emits narrowband light that is mainly in a wavelength region of 675 nm to 750 nm, within a third wavelength region that is mainly in a wavelength region of 600 nm to 750 nm.

In the present embodiment, two light emission sections are assigned to one wavelength region. However, not limited to this configuration, the present invention can also be realized by assigning three or more light emission sections to one wavelength region. In addition, the combination of the light emission sections to emit light, the light emission period, the light emission phase, the wavelength region, or the light intensity can be modified depending on the light absorption characteristic and the light reflection characteristic of the observation target.

Figure 11:
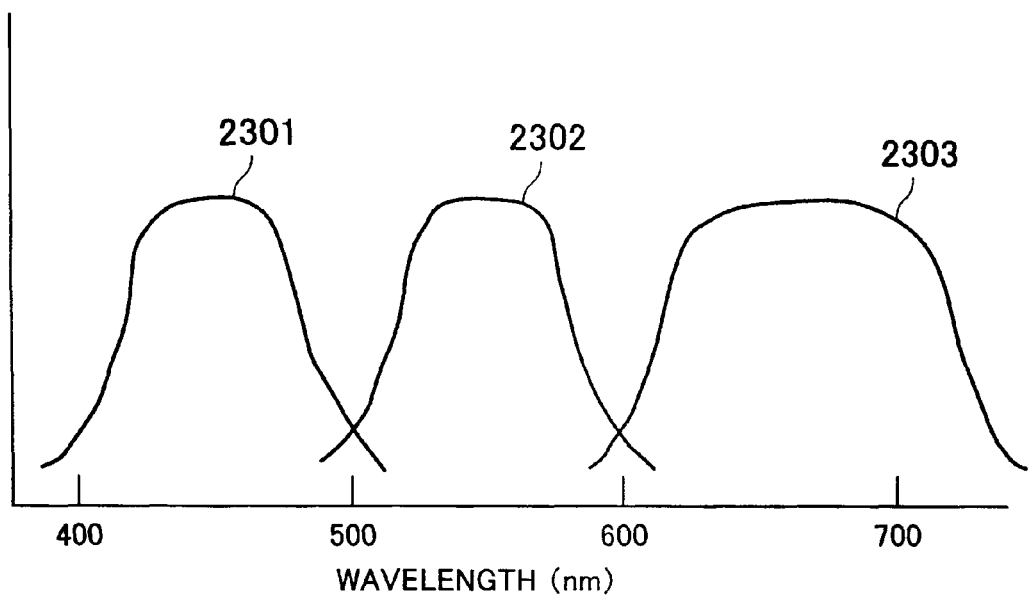
FIG. 11 shows an exemplary light reception characteristic of an image capturing section 2130.

FIG. 11 shows an exemplary light reception characteristic of an image capturing section 2130. The light reception characteristic 2301 represents the light reception characteristic of the first light reception section 2132. For example, the first light reception section 2132 receives light mainly in a wavelength region of 400 nm to 490 nm within the first wavelength region.

The light reception characteristic 2302 represents the light reception characteristic of the second light reception section 2134. For example, the second light reception section 2134 receives light mainly in a wavelength region of 490 nm to 600 nm within the second wavelength region.

The light reception characteristic 2303 represents the light reception characteristic of the third light reception section 2136. For example, the third light reception section 2136 receives light mainly in a wavelength region of 600 nm to 750 nm within the third wavelength region.

Figure 12:
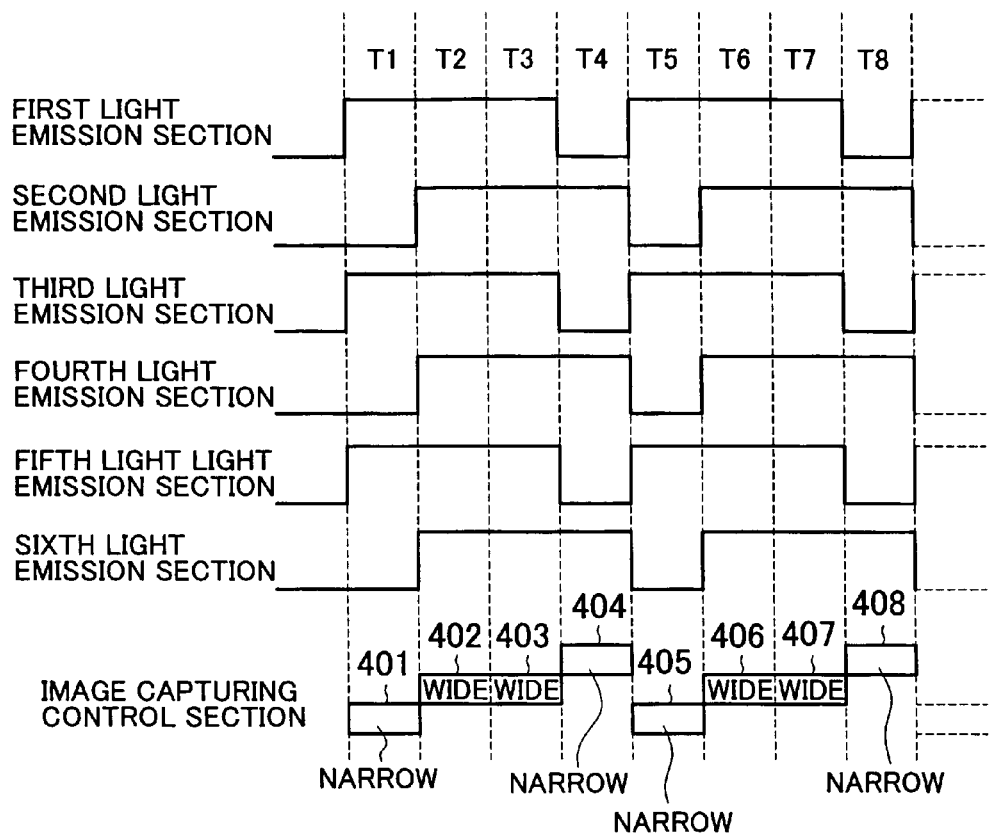
FIG. 12 shows exemplary control performed by the light emission control section 2124 and the image capturing control section 2138.

FIG. 12 shows exemplary control performed by the light emission control section 2124 and the image capturing control section 2138. The light emission control section 2124 controls the light emission timing of the first light emission section 2112-the sixth light emission section 2122. In the present example, the light emission control section 2124 controls the light emission phases of the first light emission section 2112-the sixth light emission section 2122 to be different from each other, without causing the light emission period to be different among them. Alternatively, however, the light emission periods may differ between the light emission sections, without causing the light emission phase to be different among them. Still alternatively, both of the light emission period and the light emission phase can be controlled to be different among them. In other words, the light emission control section 2124 may control at least one of the light emission period and the light emission phase, among the first light emission section 2112-the sixth light emission section 2122, so as to successively change the wavelength region of light emitted from the first light emission section 2112-the sixth light emission section 2122.

For example, at the timing T1, the light emission control section 2124 controls the first light emission section 2112, the third light emission section 2116, and the fifth light emission section 2120 to emit light. According to this, the first light reception section 2132, for example, receives an image of light of 400-450 nm. The second light reception section 2134 receives an image of light of 490-550 nm. The third light reception section 2136 receives an image of light of 600-675 nm. The image capturing control section 2138 captures a narrowband image 2401 of wavelength regions of 400-450 nm, 490-550 nm, and 600-675 nm.

At the timings T2 and T3, the light emission control section 2124 controls all the first light emission section 2112-the sixth light emission section 2122 to emit light. By doing so, the first light reception section 2132, for example, receives an image of light of 400-490 nm. The second light reception section 2134 receives an image of light of 490-600 nm. The third light reception section 2136 receives an image of light of 600-750 nm. The image capturing control section 2138 captures wideband images 2402 and 2403 of a wavelength region of 400-750 nm.

At the timing T4, the light emission control section 2124 controls the second light emission section 2114, the fourth light emission section 2118, and the sixth light emission section 2122 to emit light. By doing so, the first light reception section 2132 receives an image of light of 450-490 nm. The second light reception section 2134 receives an image of light of 550-600 nm. The third light reception section 2136 receives an image of light of 675-750 nm. The image capturing control section 2138 captures a narrowband image 2404 of wavelength regions of 450-490 nm, 550-600 nm, and 675-750 nm.

Likewise, at the timing T5, the image capturing control section 2138 captures a narrowband image 2405 of wavelength regions of 400-450 nm, 490-550 nm, and 600-675 nm. At the timings T6 and T7, the image capturing control section 2138 captures wideband images 2406 and 2407 of a wavelength region of 400-750 nm. At the timing T8, the image capturing control section 2138 captures a narrowband image 2408 of wavelength regions of 450-490 nm, 550-600 nm, and 675-750 nm.

Figure 13:
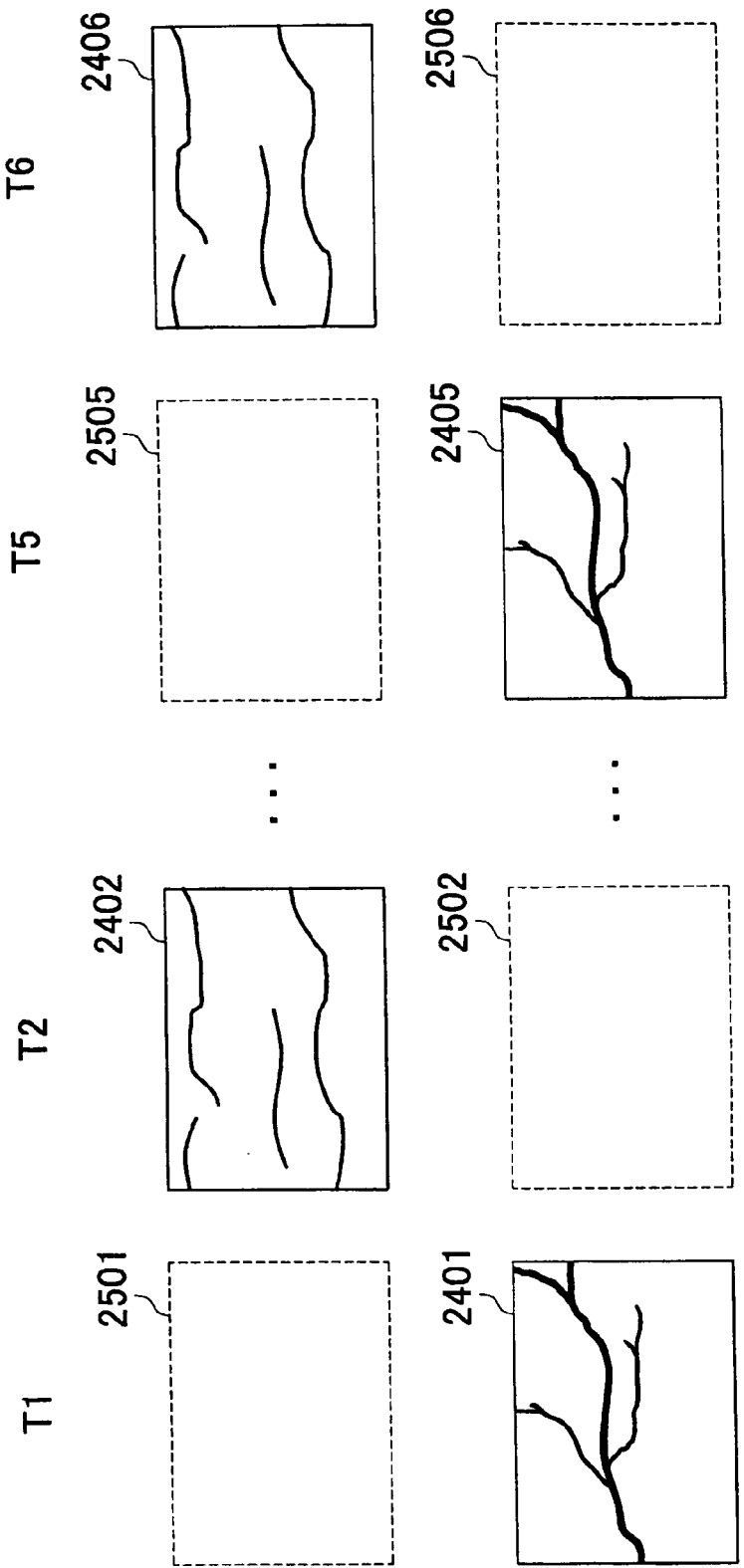
FIG. 13 shows exemplary processing performed by a wideband interpolation image generating section 2146 and a narrowband interpolation image generating section 2148.

FIG. 13 shows an exemplary process performed by a wideband interpolation image generating section 2146 and a narrowband interpolation image generating section 2148. In FIG. 13, each of the wideband image 2402 and the wideband image 2406 represents a wideband image captured by the image capturing control section 2138. Each of the narrowband image 2401 and the narrowband image 2405 represents a narrowband image captured by the image capturing control section 2138.

The wideband interpolation image generating section 2146 generates a wideband interpolation image. For example, the wideband interpolation image generating section 2146 generates a wideband interpolation image 2501 that is a wideband image at the timing T1. In addition, the wideband interpolation image generating section 2146 generates a wideband interpolation image 2505 that is a wideband image at the timing T5.

The wideband interpolation image generating section 2146 may generate a wideband interpolation image based on the chromaticity information of the wideband image and the brightness information of the narrowband image. For example, the wideband interpolation image generating section 2146 may generate a wideband interpolation image 2505 based on the chromaticity information of the wideband images before and after the wideband interpolation image 2505 and the brightness information of the narrowband image

2405. The wideband interpolation image generating section 2146 may generate the wideband interpolation image 2505, further based on the brightness information of narrowband images other than the narrowband image 2405. The wideband interpolation image generating section 2146 may generate the wideband interpolation image 2505, further based on the brightness information of the wideband images before and after the wideband interpolation image 2505.

When the motion detection section 2142 has detected relative motion between the image capturing section 2130 and a subject, the wide band interpolation image generating section 2146 may generate the wideband interpolation image, further based on the motion information detected by the motion detection section 2142. The motion detection section 2142 may detect the relative motion between the image capturing section 2130 and a subject, by means of a gyro sensor or the like. The motion detection section 2142 may detect the relative motion between the image capturing section 2130 and the subject, from a plurality of wideband images. In this case, the motion detection section 2142 may detect relative motion between the image capturing section 2130 and a subject, based on a landmark such as a blood vessel, scissors, a lesion, or an incision included in a plurality of wideband images.

When the motion vector calculation section 2144 has detected a first motion vector, the wideband interpolation image generating section 2146 may generate the chromaticity information of the pixels of the wideband interpolation image, from the chromaticity information of the pixels included in the wideband image, based on the first motion vector calculated by the motion vector calculation section 2144. The first motion vector is a motion vector of a subject between a timing at which a wideband image is displayed and a timing at which a wideband interpolation image is displayed. For example, the motion vector calculation section 2144 calculates the first motion vector based on the motion information detected by the motion detection section 2142. For example, the wideband interpolation image generating section 2146 may generate the chromaticity information of the pixels of the wideband interpolation image 2505 from the chromaticity information of the pixels included in the wideband image before or after the wideband interpolation image 2505, based on the motion vector of the subject between the timing at which the wideband image before or after the wideband interpolation image 2505 is displayed and the timing at which the wideband interpolation image 2505 is displayed.

When the motion vector calculation section 2144 has calculated a second motion vector, the wideband interpolation image generating section 2146 may generate the brightness information of the pixels of the wideband interpolation image from the brightness information of the pixels included in the narrowband image, based on the second motion vector calculated by the motion vector calculation section 2144. The second motion vector is a motion vector of a subject between a timing at which a narrowband image is displayed and a timing at which a wideband interpolation image is displayed. For example, the motion vector calculation section 2144 calculates the second motion vector based on the motion information detected by the motion detection section 2142. For example, the wideband interpolation image generating section 2146 may generate the chromaticity information of the pixels of the wideband interpolation image 2505 from the chromaticity information of the pixels included in the narrowband image before or after the wideband interpolation image 2505, based on the motion vector of the subject between the timing at which the narrowband image before or after the wideband interpolation image 2505 is displayed and the timing at which the wideband interpolation image 2505 is displayed.

The narrowband interpolation image generating section 2148 generates a narrowband interpolation image. For example, the narrowband interpolation image generating section 2148 generates a narrowband interpolation image 2502 being a narrowband image at the timing T2. In addition, the narrowband interpolation image generating section 2148 generates a narrow interpolation image 2506 being the narrowband image at the timing T6.

The narrowband interpolation image generating section 2148 may generate a narrowband interpolation image, based on the brightness information of the wideband image and the chromaticity information of the narrowband image. For example, the narrowband interpolation image generating section 2148 may generate a narrowband interpolation image 2502, based on the chromaticity information of the narrowband image before or after narrowband interpolation image 2502 and the brightness information of the wideband image 2402. The narrowband interpolation image generating section 2148 may generate the narrowband interpolation image 2502, further based on the brightness information of wideband images other than the wideband image 2402. The narrowband interpolation image generating section 2148 may generate the narrowband interpolation image 2502, further based on the brightness information of the narrowband image before or after the narrowband interpolation image 2502. When the motion detection section 2142 has detected relative motion between the image capturing section 2130 and a subject, the narrowband interpolation image generating section 2148 may generate the narrowband interpolation image, further based on the motion information detected by the motion detection section 2142.

When the motion vector calculation section 2144 has calculated the third motion vector, the narrowband interpolation image generating section 2148 may generate the chromaticity information of the pixels of the narrowband interpolation image from the chromaticity information of the pixels included in the narrowband image, based on the third motion vector calculated by the motion vector calculation section 2144. The third motion vector is a motion vector of a subject between a timing at which a narrowband image is displayed and a timing at which a narrowband interpolation image is displayed. For example, the motion vector calculation section 2144 calculates the third motion vector based on the motion information detected by the motion detection section 2142. For example, the narrowband interpolation image generating section 2148 may generate the chromaticity information of the pixels of the narrowband interpolation image 2502 from the chromaticity information included in the narrowband image before or after the narrowband interpolation image 2502, based on the motion vector of the subject between the timing at which the narrowband image before or after the narrowband interpolation image 2502 is displayed and the timing at which the narrowband interpolation image 2502 is displayed.

When the motion vector calculation section 2144 has calculated a fourth motion vector, the narrowband interpolation image generating section 2148 may generate brightness information of the pixels of the narrowband interpolation image from the brightness information of the pixels included in the wideband image, based on the fourth motion vector calculated by the motion vector calculation section 2144. The fourth motion vector is a motion vector of a subject between a timing at which a wideband image is displayed and a timing at which a narrowband interpolation image is displayed. For example, the motion vector calculation section 2144 calculates the fourth motion vector based on the motion information detected by the motion detection section 2142. For example, the narrowband interpolation image generating section 2148 may generate the chromaticity information of the pixels of the narrowband interpolation image 2502 from the chromaticity information of the pixels included in the wideband image before or after the narrowband interpolation image 2502, based on the motion vector of the subject between the timing at which the wideband image before or after the narrowband interpolation image 2502 is displayed and the timing at which the narrowband interpolation image 2502 is displayed.

In this way, the image capturing apparatus 2100 according to the present embodiment is able to control the light emission timings of the plurality of light emission sections respectively, and so can control the image capturing period of the narrowband image and the image capturing period of the wideband image independently from each other. In addition, the image capturing apparatus 2100 can generate a narrowband interpolation image and a wideband interpolation image, thereby enabling to generate a narrowband image and a wideband image belonging to the same timing.

View 2146 is an example of display processing by the display section 2150. The screen 2600 displays a moving image 2610 and a moving image 2620. The moving image 2610 includes a narrowband image captured by the image capturing control section 2138 and a narrowband interpolation image generated by the narrowband interpolation image generating section 2148.

The moving image 2620 includes a wideband image captured by the image capturing control section 2138 and a wideband interpolation image generated by the wideband interpolation image generating section 2146. In this way, the display section 2150 may display the wideband moving image and the narrowband moving image in alignment with each other. The display section 2150 may display the wideband moving image and the narrowband moving image in synchronization with each other.

The display section 2150 may display a narrowband moving image that includes a narrowband image received by a part of the first light reception section 2132-the third light reception section 2136. For example, the display section 2150 may select any of the narrowband moving image including the narrowband image received by the first light reception section 2132, the narrowband moving image including the narrowband image received by the second light reception section 2134, and the narrowband moving image including the narrowband image received by the third light reception section 2136, and displays the selected narrowband moving image.

FIG. 15 shows different exemplary display processing performed by the display section 2150. The screen 2700 displays the moving image 2710. The moving image 2710 shows a combined moving image between a narrowband moving image and a wideband moving image, where the narrowband moving image includes the narrowband image captured by the image capturing control section 2138 and the narrowband interpolation image generated by the narrowband interpolation image generating section 2148, and the wideband moving image includes the wideband image captured by the image capturing control section 2138 and the wideband interpolation image generated by the wideband interpolation image generating section 2146. In this way, the display section 2150 may display the wideband moving image and the narrowband moving image overlapped with each other.

The display section 2150 may display a combined moving image between a wideband moving image and a narrowband moving image that includes the narrowband image received by part of the first light reception section 2132-the third light reception section 2136. For example, the display section 2150 may overlap the wideband moving image with a narrowband moving image that includes the narrowband image received by the first light reception section 2132, a narrowband moving image that includes the narrowband image received by the second light reception section 2134, and a narrowband moving image that includes the narrowband image received by the third light reception section 2136.

Figure 16:
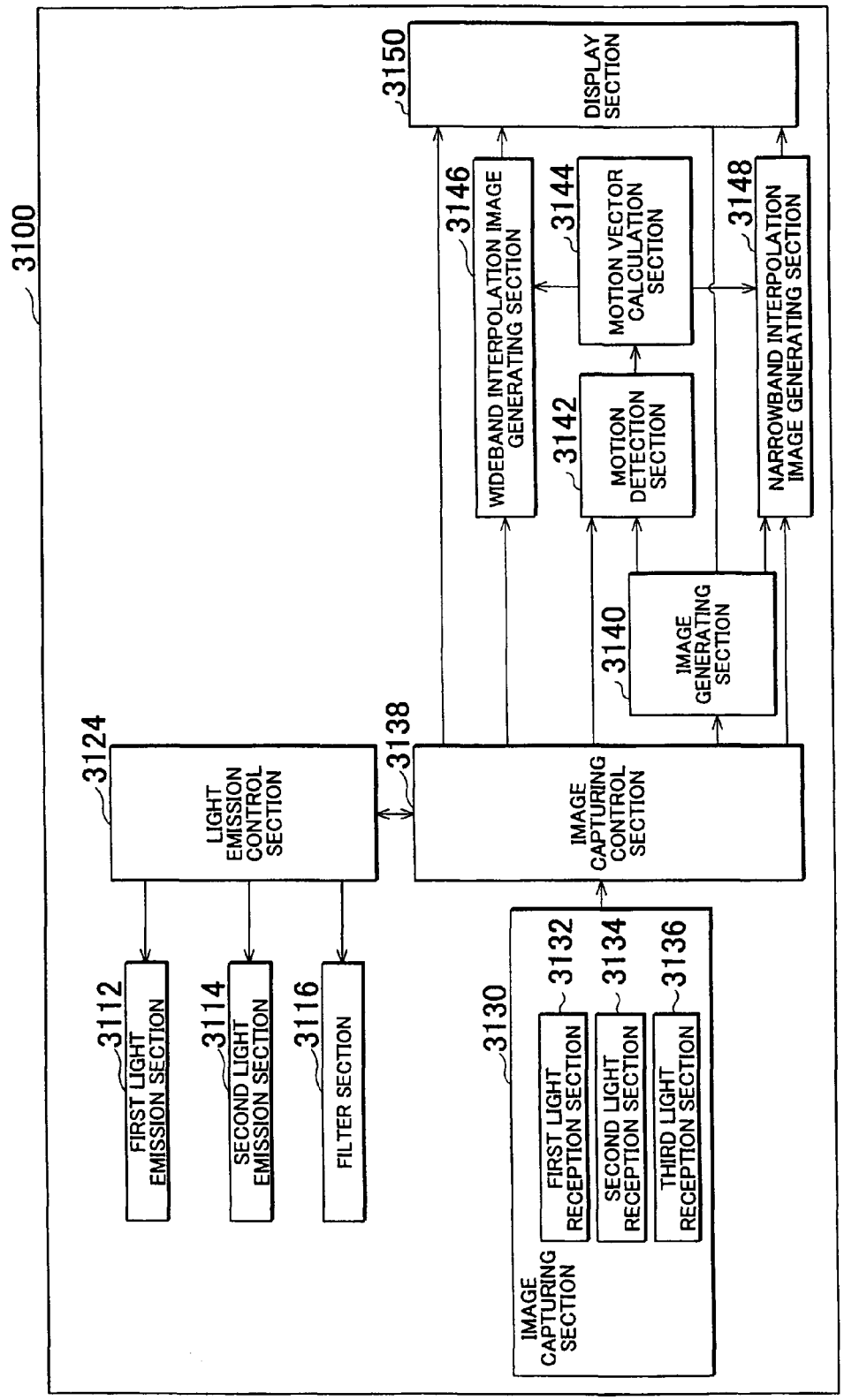
FIG. 16 shows an exemplary block configuration of an image capturing apparatus 3100 according to an embodiment.

FIG. 16 shows an exemplary block configuration of an image capturing apparatus 3100 according to an embodiment. The image capturing apparatus 3100 includes a first light emission section 3112, a second light emission section 3114, a filter section 3116, a light emission control section 3124, an image capturing section 3130, an image capturing control section 3138, an image generating section 3140, a motion detection section 3142, a motion vector calculation section 3144, a wideband interpolation image generating section 3146, a narrowband interpolation image generating section 3148, and a display section 3150. Since the second light emission section 3114 and the filter section 3116 share the same function, the image capturing apparatus 3100 may be equipped with one of the second light emission section 3114 and the filter section 3116.

The image capturing apparatus 3100 may be an endoscope. When the image capturing apparatus 3100 is an endoscope, the first light emission section 3112, the second light emission section 3114, and the image capturing section 3130 may be provided at the tip of the insertion section of the endoscope inserted to a living body. In another example, the first light emission section 3112 and the second light emission section 3114 may be provided outside the insertion section, to irradiate the living body via the light guide provided at the insertion section of the endoscope. The image capturing section 3130 may also be provided outside the insertion section, to receive light from the living body, via the light guide provided at the insertion section of the endoscope.

The image capturing section 3130 includes a plurality of light reception sections. Specifically, the image capturing section 3130 includes a first light reception section 3132, a second light reception section 3134, and a third light reception section 3136. The first light reception section 3132, the second light reception section 3134, and the third light reception section 3136 respectively include a plurality of light reception elements. The image capturing section 3130 may be a CCD or a CMOS in which light reception elements of the first light reception section 3132, light reception elements of the second light reception section 3134, and light reception elements of the third light reception section 3136 are arranged on a regular basis. In another example, each of the first light reception section 3132, the second light reception section 3134, and the third light reception section 3136 may be a CCD or a CMOS independent from each other.

The first light reception section 3132 mainly receives the light of the first wavelength region. For example, the first light reception section 3132 mainly receives the light of the B wavelength region (420 nm-490 nm).

The second light reception section 3134 mainly receives the light of the second wavelength region that is different from the first wavelength region. For example, the second light reception section 3134 mainly receives the light of the G wavelength region (490 nm-600 nm).

The third light reception section 3136 mainly receives the light of the third wavelength region that is different from any of the first wavelength region and the second wavelength region. For example, the third light reception section 3136 mainly receives the light of the R wavelength region (600 nm-750 nm).

The first light emission section 3112 emits wideband light being light of a band including the first wavelength region and the second wavelength region. For example, the first light emission section 3112 emits wideband light being light of a band including the B wavelength region and the G wavelength region. The first light emission section 3112 may emit wideband light being light of a band that further includes the R wavelength region. The first light emission section 3112 may emit white light as wideband light.

The second light emission section 3114 emits narrowband light being light of a band spanning a part of the first wavelength region and a part of the second wavelength region. For example, the second light emission section 3114 emits narrowband light being light of a band spanning a part of the B wavelength region and a part of the G wavelength region.

The filter section 3116 filters light of a band outside the narrowband light being light of a band spanning a part of the first wavelength region and a part of the second wavelength region. For example, the filter section 3116 filters light of a band outside the narrowband light being light of a band spanning a part of the B wavelength region and a part of the G wavelength region.

The light emission control section 3124 causes successive emission of a) wideband light being light of a band including the first wavelength region and the second wavelength region and b) narrowband light being light of a band spanning a part of the first wavelength region and a part of the second wavelength region. For example, the light emission control section 3124 causes successive emission of a) wideband light being light of a band including the B wavelength region and the G wavelength region and b) narrowband light being light of a band spanning a part of the B wavelength region and a part of the G wavelength region.

The light emission control section 3124 controls the first light emission section 3112 and the second light emission section 3114 so as to successively emit the above-described wideband light and the above-described narrowband light. The light emission control section 3124 controls the first light emission section 3112 and the filter section 3116, so as to successively emit the above-described wideband light and the above-described narrowband light.

The image capturing control section 3138 captures a image of light received by the first light reception section 3132 when the wideband light is emitted, an image of light received by the second light reception section 3134 when the wideband light is emitted, an image of light received by the first light reception section 3132 when the narrowband light is emitted, and an image of light received by the second light reception section 3134 when the narrowband light is emitted. The image capturing control section 3138 may control the image capturing timing to be concurrent with the light emission timing of the plurality of light emission sections under control of the light emission control section 3124. The image capturing control section 3138 may further capture an image of light received by the third light reception section 3136 when the wideband light is emitted.

The image generating section 3140 generates an image of light other than the narrowband light emitted from the second light emission section 3114 within the first wavelength region, based on the image of light captured by the image capturing control section 3138. In addition, the image generating section 3140 generates an image of light other than the narrowband light emitted from the second light emission section 3114 within the second wavelength region, based on the image of light captured by the image capturing control section 3138.

In the following explanation, an image of wideband light within the first wavelength region is referred to as a first wideband image. In addition, an image of wideband light within the second wavelength region is referred to as a second wideband image. Moreover, an image of wideband light within the third wavelength region is referred to as a third wavelength region.

An image of narrowband light in the first wavelength region is referred to as a first narrowband image. In addition, an image of narrowband light in the second wavelength region is referred to as a second narrowband image.

Moreover, an image of light other than the narrowband light within the first wavelength region is referred to as a third narrowband image. In addition, an image of light other than the narrowband light within the second wavelength region is referred to as a fourth narrowband image.

For example, the image generating section 3140 generates the third narrowband image and the fourth narrowband image, based on the first wideband image, the second wideband image, the first narrowband image, and the second narrowband image captured by the image capturing control section 3138. The image generating section 3140 may calculate the luminance information of the corresponding pixels in the third narrowband image, by subtracting the luminance information of the corresponding pixels in the first narrowband image from the luminance information of the pixels of the first wideband image. In addition, the image generating section 3140 may calculate the luminance information of the corresponding pixels in the fourth narrowband image, by subtracting the luminance information of the corresponding pixels in the second narrowband image from the luminance information of the pixels of the second wideband image.

In another example, the filter section 3116 filters narrowband light being light of a band spanning a part of the first wavelength region and a part of the second wavelength region. For example, the filter section 3116 filters narrowband light being light of a band spanning a part of the B wavelength region and a part of the G wavelength region. In still another example, the light emission control section 3124 controls the first light emission section 3112 and the filter section 3116, so as to successively emit the wideband light and light of a band other than the narrowband light within the wideband light.

In a further different example, the image capturing control section 3138 captures an image of light received by the first light reception section 3132 when the wideband light is emitted, an image of light received by the second light reception section 3134 when the wideband light is emitted, an image of light received by the first light reception section 3132 when light of a band other than the narrowband light is emitted, and an image of light received by the second light reception section 3134 when light of a band other than the narrowband light is emitted. In a still different example, the image generating section 3140 generates the first narrowband image being an image of narrowband light within the first wavelength region and the second narrowband image being an image of narrowband light within the second wavelength region, based on the image of the light captured by the image capturing control section 3138.

The motion detection section 3142 detects relative motion between the image capturing section 3130 and a subject. The motion detection section 3142 may detect relative motion between the image capturing section 3130 and a subject, by using a gyro sensor or the like. The motion detection section 3142 may detect relative motion between the image capturing section 3130 and a subject, from a plurality of wideband images. In this case, the motion detection section 3142 may detect relative motion between the image capturing section 3130 and a subject, based on a landmark such as a blood vessel, scissors, a lesion, or an incision included in a plurality of wideband images.

The motion vector calculation section 3144 calculates a first motion vector of a subject between a timing at which a wideband image is displayed and a timing at which a wideband interpolation image is displayed, based on the motion information detected by the motion detection section 3142. In addition, the motion vector calculation section 3144 calculates a second motion vector of a subject between a timing at which a narrowband image is displayed and a timing at which a wideband interpolation image is displayed, based on the motion information detected by the motion detection section 3142.

The motion vector calculation section 3144 calculates a third motion vector of a subject between a timing at which a narrowband image is displayed and a timing at which a narrowband interpolation image is displayed, based on the motion information detected by the motion detection section 3142. In addition, the motion vector calculation section 3144 calculates a fourth motion vector of a subject between a timing at which a wideband image is displayed and a timing at which a narrowband interpolation image is displayed, based on the motion information detected by the motion detection section 3142.

The wideband image is an image that includes at least one of the first wideband image and the second wideband image. The wideband image may include both of the first wideband image and the second wideband image. The wideband image may further include the third wideband image. The wideband interpolation image is an image interpolating a plurality of wideband images.

The narrowband image is an image that includes at least one of the first narrowband image, the second narrowband image, the third narrowband image, and the fourth narrowband image. The narrowband interpolation image is an image interpolating a plurality of narrowband images.

The wideband interpolation image generating section 3146 generates a wideband interpolation image interpolating a plurality of wideband images, based on the wideband image and the narrowband image. Specifically, the wideband interpolation image generating section 3146 generates a wideband interpolation image frame-interpolating the plurality of wideband images. The wideband interpolation image generating section 3146 may generate a wideband interpolation image based on chromaticity information of the wideband image and brightness information of the narrowband image.

In addition, the wideband interpolation image generating section 3146 may generate a wideband interpolation image further based on the motion information detected by the motion detection section 3142. In addition, the wideband interpolation image generating section 3146 may generate the chromaticity information of the pixels of the wideband interpolation image, from the chromaticity information of the pixels included in the wideband image, based on the first motion vector calculated by the motion vector calculation section 3144. In addition, the wideband interpolation image generating section 3146 may generate the brightness information of the pixels of the wideband interpolation image, from the brightness information of the pixels included in the narrowband image, based on the second motion vector calculated by the motion vector calculation section 3144.

The narrowband interpolation image generating section 3148 generates a narrowband interpolation image interpolating a plurality of narrowband images, based on the wideband image and the narrowband image. Specifically, the narrowband interpolation image generating section 3148 generates a narrowband interpolation image frame-interpolating the plurality of narrowband images. The narrowband interpolation image generating section 3148 may generate a narrowband interpolation image based on the brightness information of the wideband image and the chromaticity information of the narrowband image.

In addition, the narrowband interpolation image generating section 3148 may generate a narrowband interpolation image further based on the motion information detected by the motion detection section 3142. In addition, the narrowband interpolation image generating section 3148 may generate the chromaticity information of the pixels of the narrowband interpolation image, from the chromaticity information of the pixels included in the narrowband image, based on the third motion vector calculated by the motion vector calculation section 3144. In addition, the narrowband interpolation image generating section 3148 may generate the brightness information of the pixels of the narrowband interpolation image, from the brightness information of the pixels included in the wideband image, based on the fourth motion vector calculated by the motion vector calculation section 3144.

The display section 3150 displays a wideband moving image and a narrowband moving image. The wideband moving image is a moving image that includes a plurality of wideband images. The narrowband moving image is a moving image that includes a plurality of narrowband images. The wideband moving image may further include a plurality of wideband interpolation images. The narrowband moving image may further include a plurality of narrowband interpolation images.

The display section 3150 may simultaneously display the wideband moving image and the narrowband moving image. The display section 3150 may simultaneously display the wideband moving image and the narrowband moving image in synchronization with each other. The display section 3150 may display the wideband moving image and the narrowband moving image in alignment with each other. In addition, the display section 3150 may display the wideband moving image and the narrowband moving image overlapped with each other.

FIG. 17 shows an exemplary spectrum of light emitted from a first light emission section 3112 and a second light emission section 3114. The spectrum 3201 represents a spectrum of light emitted from the first light emission section 3112. For example, the first light emission section 3112 emits wideband light including a wavelength region of 400 nm to 750 nm.

The spectrum 3202 represents a spectrum of light emitted from the second light emission section 3114. The second light emission section 3114 emits narrowband light being light of a band spanning a part of the first wavelength region and a part of the second wavelength region. For example, the second light emission section 3114 emits narrowband light that is mainly in a wavelength region of 450 nm to 550 nm.

The spectrum 3202 represents a spectrum of light transmitted by the filter section 3116. The filter section 3116 filters light of a band outside the narrowband light being light of a band spanning a part of the first wavelength region and a part of the second wavelength region. For example, the filter section 3116 filters light of a band outside the narrowband light that is mainly in a wavelength region of 450 nm-550 nm.

Figure 18:
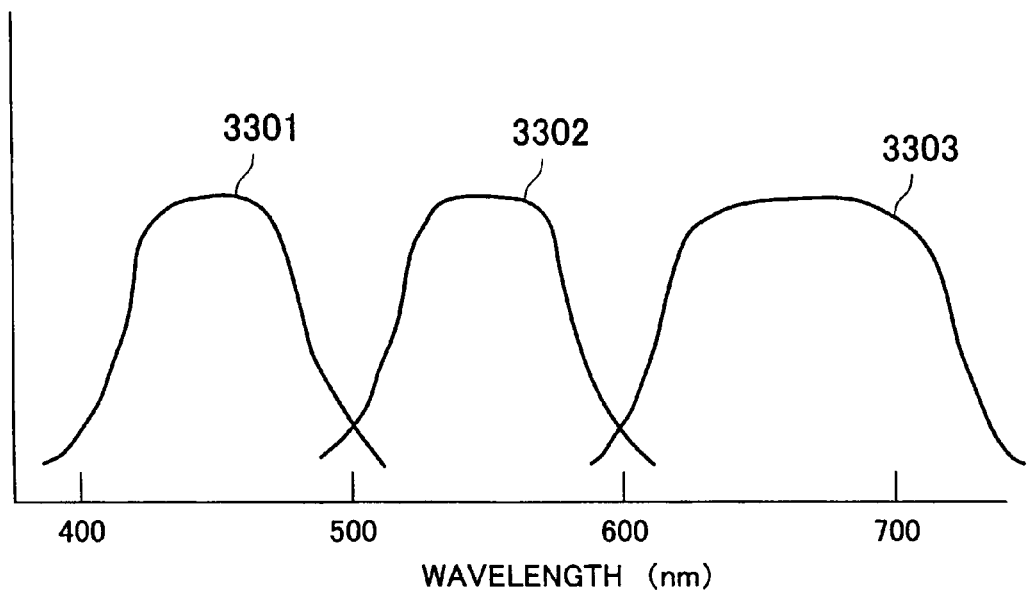
FIG. 18 shows an exemplary light reception characteristic of an image capturing section 3130.

FIG. 18 shows an exemplary light reception characteristic of an image capturing section 3130. The light reception characteristic 3301 represents the light reception characteristic of the first light reception section 3132. For example, the first light reception section 3132 receives light mainly in a wavelength region of 400 nm to 490 nm within the first wavelength region.

The light reception characteristic 3302 represents the light reception characteristic of the second light reception section 3134. For example, the second light reception section 3134 receives light mainly in a wavelength region of 490 nm to 600 nm within the second wavelength region.

The light reception characteristic 3303 represents the light reception characteristic of the third light reception section 3136. For example, the third light reception section 3136 receives light mainly in a wavelength region of 600 nm to 750 nm within the third wavelength region.

Figure 19:
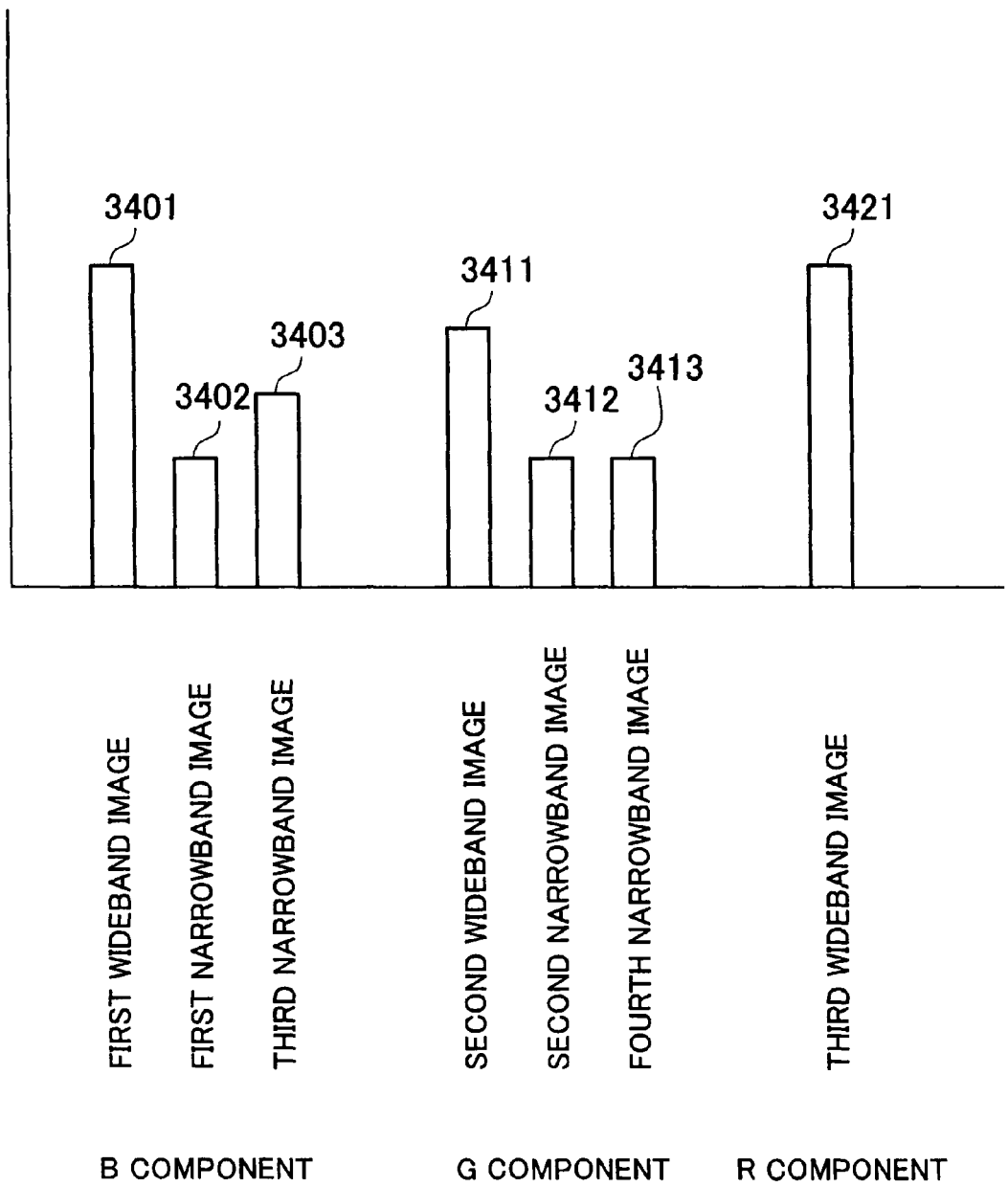
FIG. 19 shows an exemplary image captured by an image capturing control section 3138 and an exemplary image generated by an image generating section 3140.

FIG. 19 shows an exemplary image captured by an image capturing control section 3138 and an exemplary image generated by an image generating section 3140. In FIG. 19, the intensity 3401 represents the intensity of light received by the first light reception section 3132 when the first light emission section 3112 has emitted the wideband light, i.e., the intensity of the first wideband image being an image of B component (i.e. 420 nm-490 nm) in the wideband image captured by the image capturing control section 3138.

The intensity 3411 represents the intensity of light received by the second light reception section 3134 when the first light emission section 3112 has emitted the wideband light, i.e., the intensity of the second wideband image being an image of G component (i.e. 490 nm-600 nm) in the wideband image captured by the image capturing control section 3138. The intensity 3421 represents the intensity of light received by the third light reception section 3136 when the first light emission section 3112 has emitted the wideband light, i.e., the intensity of the third wideband image being an image of R component (i.e. 600 nm-750 nm) in the wideband image captured by the image capturing control section 3138.

The intensity 3402 represents the intensity of light received by the first light reception section 3132 when the second light emission section 3114 has emitted the narrowband light, i.e., the intensity of the first narrowband image being an image of a part of B component (i.e. 450 nm-490 nm) in the narrowband image captured by the image capturing control section 3138. The intensity 3412 represents the intensity of light received by the second light reception section 3134 when the second light emission section 3114 has emitted the narrowband light, i.e., the intensity of the second narrowband image being an image of a part of G component (i.e. 490 nm-550 nm) in the narrowband image captured by the image capturing control section 3138.

The intensity 3403 represents the intensity of the third narrowband image generated by the image generating section 3140, which corresponds to a part of B component (i.e. 400 nm-450 nm). For example, the image generating section 3140 can calculate the intensity 3403 of the third narrowband image by subtracting the intensity 3402 of the first narrowband image from the intensity 3401 of the first wideband image.

The intensity 3413 represents the intensity of the fourth narrowband image generated by the image generating section 3140, which corresponds to a part of G component (i.e. 550 nm-600 nm). For example, the image generating section 3140 can calculate the intensity 3413 of the third narrowband image by subtracting the intensity 3412 of the second narrowband image from the intensity 3411 of the second wideband image.

Figure 20:
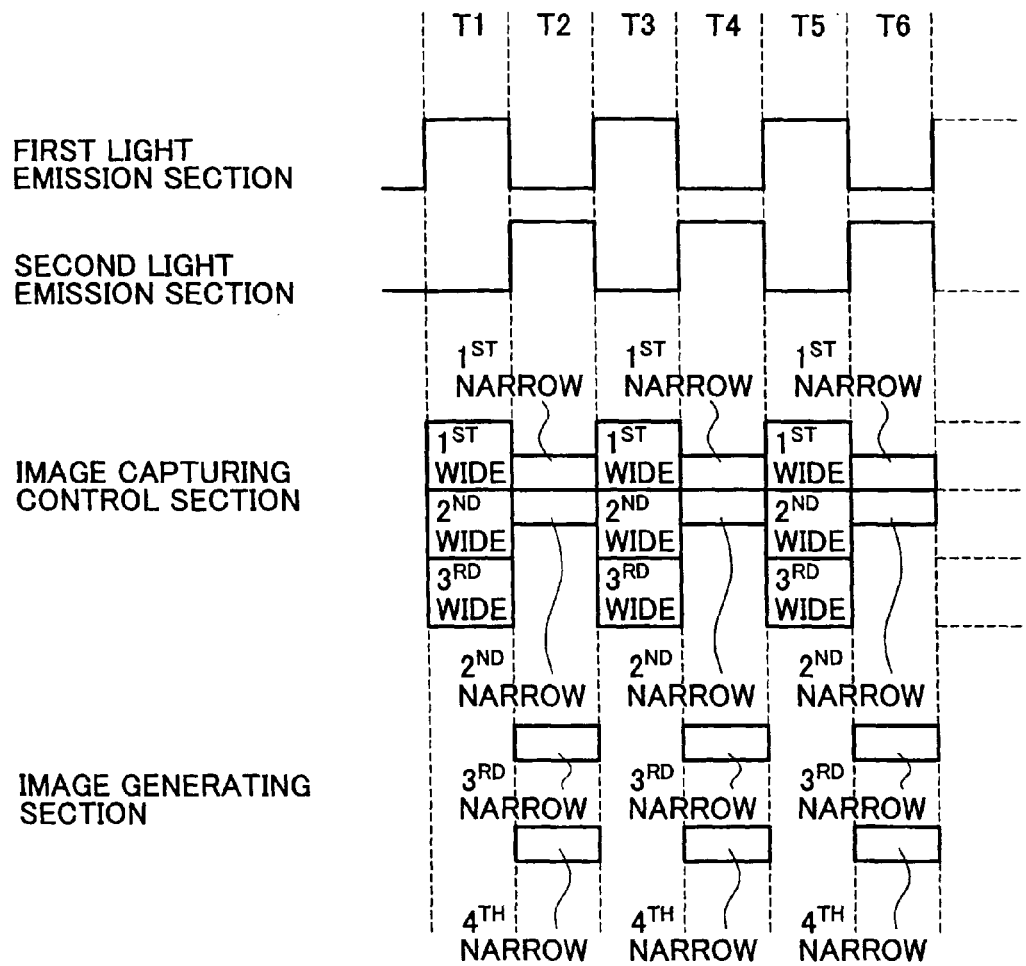
FIG. 20 shows exemplary processing performed by the light emission control section 3124, the image capturing control section 3138, and the image generating section 3140.

FIG. 20 shows exemplary processing performed by the light emission control section 3124, the image capturing control section 3138, and the image generating section 3140. The light emission control section 3124 controls the light emission timings of the first light emission section 3112 and the second light emission section 3114.

For example, at the timings T1, T3, and T5, the light emission control section 3124 controls the first light emission section 3112 to emit light. According to this, the image capturing control section 3138, for example, captures the first wideband image, the second wideband image, and the third wideband image, at the timings T1, T3, and T5.

At the timings T2, T4, and T6, the light emission control section 3124 controls the second light emission section 3114 to emit light. According to this, the image capturing control section 3138, for example, captures the first narrowband image and the second narrowband image, at the timings T2, T4, and T6, respectively.

At the timings T2, T4, and T6, the image generating section 3140 generates the third narrowband image and the fourth narrowband image, at the timings T2, T4, and T6. For example, the image generating section 3140 generates the third narrowband image and the fourth narrowband image, based on the first wideband image and the second wideband image captured at a prior timing as well as the first narrowband image and the second narrowband image captured at the same timing.

Figure 21:
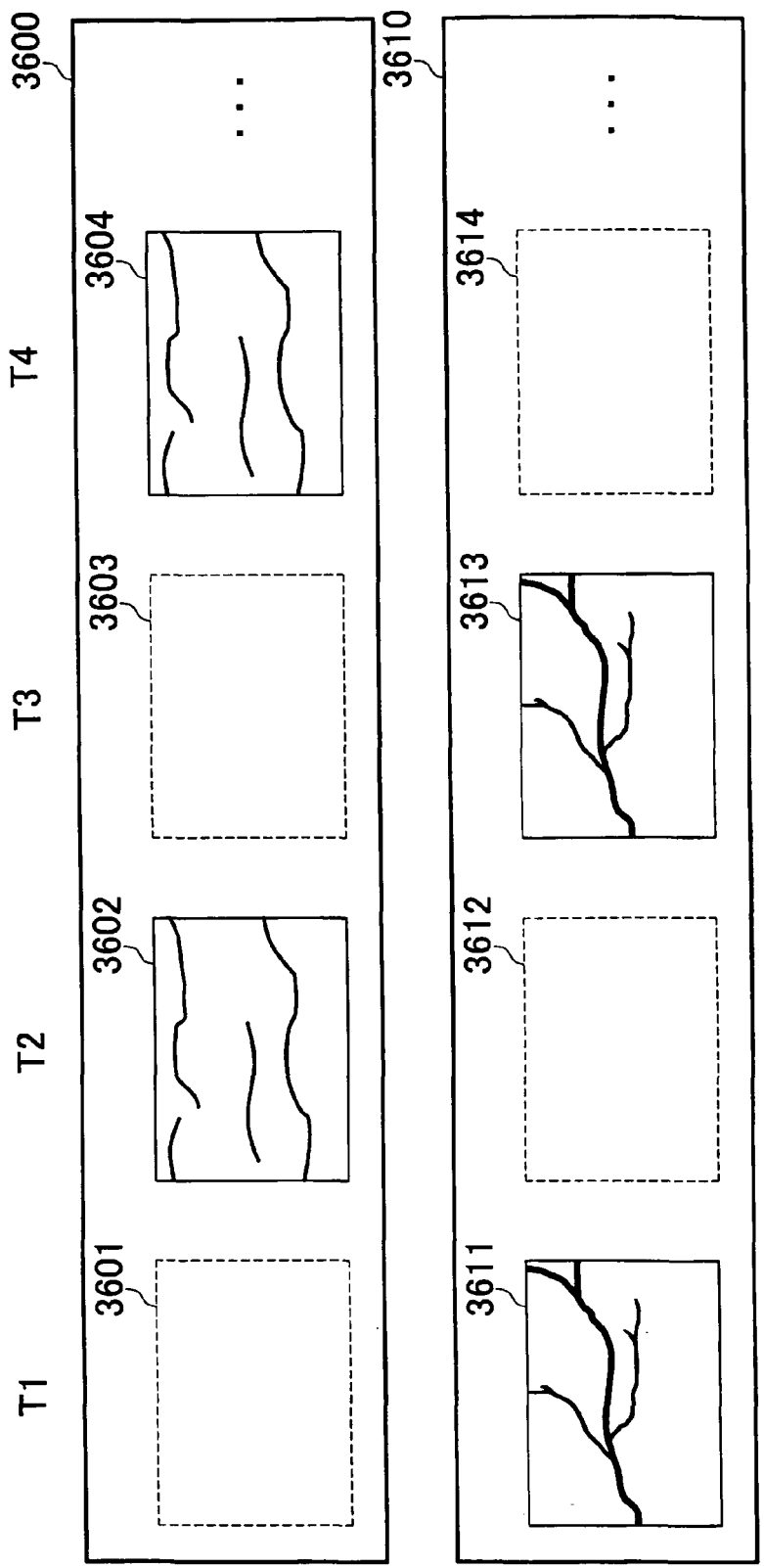
FIG. 21 shows an example of a wideband moving image and a narrowband moving image, which are displayed by a display section 3150.

FIG. 21 shows an example of a wideband moving image and a narrowband moving image, which are displayed by a display section 3150. In FIG. 21, the moving image 3600 represents a wideband moving image that includes a plurality of wideband images. In addition, the moving image 3610 represents a narrowband moving image that includes a plurality of narrowband images.

In the moving image 3600, each of the image 3602 and the image 3604 represents a wideband image that includes a wideband image captured by the image capturing control section 3138. For example, the image 3602 and the image 3604 include a first wideband image, a second wideband image, and a third wideband image captured by the image capturing control section 3138.

In the moving image 3610, each of the image 3611 and the image 3613 represents a narrowband image that includes a narrowband image generated by the image generating section 3140. For example, the image 3611 and the image 3613 include a third narrowband image and a fourth narrowband image generated by the image generating section 3140.

The wideband interpolation image generating section 3146 may generate a wideband interpolation image interpolating a plurality of wideband images. For example, the wideband interpolation image generating section 3146 may generate a wideband interpolation image 3601 that is a wideband image at the timing T1. In addition, the wideband interpolation image generating section 3146 may generate a wideband interpolation image 3603 that is a wideband image at the timing T3.

The wideband interpolation image generating section 3146 may generate a wideband interpolation image based on the chromaticity information of a wideband image and the brightness information of a narrowband image. For example, the wideband interpolation image generating section 3146 may generate a wideband interpolation image based on the chromaticity information of the wideband image at the prior or subsequent timing, and the brightness information of the narrowband image at the same timing. The wideband interpolation image generating section 3146 may generate the wideband interpolation image, further based on the brightness information of narrowband images other than the narrowband image at the same timing. The wideband interpolation image generating section 3146 may generate the wideband interpolation image, further based on the brightness information of the wideband image of the prior or subsequent timing. The wideband interpolation image generating section 3146 may generate the wideband interpolation image, further based on the motion information detected by the motion detection section 3142.

The wideband interpolation image generating section 3146 may generate the chromaticity information of the pixels of the wideband interpolation image, from the chromaticity information of the pixels included in the wideband image, based on the first motion vector calculated by the motion vector calculation section 3144. The first motion vector is a motion vector of a subject between a timing at which a wideband image is displayed and a timing at which a wideband interpolation image is displayed. For example, the wideband interpolation image generating section 3146 may generate the chromaticity information of the pixels of the wideband interpolation image from the chromaticity information of the pixels included in the wideband image before or after the wideband interpolation image, based on the first motion vector between the timing at which the wideband image before or after the wideband interpolation image is displayed and the timing at which the wideband interpolation image is displayed.

The wideband interpolation image generating section 3146 may generate the brightness information of the pixels of the wideband interpolation image, from the brightness information of the pixels included in the narrowband image, based on the second motion vector calculated by the motion vector calculation section 3144. The second motion vector is a motion vector of a subject between a timing at which a narrowband image is displayed and a timing at which a wideband interpolation image is displayed. The image generating section 3140 may generate the chromaticity information of the pixels of the wideband interpolation image from the chromaticity information of the pixels included in the narrowband image before or after the wideband interpolation image, based on the second motion vector between the timing at which the narrowband image before or after the wideband interpolation image is displayed and the timing at which the wideband interpolation image is displayed.

The narrowband interpolation image generating section 3148 may generate a narrowband interpolation image interpolating a plurality of narrowband images. For example, the narrowband interpolation image generating section 3148 may generate a narrowband interpolation image 3612 that is a narrowband image at the timing T2. In addition, the narrowband interpolation image generating section 3148 may generate a narrowband interpolation image 3614 that is a narrowband image at the timing T4.

The narrowband interpolation image generating section 3148 may generate a narrowband interpolation image based on the brightness information of a wideband image and the chromaticity information of a narrowband image. For example, the narrowband interpolation image generating section 3148 may generate a narrowband interpolation image based on the chromaticity information of the narrowband image at the prior or subsequent timing, and the brightness information of the wideband image at the same timing. The narrowband interpolation image generating section 3148 may generate the narrowband interpolation image, further based on the brightness information of wideband images other than the wideband image at the same timing. The narrowband interpolation image generating section 3148 may generate the narrowband interpolation image, further based on the brightness information of the narrowband image of the prior or subsequent timing. The narrowband interpolation image generating section 3148 may generate the narrowband interpolation image, further based on the motion information detected by the motion detection section 3142.

The narrowband interpolation image generating section 3148 may generate the chromaticity information of the pixels of the narrowband interpolation image, from the chromaticity information of the pixels included in the narrowband image, based on the third motion vector calculated by the motion vector calculation section 3144. The third motion vector is a motion vector of a subject between a timing at which a narrowband image is displayed and a timing at which a narrowband interpolation image is displayed. For example, the narrowband interpolation image generating section 3148 may generate the chromaticity information of the pixels of the narrowband interpolation image from the chromaticity information of the pixels included in the narrowband image before or after the narrowband interpolation image, based on the third motion vector between the timing at which the narrowband image before or after the narrowband interpolation image is displayed and the timing at which the narrowband interpolation image is displayed.

The narrowband interpolation image generating section 3148 may generate the brightness information of the pixels of the narrowband interpolation image, from the brightness information of the pixels included in the wideband image, based on the fourth motion vector calculated by the motion vector calculation section 3144. The fourth motion vector is a motion vector of a subject between a timing at which a wideband image is displayed and a timing at which a narrowband interpolation image is displayed. The narrowband interpolation image generating section 3148 may generate the chromaticity information of the pixels of the narrowband interpolation image from the chromaticity information of the pixels included in the wideband image before or after the narrowband interpolation image, based on the fourth motion vector between the timing at which the wideband image before or after the narrowband interpolation image is displayed and the timing at which the narrowband interpolation image is displayed.

FIG. 22 shows exemplary display processing performed by the display section 3150. The screen 3700 displays a moving image 3600 and a moving image 3610. The moving image 3600 represents a wideband moving image that includes a plurality of wideband images. The display section 3150 may display a wideband moving image that includes only one of the first wideband image, the second wideband image, the third wideband image, and the fourth wideband image. The display section 3150 may display a wideband moving image that includes two or more of the first wideband image, the second wideband image, the third wideband image, and the fourth wideband image.

The display section 3150 may display a narrowband moving image that includes only one of the first narrowband image, the second narrowband image, the third narrowband image, and the fourth narrowband image. The display section 3150 may display a narrowband moving image that includes two or more of the first narrowband image, the second narrowband image, the third narrowband image, and the fourth narrowband image.

The display section 3150 may display a plurality of moving images in alignment with each other. In addition, the display section 3150 may display a plurality of moving images in synchronization with each other.

Figure 23:
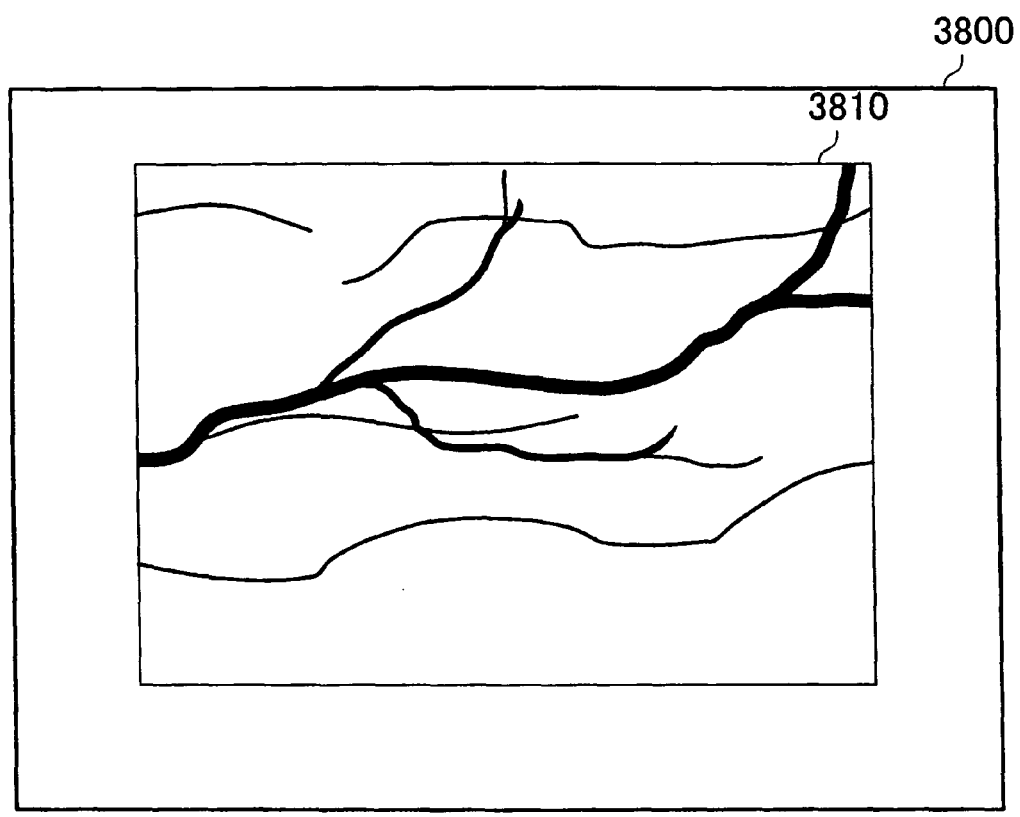
FIG. 23 shows different exemplary display processing performed by the display section 3150.

FIG. 23 shows different exemplary display processing performed by the display section 3150. The screen 3800 displays a combined moving image 3810. In the combined moving image 3810, combined are a wideband moving image that includes a plurality of wideband images and a narrowband moving image that includes a plurality of narrowband images. In this way, the display section 3150 may display a plurality of moving images by overlapping them with each other.

Figure 24:
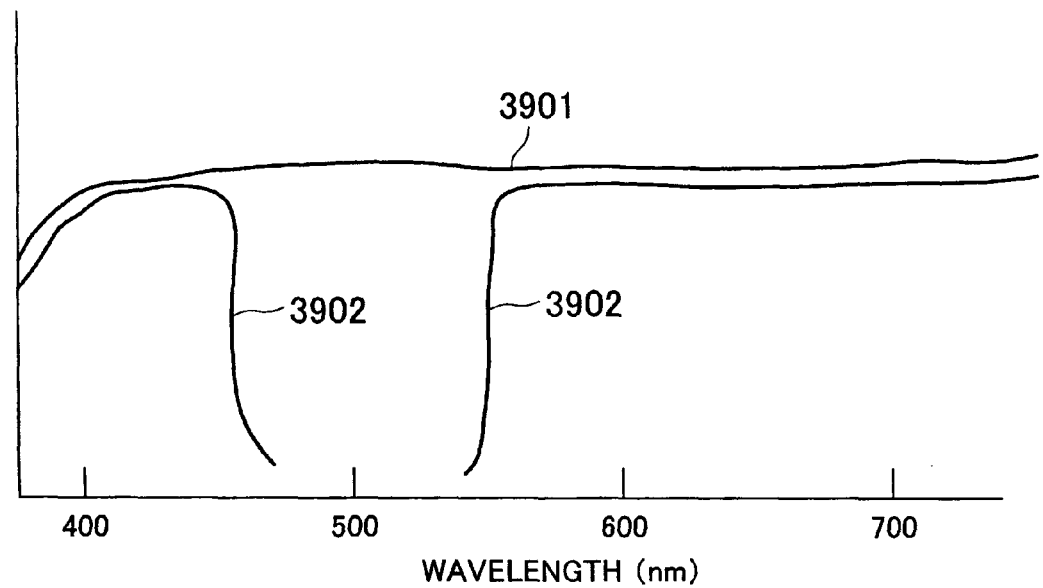
FIG. 24 shows an exemplary spectrum of light emitted from a first light emission section 3112 and a filter section 3116.

FIG. 24 shows an exemplary spectrum of light emitted from a first light emission section 3112 and a filter section 3116. The spectrum 3901 represents a spectrum of light emitted from the first light emission section 3112. For example, the first light emission section 3112 emits light of a wideband region including a wavelength region of 400 nm to 750 nm.

The spectrum 3902 represents a spectrum of light emitted from the first light emission section 3112 and then filtered by the filter section 3116. The filter section 3116 filters narrowband light being light of a band spanning a part of the first wavelength region and a part of the second wavelength region. For example, the filter section 3116 filters narrowband light that is mainly in a wavelength region of 450 nm to 550 nm.

Figure 25:
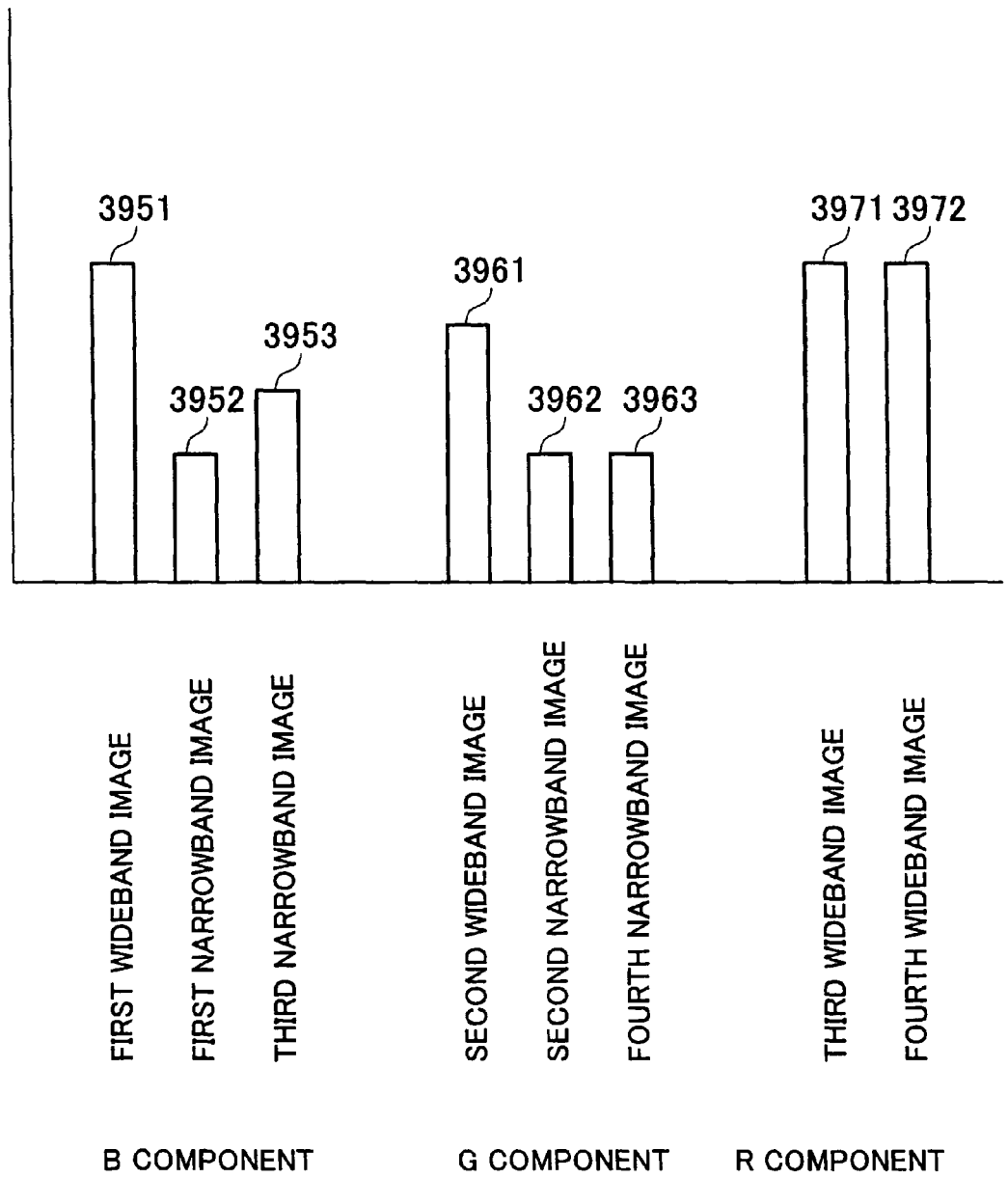
FIG. 25 shows another exemplary image captured by the image capturing control section 3138 and another exemplary image generated by the image generating section 3140.

FIG. 25 shows another exemplary image captured by the image capturing control section 3138 and another exemplary image generated by the image generating section 3140. In FIG. 25, the intensity 3951 represents the intensity of light received by the first light reception section 3132 when the first light emission section 3112 has emitted the wideband light, i.e., the intensity of the first wideband image being an image of B component (i.e. 420 nm-490 nm) in the wideband image captured by the image capturing control section 3138.

The intensity 3961 represents the intensity of light received by the second light reception section 3134 when the first light emission section 3112 has emitted the wideband light, i.e., the intensity of the second wideband image being an image of G component (i.e. 490 nm-600 nm) in the wideband image captured by the image capturing control section 3138. The intensity 3971 represents the intensity of light received by the third light reception section 3136 when the first light emission section 3112 has emitted the wideband light, i.e., the intensity of the third wideband image being an image of R component (i.e. 600 nm-750 nm) in the wideband image captured by the image capturing control section 3138.

The intensity 3953 represents the intensity of light received by the first light reception section 3132 when the filter section 3116 has filtered the wideband light emitted from the first light emission section 3112, i.e., the intensity of the third narrowband image being an image of a part of B component (i.e. 400 nm-450 nm) in the narrowband image captured by the image capturing control section 3138. The intensity 3963 represents the intensity of light received by the second light reception section 3134 when the filter section 3116 has filtered the wideband light emitted from the first light emission section 3112, i.e., the intensity of the fourth narrowband image being an image of a part of G component (i.e. 550 nm-600 nm) in the narrowband image captured by the image capturing control section 3138. The intensity 3972 represents the intensity of light received by the third light reception section 3136 when the filter section 3116 has filtered the wideband light emitted from the first light emission section 3112, i.e., the intensity of the fourth wideband image being an image of a part of R component (i.e. 600 nm-750 nm) in the wideband image captured by the image capturing control section 3138.

The intensity 3952 represents the intensity of the first narrowband image generated by the image generating section 3140, which corresponds to a part of B component (i.e. 450 nm-490 nm). For example, the image generating section 3140 can calculate the intensity 3952 of the first narrowband image by subtracting the intensity 3953 of the third narrowband image from the intensity 3951 of the first wideband image.

The intensity 3962 represents the intensity of the second narrowband image generated by the image generating section 3140, which corresponds to a part of G component (i.e. 490 nm-550 nm). For example, the image generating section 3140 can calculate the intensity 3962 of the second narrowband image by subtracting the intensity 3963 of the fourth narrowband image from the intensity 3961 of the second wideband image.

Figure 26:
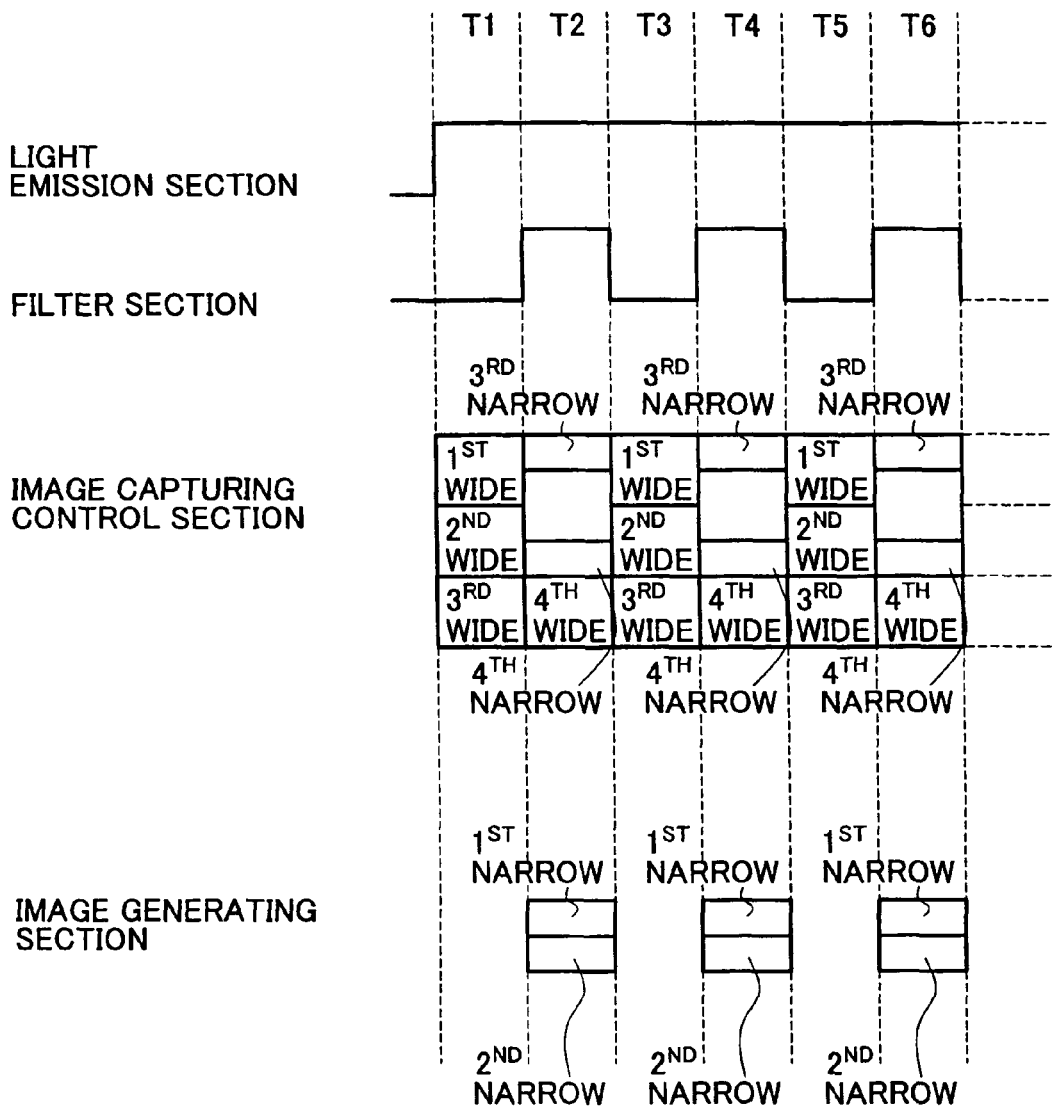
FIG. 26 shows different exemplary processing performed by the light emission control section 3124, the image capturing control section 3138, and the image generating section 3140.

FIG. 26 shows different exemplary processing performed by the light emission control section 3124, the image capturing control section 3138, and the image generating section 3140. The light emission control section 3124 controls the light emission timing of the first light emission section 3112 and the filtering timing of the filter section 3116.

For example, the light emission control section 3124 controls the first light emission section 3112 to emit wideband light from the timing T1 in succession. In addition, the light emission control section 3124 controls the filter section 3116 to filter the wideband light emitted from the first light emission section 3112 at each of the timings T2, T4, and T6.

Accordingly, the image capturing control section 3138 captures the first wideband image, the second wideband image, and the third wideband image, at the timings T1, T3, and T5. In addition, the image capturing control section 3138 captures the third narrowband image, the fourth narrowband image, and the fourth wideband image, at the timings T2, T4, and T6.

The image generating section 3140 generates the first narrowband image and the second narrowband image at the timings T2, T4, and T6. For example, the image generating section 3140 generates the first narrowband image and the second narrowband image, based on the first wideband image and the second wideband image captured at a prior timing as well as the third narrowband image and the fourth narrowband image captured at the same timing.

In this way, the image capturing apparatus 3100 of the present embodiment is able to obtain a plurality of narrowband images, the bands of which at the same timing are different from each other. For example, when capturing an image of blood vessels using an endoscope, the image capturing apparatus 3100 in the present embodiment can simultaneously obtain an image of a plurality of blood vessels having respectively different depths or particular component's concentrations. In addition, the image capturing apparatus 3100 of the present embodiment is able to generate a narrowband interpolation image and a wideband interpolation image, thereby enabling to generate a narrowband image and a wideband image belonging to the same timing.

Figure 27:
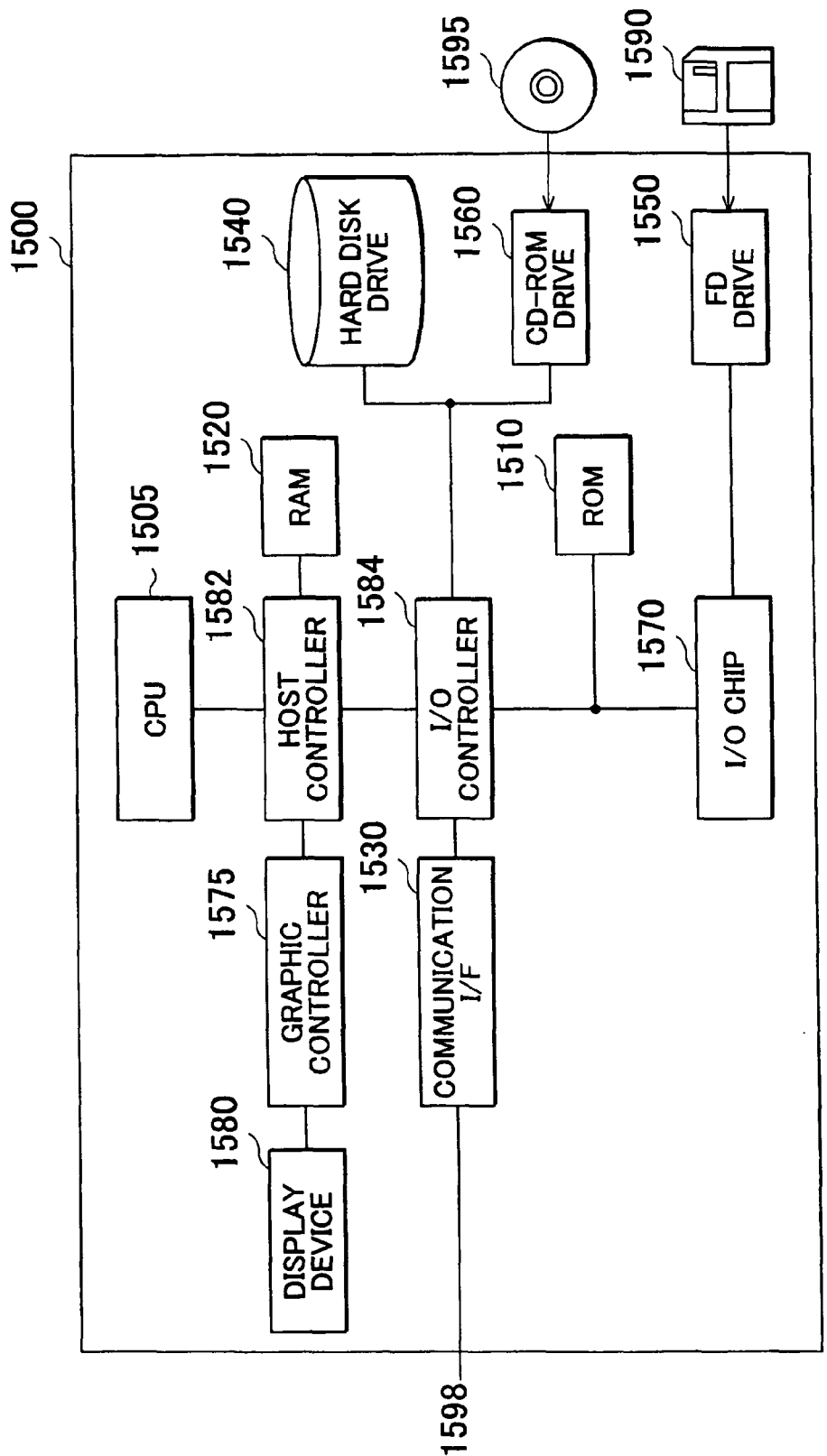
FIG. 27 shows an exemplary hardware configuration of a computer 1500 that functions as the endoscope system 10, the image capturing apparatus 2100, and the image capturing apparatus 3100.

FIG. 27 shows an exemplary hardware configuration of a computer 1500 that functions as the endoscope system 10, the image capturing apparatus 2100, and the image capturing apparatus 3100. The endoscope system 10 is able to be constructed using the computer 1500 such as a personal computer.

FIG. 14 shows an exemplary hardware configuration of a computer 1500 that functions as a position specifying system 10. The CPU peripheral section includes a CPU 1505, a RAM 1520, a graphic controller 1575, and a display device 1580 connected to each other by a host controller 1582. The input/output section includes a communication interface 1530, a hard disk drive 1540, and a CD-ROM drive 1560, all of which are connected to the host controller 1582 by an input/output controller 1584. The legacy input/output section includes a ROM 1510, a flexible disk drive 1550, and an input/output chip 1570, all of which are connected to the input/output controller 1584.

The host controller 1582 is connected to the RAM 1520 and is also connected to the CPU 1505 and the graphic controller 1575 accessing the RAM 1520 at a high transfer rate. The CPU 1505 operates to control each section based on programs stored in the ROM 1510 and the RAM 1520. The graphic controller 1575 obtains image data generated by the CPU 1505 or the like on a frame buffer provided inside the RAM 1520 and displays the image data in the display device 1580. Alternatively, the graphic controller 1575 may internally include the frame buffer storing the image data generated by the CPU 1505 or the like.

The input/output controller 1584 connects the communication interface 1530 serving as a relatively high speed input/output apparatus, the hard disk drive 1540, and the CD-ROM drive 1560 to the host controller 1582. The hard disk drive 1540 stores the programs and data used by the CPU 1505. The communication interface 1530 transmits or receives programs and data by connecting to the network communication apparatus 1598. The CD-ROM drive 1560 reads the programs and data from a CD-ROM 1595 and provides the read programs and data to the hard disk drive 1540 and to the communication interface 1530 via the RAM 1520.

Furthermore, the input/output controller 1584 is connected to the ROM 1510, and is also connected to the flexible disk drive 1550 and the input/output chip 1570 serving as a relatively low speed input/output apparatus. The ROM 1510 stores a boot program executed when the computer 1500 starts up, a program relying on the hardware of the computer 1500, and the like. The flexible disk drive 1550 reads programs or data from a flexible disk 1590 and supplies the read programs or data to the hard disk drive 1540 and to the communication interface 1530 via the RAM 1520. The input/output chip 1570 is connected to a variety of input/output apparatuses via the flexible disk drive 1550, and a parallel port, a serial port, a keyboard port, a mouse port, or the like, for example.

A program executed by the CPU 1505 is supplied by a user by being stored in a recording medium such as the flexible disk 1590, the CD-ROM 1595, or an IC card. The program stored in the recording medium may or may not be in a compressed form. The program is installed to the hard disk drive 1540 from the recording medium, and is read by the RAM 1520 to be executed by the CPU 1505. The program executed by the CPU 1505 causes the computer 1500 to function as each constituting element of the endoscope system 10 explained with reference to FIGS. 1-8, e.g., the light irradiation section 120, the control section 105, the image processing section 140, the output section 150, the ICG injection section 170, and the image capturing section 110. In addition, the program executed by the CPU 1505 causes the computer 1500 to function as each functional section included in the image capturing apparatus 2100 explained with reference to FIGS. 9-15, e.g., the light emission section 2110, the light emission control section 2124, the image capturing section 2130, the image capturing control section 2138, the motion detection section 2142, the motion vector calculation section 2144, the wideband interpolation image generating section 2146, the narrowband interpolation image generating section 2148, and the display section 2150. In addition, the program executed by the CPU 1505 causes the computer 1500 to function as each functional section included in the image capturing apparatus 3100 explained with reference to FIGS. 16-26, e.g., the first light emission section 3112, the second light emission section 3114, the filter section 3116, the light emission control section 3124, the image capturing section 3130, the image capturing control section 3138, the image generating section 3140, the motion detection section 3142, the motion vector calculation section 3144, the wideband interpolation image generating section 3146, the narrowband interpolation image generating section 3148, and the display section 3150.

The program mentioned above may be stored in an external recording medium. The recording medium may be an optical recording medium such as DVD or PD, a magneto-optical recording medium such as MD, a tape medium, and a semiconductor memory such as an IC card, etc., in addition to the flexible disk 1590 and the CD-ROM 1595. The recording medium may further be a hard disk or RAM provided for a server system connected via the dedicated communication network or the Internet, to provide a program to the computer 1500 via the network.

Although some aspects of the present invention have been described by way of exemplary embodiments, it should be understood that those skilled in the art might make many changes and substitutions without departing from the spirit and the scope of the present invention which is defined only by the appended claims.

The operations, the processes, the steps, or the like in the apparatus, the system, the program, and the method described in the claims, the specification, and the drawings are not necessarily performed in the described order. The operations, the processes, the steps, or the like can be performed in an arbitrary order, unless the output of the former-described processing is used in the later processing. Even when expressions such as "First," or "Next," or the like are used to explain the operational flow in the claims, the specification, or the drawings, they are intended to facilitate the understanding of the invention, and are never intended to show that the described order is mandatory.

What is claimed is:

1. An image capturing apparatus, comprising:
a first light reception section that receives light of a first wavelength region;
a second light reception section that receives light of a second wavelength region that is different from the first wavelength region;
a light emission control section that causes successive emission of a) wideband light of a band that includes the first wavelength region and the second wavelength region, and b) partial band light that mainly includes light of a part of the first wavelength region and a part of the second wavelength region;
an image capturing control section that captures a) a first wideband image of light received by the first reception section when the wideband light has been emitted, b) a second wideband image of light received by the second light reception section when the wideband light has been emitted, c) a first narrowband image of light received by the first light reception section when the partial band light has been emitted and d) a second narrowband image of light received by the second light reception section when the partial band light has been emitted; and
an image generating section that generates, based on a) the first wideband image of light received by the first light reception section, b) the second wideband image of light received by the second light reception section, c) the first narrowband image of light received by the first light reception section and d) the second narrowband image of light received by the second light reception section, i) a third narrowband image of light other than the partial band light within the first wavelength region, and ii) a fourth narrowband image of light other than the partial band light within the second wavelength region, wherein an intensity of the third narrowband image is calculated by subtracting an intensity of the first narrowband image from an intensity of the first wideband image, and an intensity of the fourth narrowband image is calculated by subtracting the intensity of an second narrowband image from an intensity of the second wideband image.

2. The image capturing apparatus according to claim 1, wherein the light emission control section causes successive emission of the wideband light and narrowband light being light of a band spanning a part of the first wavelength region and a part of the second wavelength region.

3. The image capturing apparatus according to claim 2, further comprising:
   a first light emission section that emits the wideband light; and
   a second light emission section that emits the narrowband light,
   wherein the light emission control section controls the first light emission section and the second light emission section to successively emit the wideband light and the narrowband light.

4. The image capturing apparatus according to claim 2, further comprising:
   a light emission section that emits the wideband light; and
   a filter section that filters light of a band other than the narrowband light,
   wherein the light emission control section controls the light emission section and the filter section to successively emit the wideband light and the narrowband light.

5. The image capturing apparatus according to claim 1, further comprising:
   a light emission section that emits the wideband light; and
   a filter section that filters narrowband light of a band spanning a part of the first wavelength region and a part of the second wavelength region,
   wherein the light emission control section controls the light emission section and the filter section to successively emit the wideband light and light of a band other than the narrowband light within the wideband light.

6. The image capturing apparatus according to claim 1, further comprising a wideband interpolation image generating section that generates a wideband interpolation image interpolating a plurality of wideband images, based on the wideband image and the narrowband image.

7. The image capturing apparatus according to claim 6, wherein the wideband interpolation image generating section generates the wideband interpolation image, based on chromaticity information of the wideband image and brightness information of the narrowband image.

8. The image capturing apparatus according to claim 7, further comprising a motion detection section that detects relative motion between the image capturing section and the subject,
   wherein the wideband interpolation image generating section generates the wideband interpolation image, further based on motion information detected by the motion detection section.

9. The image capturing apparatus according to claim 8, further comprising a motion vector calculation section that calculates a first motion vector of the subject between a timing at which the wideband image is displayed and a timing at which the wideband interpolation image is displayed, based on the motion information detected by the motion detection section, wherein the wideband interpolation image generating section generates chromaticity information of pixels of the wideband interpolation image from chromaticity information of pixels included in the wideband image, based on the first motion vector calculated by the motion vector calculation section.

10. The image capturing apparatus according to claim 8, wherein the motion vector calculation section calculates a second motion vector of the subject between a timing at which the narrowband image is displayed and a timing at which the wideband interpolation image is displayed, based on the motion information detected by the motion detection section, and
   the wideband interpolation image generating section generates brightness information of pixels of the wideband interpolation image from brightness information of pixels included in the narrowband image, based on the second motion vector calculated by the motion vector calculation section.

11. The image capturing apparatus according to claim 1, further comprising a narrowband interpolation image generating section that generates a narrowband interpolation image interpolating a plurality of narrowband images, based on the wideband image and the narrowband image.

12. The image capturing apparatus according to claim 11, wherein the narrowband interpolation image generating section generates the narrowband interpolation image, based on brightness information of the wideband image and chromaticity information of the narrowband image.

13. The image capturing apparatus according to claim 1, further comprising a motion detection section that detects relative motion between the image capturing section and the subject,
   wherein the narrowband interpolation image generating section generates the narrowband interpolation image, further based on motion information detected by the motion detection section.

14. The image capturing apparatus according to claim 13, further comprising a motion vector calculation section that calculates a third motion vector of the subject between a timing at which the narrowband image is displayed and a timing at which the narrowband interpolation image is displayed, based on the motion information detected by the motion detection section,
   wherein the narrowband interpolation image generating section generates chromaticity information of pixels of the narrowband interpolation image from chromaticity information of pixels included in the narrowband image, based on the third motion vector calculated by the motion vector calculation section.

15. The image capturing apparatus according to claim 14, wherein the motion vector calculation section calculates a fourth motion vector of the subject between a timing at which the wideband image is displayed and a timing at which the narrowband interpolation image is displayed, based on the motion information detected by the motion detection section, and
   the narrowband interpolation image generating section generates brightness information of pixels of the narrowband interpolation image from brightness information of pixels included in the wideband image, based on the fourth motion vector calculated by the motion vector calculation section.

16. An image capturing method used in an image capturing apparatus, the image capturing apparatus including: a first light reception section that receives light of a first wavelength region; and a second light reception section that receives light of a second wavelength region that is different from the first wavelength region, the image capturing method comprising:
  causing successive emission of a) wideband light of a band that includes the first wavelength region and the second wavelength region, and b) partial band light that mainly includes a part of the first wavelength region and a part of the second wavelength region;
  capturing a) a first wideband image of light received by the first light reception section when the wideband light has been emitted, b) a second wideband image of light received by the second light reception section when the wideband light has been emitted, c) a first narrowband image of light received by the first light reception section when the partial band light has been emitted, and d) a second narrowband image of light received by the second light reception section when the partial band light has been emitted; and
  generating, based on a) the first wideband image of light received by the first light reception section, b) the second wideband image of light received by the second light reception section, c) the first narrowband image of light received by the first light reception section and d) the second narrowband image of light received by the second light reception section, i) a third narrowband image of light other than the partial band light within the first wavelength region, and ii) a fourth narrowband image of light other than the partial band light within the second wavelength region,
  wherein an intensity of the third narrowband image is calculated by subtracting an intensity of the first narrowband image from an intensity of the first wideband image, and an intensity of the fourth narrowband image is calculated by subtracting the intensity of an second narrowband image from an intensity of the second wideband image.

17. A non-transitory computer readable medium storing therein a program for an image capturing apparatus, the image capturing apparatus including: a first light reception section that receives light of a first wavelength region; and a second light reception section that receives light of a second wavelength region that is different from the first wavelength region, the program causing a computer to function as:
  a light emission control section that causes successive emission of a) wideband light of a band that includes the first wavelength region and the second wavelength region, and b) partial band light that mainly includes light of a part of the first wavelength region and a part of the second wavelength region;
  an image capturing control section that captures a) a first wideband image of light received by the first light reception section when the wideband light has been emitted, b) a second wideband image of light received by the second light reception section when the wideband light has been emitted, c) a first narrowband image of light received by the first light reception section when the partial band light has been emitted, and d) a second narrowband image of light received by the second light reception section when the partial band light has been emitted; and
  an image generating section that generates, based on a) the first wideband image of light received by the first light reception section, b) the second wideband image of light received by the second light reception section, c) the first narrowband image of light received by the first light reception section and d) the second narrowband image of light received by the second light reception section, i) a third narrowband image of light other than the partial band light within the first wavelength region, and ii) a fourth narrowband image of light other than the partial band light within the second wavelength region,
  wherein an intensity of the third narrowband image is calculated by subtracting an intensity of the first narrowband image from an intensity of the first wideband image, and an intensity of the fourth narrowband image is calculated by subtracting the intensity of an second narrowband image from an intensity of the second wideband image.

\* \* \* \* \*